(12) United States Patent
Jones et al.

(10) Patent No.: US 11,253,368 B2
(45) Date of Patent: Feb. 22, 2022

(54) METHODS OF DESIGNING HIGH X-RAY LUCENCY LATTICE STRUCTURES

(71) Applicant: NANOHIVE MEDICAL LLC, Woburn, MA (US)

(72) Inventors: Christopher L. Jones, Malden, MA (US); Ian Helmar, Beverly, MA (US); Lucas Diehl, Beverly, MA (US); Jason Tinley, Fort Worth, TX (US); Kevin D. Chappuis, Malden, MA (US); John F. Sullivan, Pelham, NH (US)

(73) Assignee: NANOHIVE MEDICAL LLC, Woburn, MA (US)

( * ) Notice: Subject to any disclaimer, the term of this patent is extended or adjusted under 35 U.S.C. 154(b) by 512 days.

(21) Appl. No.: 15/895,213

(22) Filed: Feb. 13, 2018

(65) Prior Publication Data

US 2018/0228613 A1 Aug. 16, 2018

Related U.S. Application Data

(60) Provisional application No. 62/480,383, filed on Apr. 1, 2017, provisional application No. 62/480,385, filed
(Continued)

(51) Int. Cl.
*B33Y 50/00* (2015.01)
*A61F 2/30* (2006.01)
(Continued)

(52) U.S. Cl.
CPC .......... *A61F 2/30767* (2013.01); *A61B 90/39* (2016.02); *A61F 2/30942* (2013.01);
(Continued)

(58) Field of Classification Search
CPC .... A61F 2002/3009; A61F 2002/30141; A61F 2002/30143; A61F 2002/30146;
(Continued)

(56) References Cited

U.S. PATENT DOCUMENTS 5,615,528 A 4/1997 Owens
5,674,294 A 10/1997 Bainville et al.
(Continued)

FOREIGN PATENT DOCUMENTS

CN 204971711 U 1/2016
EP 1506753 A1 2/2005
(Continued)

OTHER PUBLICATIONS

Ahmadi, S. et al., "Additively Manufactured Open-Cell Porous Biomaterials Made from Six Different Space-Filling Unit Cells: The Mechanical and Morphological Properties," Materials, vol. 8:1871-1896 (2015).
(Continued)

*Primary Examiner* — Kibrom K Gebresilassie
(74) *Attorney, Agent, or Firm* — White & Case LLP

(57) ABSTRACT

The biocompatible lattice structures disclosed herein with an increased or optimized lucency are prepared according to multiple methods of design disclosed herein. The methods allow for the design of a metallic material with sufficient strength for use in an implant and that remains radiolucent for x-ray imaging.

11 Claims, 27 Drawing Sheets

Related U.S. Application Data on Apr. 1, 2017, provisional application No. 62/619,260, filed on Jan. 19, 2018, provisional application No. 62/458,714, filed on Feb. 14, 2017.

(51) Int. Cl.
*A61F 2/44* (2006.01)
*A61B 90/00* (2016.01)

(52) U.S. Cl.
CPC .............. *A61F 2/44* (2013.01); *A61F 2/4455* (2013.01); *B33Y 50/00* (2014.12); *A61B 2090/3966* (2016.02); *A61F 2/30771* (2013.01); *A61F 2002/3008* (2013.01); *A61F 2002/3009* (2013.01); *A61F 2002/3028* (2013.01); *A61F 2002/30028* (2013.01); *A61F 2002/3092* (2013.01); *A61F 2002/3093* (2013.01); *A61F 2002/30141* (2013.01); *A61F 2002/30143* (2013.01); *A61F 2002/30146* (2013.01); *A61F 2002/30148* (2013.01); *A61F 2002/30151* (2013.01); *A61F 2002/30153* (2013.01); *A61F 2002/30154* (2013.01); *A61F 2002/30171* (2013.01); *A61F 2002/30263* (2013.01); *A61F 2002/30273* (2013.01); *A61F 2002/30331* (2013.01); *A61F 2002/30943* (2013.01); *A61F 2002/30952* (2013.01); *A61F 2002/4495* (2013.01); *A61F 2250/0098* (2013.01); *A61F 2310/00011* (2013.01)

(58) Field of Classification Search
CPC .. A61F 2002/30148; A61F 2002/30151; A61F 2002/30153; A61F 2002/30154; A61F 2002/30171; A61F 2002/30263; A61F 2002/30273; A61F 2002/3028; G02F 1/1337
See application file for complete search history.

(56) References Cited

U.S. PATENT DOCUMENTS

| | | | |
|---|---|---|---|
| 6,149,688 A | 11/2000 | Brosnahan et al. | |
| 6,206,924 B1 | 3/2001 | Timm | |
| 6,723,126 B1 | 4/2004 | Berry | |
| 6,767,594 B1* | 7/2004 | Miroshin | G02B 5/3083 428/1.31 |
| 6,902,579 B2 | 6/2005 | Harms et al. | |
| 7,128,760 B2 | 10/2006 | Michelson | |
| 7,172,627 B2 | 2/2007 | Fiere et al. | |
| 7,217,293 B2 | 5/2007 | Branch, Jr. | |
| 7,637,950 B2 | 12/2009 | Baccelli et al. | |
| D619,255 S | 7/2010 | Richter et al. | |
| 7,799,079 B2 | 9/2010 | Hestad et al. | |
| D626,233 S | 10/2010 | Cipoletti et al. | |
| 7,850,731 B2 | 12/2010 | Brittan et al. | |
| 8,043,381 B2 | 10/2011 | Hestad et al. | |
| D653,757 S | 2/2012 | Binder | |
| 8,236,058 B2 | 8/2012 | Fabian et al. | |
| 8,425,576 B2 | 4/2013 | Anderson et al. | |
| D682,427 S | 5/2013 | Farris et al. | |
| D692,136 S | 10/2013 | Tyber | |
| 8,663,332 B1 | 3/2014 | To et al. | |
| 8,697,231 B2 | 4/2014 | Longepied et al. | |
| 8,740,983 B1 | 6/2014 | Arnold et al. | |
| D708,747 S | 7/2014 | Curran et al. | |
| D711,537 S | 8/2014 | Pimenta et al. | |
| 8,900,307 B2 | 12/2014 | Hawkins et al. | |
| 8,945,227 B2 | 2/2015 | Kirschman | |
| 9,005,291 B2 | 4/2015 | Loebl et al. | |
| D737,446 S | 8/2015 | Butler et al. | |
| 9,155,819 B2 | 10/2015 | Fonte et al. | |
| 9,186,257 B2 | 11/2015 | Geisler et al. | |
| D750,249 S | 2/2016 | Grimberg, Jr. et al. | |
| 9,271,836 B2 | 3/2016 | Pavento et al. | |
| 9,271,843 B2 | 3/2016 | Fabian et al. | |
| 9,308,076 B2 | 4/2016 | Ringeisen et al. | |
| 9,456,901 B2 | 10/2016 | Jones et al. | |
| 9,492,285 B2 | 11/2016 | Saidha et al. | |
| 9,566,163 B2 | 2/2017 | Suddaby et al. | |
| 9,662,225 B2 | 5/2017 | Pavento et al. | |
| D789,539 S | 6/2017 | Kleiner et al. | |
| 9,668,877 B2 | 6/2017 | Pavento et al. | |
| 9,872,781 B2 | 1/2018 | Pavento et al. | |
| D816,844 S | 5/2018 | Ricca et al. | |
| 9,962,269 B2 | 5/2018 | Jones et al. | |
| 10,045,797 B1 | 8/2018 | Walkenhorst et al. | |
| D833,012 S | 11/2018 | Jones et al. | |
| D833,611 S | 11/2018 | Jones et al. | |
| D833,612 S | 11/2018 | Jones et al. | |
| 10,130,488 B2 | 11/2018 | Saidha et al. | |
| D835,279 S | 12/2018 | Jones et al. | |
| D835,788 S | 12/2018 | Jones et al. | |
| D840,036 S | 2/2019 | Jones et al. | |
| 10,368,997 B2 | 8/2019 | Jones et al. | |
| 10,405,983 B2 | 9/2019 | Jones et al. | |
| 2002/0161444 A1 | 10/2002 | Choi | |
| 2003/0114936 A1 | 6/2003 | Sherwood et al. | |
| 2004/0243241 A1 | 12/2004 | Istephanous | |
| 2004/0258732 A1 | 12/2004 | Shikinami | |
| 2005/0049706 A1 | 3/2005 | Brodke et al. | |
| 2005/0101960 A1 | 5/2005 | Fiere et al. | |
| 2005/0113916 A1 | 5/2005 | Branch | |
| 2005/0129726 A1 | 6/2005 | Liebschner | |
| 2005/0159813 A1 | 7/2005 | Molz | |
| 2005/0251083 A1 | 11/2005 | Carr-Brendel et al. | |
| 2006/0147332 A1 | 7/2006 | Jones et al. | |
| 2006/0257817 A1 | 11/2006 | Shelton | |
| 2006/0259144 A1 | 11/2006 | Trieu | |
| 2006/0276925 A1 | 12/2006 | Lin et al. | |
| 2007/0073398 A1 | 3/2007 | Fabian et al. | |
| 2007/0142914 A1 | 6/2007 | Jones et al. | |
| 2007/0150068 A1* | 6/2007 | Dong | B22F 3/1146 623/22.32 |
| 2007/0233247 A1 | 10/2007 | Schwab | |
| 2007/0270858 A1 | 11/2007 | Trieu | |
| 2008/0161925 A1 | 7/2008 | Brittan et al. | |
| 2008/0161927 A1 | 7/2008 | Savage et al. | |
| 2008/0169585 A1 | 7/2008 | Zinniel | |
| 2008/0269903 A1 | 10/2008 | Francis et al. | |
| 2008/0294262 A1 | 11/2008 | Levieux | |
| 2008/0300634 A1 | 12/2008 | Gray | |
| 2008/0306596 A1 | 12/2008 | Jones et al. | |
| 2008/0306609 A1 | 12/2008 | Lee et al. | |
| 2009/0012529 A1 | 1/2009 | Blain et al. | |
| 2009/0037148 A1 | 2/2009 | Lin et al. | |
| 2009/0105831 A1 | 4/2009 | Jones et al. | |
| 2009/0182429 A1 | 7/2009 | Humphreys et al. | |
| 2009/0287214 A1 | 11/2009 | Yu | |
| 2009/0317278 A1 | 12/2009 | Kokubo | |
| 2009/0326580 A1 | 12/2009 | Anderson et al. | |
| 2010/0087925 A1 | 4/2010 | Kostuik et al. | |
| 2010/0100185 A1 | 4/2010 | Trieu et al. | |
| 2010/0145459 A1 | 6/2010 | McDonough et al. | |
| 2010/0234948 A1 | 9/2010 | Khoury et al. | |
| 2010/0286783 A1 | 11/2010 | Lechmann et al. | |
| 2011/0004307 A1 | 1/2011 | Ahn et al. | |
| 2011/0012280 A1 | 1/2011 | Deslauriers et al. | |
| 2011/0029084 A1 | 2/2011 | Milbocker et al. | |
| 2011/0029087 A1 | 2/2011 | Haider et al. | |
| 2011/0144764 A1 | 6/2011 | Bagga et al. | |
| 2011/0190892 A1 | 8/2011 | Kirschman | |
| 2011/0224796 A1 | 9/2011 | Weiland et al. | |
| 2011/0282392 A1 | 11/2011 | Murphy et al. | |
| 2012/0022653 A1 | 1/2012 | Kirschman | |
| 2012/0123546 A1 | 5/2012 | Medina | |
| 2012/0150299 A1 | 6/2012 | Ergun et al. | |
| 2012/0177939 A1 | 7/2012 | Longepied et al. | |
| 2012/0179258 A1 | 7/2012 | Glazer et al. | |
| 2012/0185047 A1 | 7/2012 | Wooley | |
| 2012/0215310 A1 | 8/2012 | Sharp et al. | |
| 2012/0215313 A1 | 8/2012 | Saidha et al. | |
| 2012/0303128 A1 | 11/2012 | Ullrich, Jr. et al. | |

(56) References Cited

U.S. PATENT DOCUMENTS

| | | |
|---|---|---|
| 2012/0312779 A1 | 12/2012 | Patterson et al. |
| 2012/0321878 A1* | 12/2012 | Landon .................. A61L 27/56 428/304.4 |
| 2013/0026492 A1* | 1/2013 | Khan .................. H01L 29/6603 257/77 |
| 2013/0039094 A1* | 2/2013 | Kolb ...................... B29C 41/24 362/618 |
| 2013/0060337 A1 | 3/2013 | Petersheim et al. |
| 2013/0073044 A1 | 3/2013 | Gamache |
| 2013/0218276 A1 | 8/2013 | Fiechter et al. |
| 2013/0238095 A1 | 9/2013 | Pavento et al. |
| 2013/0282126 A1 | 10/2013 | Saidha et al. |
| 2013/0310939 A1 | 11/2013 | Fabian et al. |
| 2013/0325129 A1 | 12/2013 | Huang |
| 2014/0012382 A1 | 1/2014 | Doty |
| 2014/0012384 A1 | 1/2014 | Kana et al. |
| 2014/0037873 A1* | 2/2014 | Cheung ............... E04B 1/34384 428/34.1 |
| 2014/0046447 A1 | 2/2014 | Dunworth et al. |
| 2014/0046448 A1 | 2/2014 | Kana et al. |
| 2014/0107786 A1 | 4/2014 | Geisler et al. |
| 2014/0121776 A1 | 5/2014 | Hunt |
| 2014/0277482 A1 | 9/2014 | Gfeller et al. |
| 2015/0005885 A1 | 1/2015 | Zhang et al. |
| 2015/0025635 A1 | 1/2015 | Laubert |
| 2015/0093283 A1 | 4/2015 | Miller et al. |
| 2015/0100126 A1 | 4/2015 | Melkent et al. |
| 2015/0360421 A1 | 12/2015 | Burhop et al. |
| 2016/0000574 A9 | 1/2016 | Fabian et al. |
| 2016/0022431 A1 | 1/2016 | Wickham |
| 2016/0027425 A1 | 1/2016 | Cook et al. |
| 2016/0038301 A1 | 2/2016 | Wickham |
| 2016/0058480 A1 | 3/2016 | Laubert et al. |
| 2016/0085882 A1 | 3/2016 | Li et al. |
| 2016/0113775 A1 | 4/2016 | Willis et al. |
| 2016/0166284 A1 | 6/2016 | Hacking et al. |
| 2016/0184103 A1* | 6/2016 | Fonte ...................... A61L 27/56 623/23.5 |
| 2016/0199193 A1 | 7/2016 | Willis et al. |
| 2016/0206440 A1 | 7/2016 | DeRidder et al. |
| 2016/0235546 A1 | 8/2016 | Cheng et al. |
| 2016/0270931 A1 | 9/2016 | Trieu |
| 2017/0014235 A1 | 1/2017 | Jones et al. |
| 2017/0020685 A1 | 1/2017 | Geisler et al. |
| 2017/0042698 A1 | 2/2017 | Saidha et al. |
| 2017/0095337 A1 | 4/2017 | Pasini et al. |
| 2017/0119538 A1 | 5/2017 | Baynham |
| 2017/0312096 A1 | 11/2017 | Liu et al. |
| 2017/0325966 A1 | 11/2017 | Capote et al. |
| 2017/0348114 A1 | 12/2017 | Jones et al. |
| 2017/0367845 A1 | 12/2017 | Eisen et al. |
| 2018/0140427 A1 | 5/2018 | Conway et al. |
| 2018/0221156 A1 | 8/2018 | Jones et al. |
| 2018/0228570 A1* | 8/2018 | Jones .................. A61F 2/30942 |
| 2018/0228612 A1* | 8/2018 | Jones .................... B33Y 50/00 |
| 2018/0228613 A1 | 8/2018 | Jones et al. |
| 2018/0243094 A1 | 8/2018 | Jones et al. |
| 2018/0243097 A1 | 8/2018 | Jones et al. |
| 2018/0280139 A1 | 10/2018 | Jones et al. |
| 2018/0280140 A1 | 10/2018 | Jones et al. |
| 2018/0280141 A1 | 10/2018 | Jones et al. |
| 2018/0280144 A1 | 10/2018 | Jones et al. |
| 2018/0280145 A1* | 10/2018 | Jones .................... A61F 2/3094 |
| 2018/0296350 A1 | 10/2018 | Hamzey et al. |
| 2018/0318099 A1 | 11/2018 | Altarac et al. |
| 2018/0318100 A1 | 11/2018 | Altarac et al. |
| 2018/0368990 A1 | 12/2018 | Saidha et al. |
| 2018/0368992 A1 | 12/2018 | Zink et al. |
| 2019/0133778 A1 | 5/2019 | Johnston |
| 2019/0133783 A1 | 5/2019 | Unger et al. |
| 2019/0150910 A1 | 5/2019 | Jones et al. |
| 2019/0209215 A1 | 7/2019 | Baynham et al. |
| 2019/0250438 A1* | 8/2019 | Oton ...................... G02F 1/137 |
| 2019/0343638 A1 | 11/2019 | Jones et al. |
| 2020/0000595 A1 | 1/2020 | Jones et al. |
| 2020/0038069 A1 | 2/2020 | Jones et al. |
| 2020/0138595 A1 | 5/2020 | Shoshtaev et al. |
| 2020/0281736 A1 | 9/2020 | Milz et al. |

FOREIGN PATENT DOCUMENTS

| | | | |
|---|---|---|---|
| EP | 2647453 A2 * | 10/2013 | ......... A61F 2/30942 |
| EP | 1887954 B1 | 9/2014 | |
| WO | 1999033641 A1 | 7/1999 | |
| WO | WO-0217823 A1 | 3/2002 | |
| WO | WO-2009091627 A1 | 7/2009 | |
| WO | WO-2014160389 A1 | 10/2014 | |
| WO | WO-2014172495 A2 | 10/2014 | |
| WO | 2015164982 A1 | 11/2015 | |
| WO | 2016061148 A1 | 4/2016 | |
| WO | WO-2016130878 A1 | 8/2016 | |
| WO | 2017214114 A1 | 12/2017 | |
| WO | 2018152077 A1 | 8/2018 | |
| WO | 2018156905 A1 | 8/2018 | |
| WO | 2018182834 A1 | 10/2018 | |
| WO | 2018183809 A1 | 10/2018 | |
| WO | 2020023938 A1 | 1/2020 | |

OTHER PUBLICATIONS

Babaee S., et al., "Mechanical properties of open-cell rhombic dodecahedron cellular structures," Acta Materialia, vol. 60:2873-2885 (2012).

European Search Report, 17810838.7, dated Dec. 19, 2019, 8 pages.

Hoffmann, W. et al., "Rapid prototyped porous nickel-titanium scaffolds as bone substitutes," Journal of Tissue Enngineering, vol. 5:1-14 (2014).

International Preliminary Report on Patentability, PCT/US2017/36111, dated Jun. 27, 2018, 26 pages.

International Preliminary Report on Patentability, PCT/US2018/017919, dated Aug. 20, 2019, 11 pages.

International Preliminary Report on Patentability, PCT/US2018/019437, dated Aug. 27, 2019, 16 pages.

International Search Report and Written Opinion, PCT /US2017/36111, dated Nov. 6, 2017, 10 pages.

International Search Report and Written Opinion, PCT/US2018/014720, dated Jun. 1, 2018, 13 pages.

International Search Report and Written Opinion, PCT/US2018/019437, dated Jun. 28, 2018, 19 pages.

International Search Report and Written Opinion, PCT/US2018/025351, dated Jun. 8, 2018, 14 pages.

International Search Report and Written Opinion, PCT/US2019/043803, dated Nov. 7, 2019, 11 pages.

International Search Report and Written Opinion of the International Searching Authority received in corresponding PCT Application, PCT/US2018/017919, dated Jun. 6, 2018, 14 pages.

Nouri, A., "Titanium foam scaffolds for dental applications," Metallic Foam Bone, Chapter 5: 130-160 (2017).

Zhang,X., et al., "Additively Manufactured Scaffolds for Bone Tissue Engineering and the Prediction of their Mechanical Behavior: A Review," Materials, 10(10): 1-28 (2017).

Chandran R.; "Optimization of Support Structures in Additive Manufacturing Process", Dissertation, University of Miami, 2016 (Year:2016).

Leary M., et al.; "Optimal topology for additive manufacture: A method for enabling additive manufacture of support-free optimal structures", Materials and Design, 2014, vol. 63, p. 678-690 (Year: 2014).

Strano G., et al.; "A new approach to the design and optimization of support structures in additive manufacturing", Int. J. Adv Manufacturing Technology, 2013, 66, p. 1247-1254 (Year: 2013).

Stryker, "Tritanium PI Cage", Technical Data Sheet, https://www.stryker.com/builttofuse/; retrieved from wayback machine on Apr. 23, 2021; date Jun. 21, 2016.

U.S. Appl. No. 15/876,695, filed Jan. 22, 2018, Christopher L. Jones.

U.S. Appl. No. 16/251,383, filed Jan. 18, 2019, Christopher L. Jones.

(56) References Cited

OTHER PUBLICATIONS

U.S. Appl. No. 16/518,281, filed Jul. 22, 2019, Christopher L. Jones.
U.S. Appl. No. 15/876,793, filed Jan. 22, 2018, Christopher L. Jones.
U.S. Appl. No. 15/876,903, filed Jan. 22, 2018, Christopher L. Jones.
U.S. Appl. No. 15/877,002, filed Jan. 22, 2018, Christopher L. Jones.
U.S. Appl. No. 16/565,321, filed Sep. 9, 2019, Christopher L. Jones.
U.S. Appl. No. 15/895,228, filed Feb. 13, 2018, Christopher L. Jones.
U.S. Appl. No. 15/895,201, filed Feb. 13, 2018, Christopher L. Jones.
U.S. Appl. No. 15/903,667, filed Feb. 23, 2018, Christopher L. Jones.
U.S. Appl. No. 16/523,962, filed Jul. 26, 2019, Christopher L. Jones.
U.S. Appl. No. 16/744,103, filed Jan. 15, 2020, Christopher L. Jones.
U.S. Appl. No. 15/903,648, filed Feb. 23, 2018, Christopher L. Jones.

* cited by examiner

US 11,253,368 B2

METHODS OF DESIGNING HIGH X-RAY LUCENCY LATTICE STRUCTURES

CROSS REFERENCE TO RELATED APPLICATIONS

This application claims the benefit of U.S. Provisional Patent Application No. 62/458,714 filed Feb. 14, 2017, U.S. Provisional Patent Application No. 62/480,383 filed Apr. 1, 2017, U.S. Provisional Patent Application No. 62/480,385 filed Apr. 1, 2017, and U.S. Provisional Patent Application No. 62/619,260 filed Jan. 19, 2018, which are hereby incorporated by reference in their entirety.

FIELD OF THE INVENTION

The present invention relates to biocompatible lattice structures and, in particular, to lattice structures with increased lucency in a desired direction with respect to x-ray imaging and to markers with a variable radiolucency or radiopacity.

BACKGROUND OF THE INVENTION

Medical implants can be constructed using a wide range of materials, including metallic materials, Polyether ether ketone (hereinafter "PEEK"), ceramic materials and various other materials or composites thereof. There are competing priorities when selecting a material for an implant in order for the implant to pass regulatory testing. Some priorities when designing an implant could include strength, stiffness, fatigue resistance, radiolucency, and bioactivity. Therefore, when designing an implant to meet regulatory standards, oftentimes, some compromises have to be made to meet all testing requirements.

BRIEF SUMMARY OF THE INVENTION

The biocompatible lattice structures disclosed herein, in some embodiments, have an increased lucency. Also disclosed herein is a method of designing lattice structure with an increased lucency. Some embodiments also include markers with a varied radiolucency based on the viewing angle.

The lattice structures disclosed herein can have increased lucency over other structures comprising similar materials, porosities, densities and/or volumetric densities. While the embodiments expressed herein are directed towards medical implants, the structures disclosed could also be beneficial when used in medical devices outside of the body that require a level of lucency or in devices outside of the medical field.

When implants comprise lattice structures or scaffolds for tissue growth, it is desirable to be able to monitor the healing process within the implant. In many cases, it is beneficial to be able to monitor the level of bone ingrowth at certain time intervals after implantation. Generally, imaging of the surgical site is completed using x-ray imaging, however, other types of imaging may also be used.

Many biocompatible structures, including lattice or porous structures, comprise a material generally considered to have radiopaque properties. It was discovered that materials that are generally considered to be radiopaque often only become fully radiopaque when a certain bulk thickness is reached. In this case, bulk thickness means the actual thickness of a structure in a certain direction when any voids are removed. For instance, a structure with a uniform 50% volumetric density and a thickness of two inches would have a bulk thickness of one inch in that direction and a lattice with a 25% volumetric density and a thickness of two inches would have a bulk thickness of a half inch in that direction.

The elastic modulus of lattice structures may be modified by changing the volumetric density of the structure so that increasing the volumetric density generally increases the bulk elastic modulus and vice versa. Depending on the particular elastic modulus needed in an application, the need for radiolucency can be at odds with the need for an increased elastic modulus. Therefore, the lattice structures and methods of design disclosed herein are particularly useful in implants where there is a need for a lattice structure with increased lucency at all volumetric density levels.

DETAILED DESCRIPTION OF THE INVENTION

Figure 1:
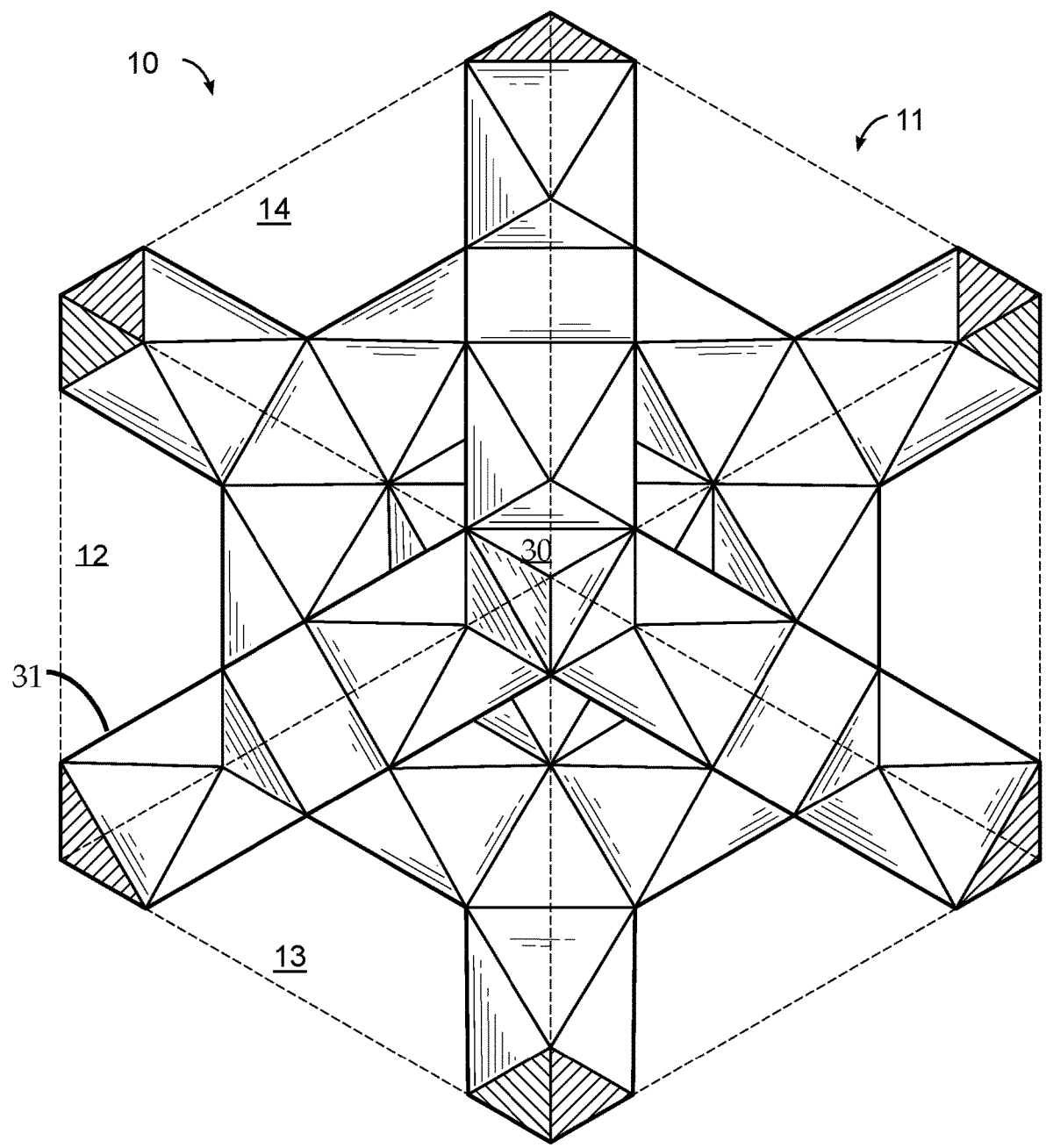
FIG. 1 is an isometric view of a single modified rhombic dodecahedron unit cell containing a full modified rhombic dodecahedron structure along with radial struts that comprise portions of adjacent unit cells.

In many situations, it is desirable to use an implant that is capable of bone attachment or osteointegration over time. It is also desirable in many situations to use an implant that is capable of attachment or integration with living tissue. Examples of implants where attachment to bone or osteointegration is beneficial include, but are not limited to, cervical, lumbar, and thoracic interbody fusion implants, vertebral body replacements, osteotomy wedges, dental implants, bone stems, acetabular cups, cranio-facial plating, bone replacement and fracture plating. In many applications, it is also desirable to stress new bone growth to increase its strength. According to Wolff's law, bone will adapt to stresses placed on it so that bone under stress will grow stronger and bone that isn't stressed will become weaker.

In some aspects, the systems and methods described herein can be directed toward implants that are configured for osteointegration and stimulating adequately stressed new bone growth. Many of the exemplary implants of the present invention are particularly useful for use in situations where it is desirable to have strong bone attachment and/or bone growth throughout the body of an implant. Whether bone growth is desired only for attachment or throughout an implant, the present invention incorporates a unique lattice structure that can provide mechanical spacing, a scaffold to support new bone growth and a modulus of elasticity that allows new bone growth to be loaded with physiological forces. As a result, the present invention provides implants that grow stronger and healthier bone for more secure attachment and/or for a stronger bone after the implant osteointegrates.

The exemplary embodiments of the invention presented can be comprised, in whole or in part, of a lattice. A lattice, as used herein, refers to a three-dimensional material with one or more interconnected openings that allow a fluid to communicate from one location to another location through an opening. A three-dimensional material refers to a material that fills a three-dimensional space (i.e. has height, width and length). Lattices can be constructed by many means, including repeating various geometric shapes or repeating random shapes to accomplish a material with interconnected openings. An opening in a lattice is any area within the bounds of the three-dimensional material that is devoid of that material. Therefore, within the three-dimensional boundaries of a lattice, there is a volume of material and a volume that is devoid of that material.

The material that provides the structure of the lattice is referred to as the primary material. The structure of a lattice does not need to provide structural support for any purpose, but rather refers to the configuration of the openings and interconnections that comprise the lattice. An opening in a lattice may be empty, filled with a gaseous fluid, filled with a liquid fluid, filled with a solid or partially filled with a fluid and/or solid. Interconnections, with respect to openings, refer to areas devoid of the primary material and that link at least two locations together. Interconnections may be configured to allow a fluid to pass from one location to another location.

A lattice can be defined by its volumetric density, meaning the ratio between the volume of the primary material and the volume of voids presented as a percentage for a given three-dimensional material. The volume of voids is the difference between the volume of the bounds of the three-dimensional material and the volume of the primary material. The volume of voids can comprise of the volume of the openings, the volume of the interconnections and/or the volume of another material present. For example, a lattice with a 30% volumetric density would be comprised of 30% primary material by volume and 70% voids by volume over a certain volume. A lattice with a 90% volumetric density would be comprised of 90% primary material by volume and 10% voids by volume over a certain volume. In three-dimensional materials with a volumetric density of less than 50%, the volume of the primary material is less than the volume of voids. While the volumetric density refers to the volume of voids, the voids do not need to remain void and can be filled, in whole or in part, with a fluid or solid prior to, during or after implantation.

Lattices comprised of repeating geometric patterns can be described using the characteristics of a repeating unit cell. A unit cell in a repeating geometric lattice is a three-dimensional shape capable of being repeated to form a lattice. A repeating unit cell can refer to multiple identical unit cells that are repeated over a lattice structure or a pattern through all or a portion of a lattice structure. Each unit cell is comprised of a certain volume of primary material and a certain void volume, or in other words, a spot volumetric density. The spot volumetric density may cover as few as a partial unit cell or a plurality of unit cells. In many situations, the spot volumetric density will be consistent with the material's volumetric density, but there are situations where it could be desirable to locally increase or decrease the spot volumetric density.

Unit cells can be constructed in numerous volumetric shapes containing various types of structures. Unit cells can be bound by a defined volume of space to constrict the size of the lattice structure or other type of structure within the unit cell. In some embodiments, unit cells can be bound by volumetric shapes, including but not limited to, a cubic volume, a cuboid volume, a hexahedron volume or an amorphous volume. The unit cell volume of space can be defined based on a number of faces that meet at corners. In examples where the unit cell volume is a cubic, cuboid or hexahedron volume, the unit cell volume can have six faces and eight corners, where the corners are defined by the location where three faces meet. Unit cells may be interconnected in some or all areas, not interconnected in some or all areas, of a uniform size in some or all areas or of a nonuniform size in some or all areas. In some embodiments disclosed herein that use a repeating geometric pattern, the unit cells can be defined by a number of struts defining the edges of the unit cell and joined at nodes about the unit cell. Unit cells so defined can share certain struts among more than one unit cell, so that two adjacent unit cells may share a common planar wall defined by struts common to both cells. In some embodiments disclosed herein that use a repeating geometric pattern, the unit cells can be defined by a node and a number of struts extending radially from that node.

While the present application uses volumetric density to describe exemplary embodiments, it is also possible to describe them using other metrics, including but not limited to cell size, strut size or stiffness. Cell size may be defined using multiple methods, including but not limited to cell diameter, cell width, cell height and cell volume. Strut size may be defined using multiple methods, including but not limited to strut length and strut diameter.

Repeating geometric patterns are beneficial for use in lattice structures contained in implants because they can provide predictable characteristics. Many repeating geometric shapes may be used as the unit cell of a lattice, including but are not limited to, rhombic dodecahedron, diamond, dodecahedron, square, pentagonal, hexagonal, octagonal, sctet struts, trunic octa, diagonal struts, other known geometric structures, and rounded, reinforced, weakened, or simplified versions of each geometry.

Lattices may also be included in implants as a structural component or a nonstructural component. Lattices used in structural applications may be referred to herein as structural lattices, load-bearing lattices or stressed lattices. In some instances, structural lattices, load-bearing lattices or stressed lattices may be simply referred to as a lattice. Repeating geometric shaped unit cells, particularly the rhombic dodecahedron, are well suited, in theory, for use in structural lattices because of their strength to weight ratio. To increase the actual strength and fatigue resistance of a rhombic dodecahedron lattice, the present invention, in some embodiments, includes a modified strut comprised of triangular segments, rather than using a strut with a rectangular or circular cross section. Some embodiments herein also modify the angles defining the rhombic faces of a rhombic dodecahedron to change the lattice's elastic modulus and fatigue resistance. The use of triangular segments provides a lattice with highly predictable printed properties that approach the theoretical strength values for a rhombic dodecahedron lattice.

In structural lattice applications, the strength and elastic modulus of the lattice can be approximated by the volumetric density. When the volumetric density increases, the strength and the elastic modulus increases. Compared to other porous structures, the lattice of the present invention has a higher strength and elastic modulus for a given volumetric density because of its ability to use the high strength to weight benefits of a rhombic dodecahedron, modified rhombic dodecahedron or radial dodeca-rhombus unit cell.

When configured to provide support for bone or tissue growth, a lattice may be referred to as a scaffold. Lattices can be configured to support bone or tissue growth by controlling the size of the openings and interconnections disposed within the three-dimensional material. A scaffold, if used on the surface of an implant, may provide an osteointegration surface that allows adjacent bone to attach to the implant. A scaffold may also be configured to provide a path that allows bone to grow further than a mere surface attachment. Scaffolds intended for surface attachment are referred to herein as surface scaffolds. A surface scaffold may be one or more unit cells deep, but does not extend throughout the volume of an implant. Scaffolds intended to support in-growth beyond mere surface attachment are referred to herein as bulk scaffolds. Scaffolds may also be included in implants as a structural component or a nonstructural component. Scaffolds used in structural applications may be referred to herein as structural scaffolds, load-bearing scaffolds or stressed scaffolds. In some instances, structural scaffolds, load-bearing scaffolds or stressed scaffolds may be simply referred to as a scaffold. In some instances, the use of the term scaffold may refer to a material configured to provide support for bone or tissue growth, where the material is not a lattice.

The scaffolds described herein can be used to promote the attachment or in-growth of various types of tissue found in living beings. As noted earlier, some embodiments of the scaffold are configured to promote bone attachment and in-growth. The scaffolds can also be configured to promote attachment of in-growth of other areas of tissue, such as fibrous tissue. In some embodiments, the scaffold can be configured to promote the attachment or in-growth of multiple types of tissue. Some embodiments of the scaffolds are configured to be implanted near or abutting living tissue. Near living tissue includes situations where other layers, materials or coatings are located between a scaffold and any living tissue.

In some embodiments, the present invention uses bulk scaffolds with openings and interconnections that are larger than those known in the art. Osteons can range in diameter from about 100 μm and it is theorized that a bundle of osteons would provide the strongest form of new bone growth. Bone is considered fully solid when it has a diameter of greater than 3 mm so it is theorized that a bundle of osteons with a diameter equaling approximately half of that value would provide significant strength when grown within a scaffold. It is also theorized that osteons may grow in irregular shapes so that the cross-sectional area of an osteon could predict its strength. A cylindrical osteon growth with a 3 mm diameter has a cross-sectional area of approximately 7 square mm and a cylindrical osteon with a 1.5 mm diameter has a cross-sectional area of 1.8 square mm. It is theorized that an osteon of an irregular shape with a cross-sectional area of at least 1.8 square millimeters could provide a significant strength advantage when grown in a scaffold.

Most skilled in the art would indicate that pores or openings with a diameter or width between 300 μm to 900 μm, with a pore side of 600 μm being ideal, provide the best scaffold for bone growth. Instead, some embodiments of the present invention include openings and interconnections with a diameter or width on the order of 1.0 to 15.0 times the known range, with the known range being 300 μm to 900 μm, resulting in openings from 0.07 mm² up to 145 mm² cross sectional area for bone growth. In some examples, pores or openings with a diameter or width between and including 100 μm to 300 μm could be beneficial. Some examples include openings and interconnections with a diameter on the order of 1.0 to 5.0 times the known range. It has been at least theorized that the use of much larger openings and interconnections than those known in the art will allow full osteons and solid bone tissue to form throughout the bulk scaffold, allowing the vascularization of new, loadable bone growth. In some examples, these pores may be 3 mm in diameter or approximately 7 mm² in cross sectional area. In other examples, the pores are approximately 1.5 mm in diameter or approximately 1.75 mm² in cross sectional area. The use of only the smaller diameter openings and interconnections known in the art are theorized to limit the penetration of new bone growth into a bulk scaffold because the smaller diameter openings restrict the ability of vascularization throughout the bulk scaffold.

A related structure to a lattice is a closed cell material. A closed cell material is similar to a lattice, in that it has openings contained within the bounds of a three-dimensional material, however, closed cell materials generally lack interconnections between locations through openings or other pores. A closed cell structure may be accomplished using multiple methods, including the filling of certain cells or through the use of solid walls between the struts of unit cells. A closed cell structure can also be referred to as a cellular structure. It is possible to have a material that is a lattice in one portion and a closed cell material in another. It is also possible to have a closed cell material that is a lattice with respect to only certain interconnections between openings or vice versa. While the focus of the present disclosure is on lattices, the structures and methods disclosed herein can be easily adapted for use on closed cell structures within the inventive concept.

The lattice used in the present invention can be produced from a range of materials and processes. When used as a scaffold for bone growth, it is desirable for the lattice to be made of a biocompatible material that allows for bone attachment, either to the material directly or through the application of a bioactive surface treatment. In one example, the scaffold is comprised of an implantable metal. Implantable metals include, but are not limited to, zirconium, stainless steel (316 & 316L), tantalum, nitinol, cobalt chromium alloys, titanium and tungsten, and alloys thereof. Scaffolds comprised of an implantable metal may be produced using an additive metal fabrication or 3D printing process. Appropriate production processes include, but are not limited to, direct metal laser sintering, selective laser sintering, selective laser melting, electron beam melting, laminated object manufacturing and directed energy deposition.

In another example, the lattice of the present invention is comprised of an implantable metal with a bioactive coating. Bioactive coatings include, but are not limited to, coatings to accelerate bone growth, anti-thrombogenic coatings, anti-microbial coatings, hydrophobic or hydrophilic coatings, and hemophobic, superhemophobic, or hemophilic coatings. Coatings that accelerate bone growth include, but are not limited to, calcium phosphate, hydroxyapatite ("HA"), silicate glass, stem cell derivatives, bone morphogenic proteins, titanium plasma spray, titanium beads and titanium mesh. Anti-thrombogenic coatings include, but are not limited to, low molecular weight fluoro-oligomers. Anti-microbial coatings include, but are not limited to, silver, organosilane compounds, iodine and silicon-nitride. Superhemophobic coatings include fluorinated nanotubes.

In another example, the lattice is made from a titanium alloy with an optional bioactive coating. In particular, Ti6Al4V ELI wrought (American Society for Testing and Materials ("ASTM") F136) is a particularly well-suited titanium alloy for scaffolds. While Ti6Al4V ELI wrought is the industry standard titanium alloy used for medical purposes, other titanium alloys, including but not limited to, unalloyed titanium (ASTM F67), Ti6Al4V standard grade (ASTM F1472), Ti6Al7Nb wrought (ASTM 1295), Ti5Al2.5Fe wrought (British Standards Association/International Standard Organization Part 10), CP and Ti6Al4V standard grade powders (ASTM F1580), Ti13Nb13Zr wrought (ASTM F1713), the lower modulus Ti-24Nb-4Zr-8Sn and Ti12Mo6Zr2Fe wrought (ASTM F1813) can be appropriate for various embodiments of the present invention.

Titanium alloys are an appropriate material for scaffolds because they are biocompatible and allow for bone attachment. Various surface treatments can be done to titanium alloys to increase or decrease the level of bone attachment. Bone will attach to even polished titanium, but titanium with a surface texture allows for greater bone attachment. Methods of increasing bone attachment to titanium may be produced through a forging or milling process, sandblasting, acid etching, and the use of a bioactive coating. Titanium parts produced with an additive metal fabrication or 3D printing process, such as direct metal laser sintering, can be treated with an acid bath to reduce surface stress risers, normalize surface topography, and improve surface oxide layer, while maintaining surface roughness and porosity to promote bone attachment.

Additionally, Titanium or other alloys may be treated with heparin, heparin sulfate (HS), glycosaminoglycans (GAG), chondroitin-4-sulphate (C4S), chondroitin-6-sulphate (C6S), hyaluronan (HY), and other proteoglycans with or without an aqueous calcium solution. Such treatment may occur while the material is in its pre-manufacturing form (often powder) or subsequent to manufacture of the structure.

While a range of structures, materials, surface treatments and coatings have been described, it is believed that a lattice using a repeating modified rhombic dodecahedron (hereinafter "MRDD") unit cell can present a preferable combination of stiffness, strength, fatigue resistance, and conditions for bone ingrowth. In some embodiments, the repeating MRDD lattice is comprised of titanium or a titanium alloy. A generic rhombic dodecahedron (hereinafter "RDD"), by definition, has twelve sides in the shape of rhombuses. When repeated in a lattice, an RDD unit cell is comprised of twenty four struts that meet at fourteen vertices. The twenty four struts define the twelve planar faces of the structure. An opening or interconnection is disposed at the center of each planar face, allowing communication from inside the unit cell to outside the unit cell.

Figure 2:
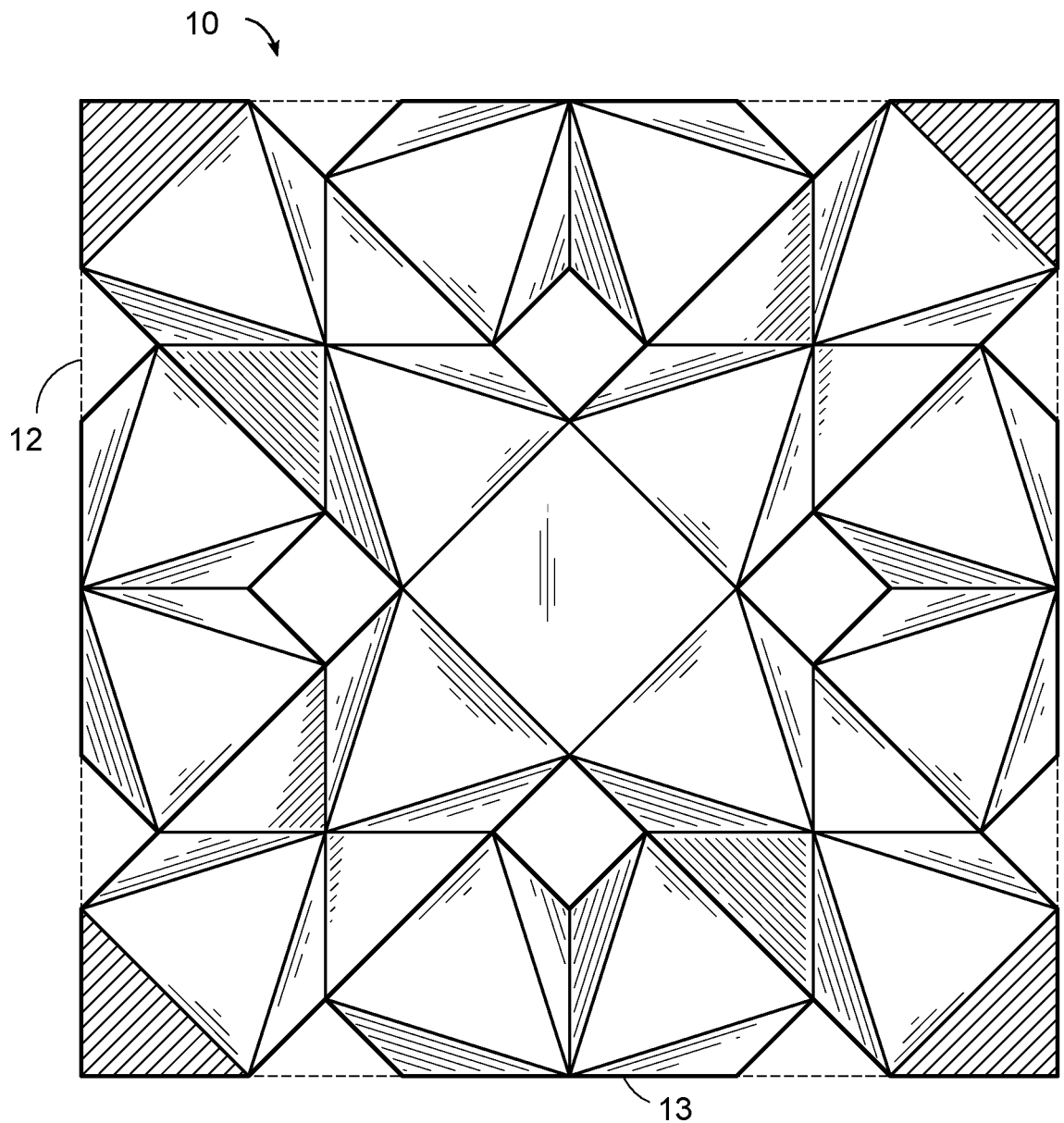
FIG. 2 is a side view of a single modified rhombic dodecahedron unit cell showing the configuration of interconnections when viewed from a lateral direction.

An example of the MRDD unit cell 10 used in the present invention is shown in FIGS. 1-5. FIG. 1 illustrates an isometric view of a single MRDD unit cell 10 containing a full MRDD structure along with radial struts 31 that comprise portions of adjacent unit cells. FIG. 2 is a side view of a single MRDD unit cell 10 showing the configuration of interconnections when viewed from a lateral direction. A top or bottom view of the MRDD unit cell 10 would be substantially the same as the side view depicted in FIG. 2. The MRDD unit cell 10 differs in both structural characteristics and method of design from generic RDD shapes. A generic RDD is comprised of twelve faces where each face is an identical rhombus with an acute angle of 70.5 degrees and an obtuse angle of 109.5 degrees. The shape of the rhombus faces in a generic RDD do not change if the size of the unit cell or the diameter of the struts are changed because the struts are indexed based on their axis and each pass through the center of the fourteen nodes or vertices.

In some embodiments of the MRDD, each node 30 is contained within a fixed volume that defines its bounds and provides a fixed point in space for the distal ends of the struts. The fixed volume containing the MRDD or a sub-unit cell of the MRDD can comprise of various shapes, including but not limited to, a cubic, cuboid, hexahedron or amorphous volume. Some examples use a fixed volume with six faces and eight corners defined by locations where three faces meet. The orientation of the struts 31 can be based on the center of a node face at its proximate end and the nearest corner of the volume to that node face on its distal end. Each node 30 is preferably an octahedron, more specifically a square bipyramid (i.e., a pyramid and inverted pyramid joined on a horizontal plane). Each node 30, when centrally located in a cuboid volume, more preferably comprises a square plane parallel to a face of the cuboid volume and six vertices. Each node 30 is oriented so that each of the six vertices are positioned at their closest possible location to each of the six faces of the cuboid volume. As used herein, the term "centrally located," with regards to the node's location within a volume refers to positioning the node at a location substantially equidistant from opposing walls of the volume. In some embodiments, the node 30 can have a volumetric density of 100%. In other embodiments, the node 30 can have a volumetric density of less than 100%. Each face of the square bipyramid node 30 can be triangular and each face can provide a connection point for a strut 31.

The struts 31 can also be octahedrons, comprising an elongate portion of six substantially similar elongate faces and two end faces. The elongate faces can be isosceles triangles with a first internal angle, angle A, and a second internal angle, angle B, where angle B is greater than angle A. The end faces can be substantially similar isosceles triangles to one another with a first internal angle, angle C, and a second internal angle, angle D, where angle D is greater than angle C. Preferably, angle C is greater than angle A.

The strut direction of each strut is a line or vector defining the orientation of a strut and it can be orthogonal or non-orthogonal relative to the planar surface of each node face. In the MRDD and radial dodeca-rhombus structures disclosed herein, the strut direction can be determined using a line extending between the center of the strut end faces, the center of mass along the strut or an external edge or face of the elongate portion of the strut. When defining a strut direction using a line extending between the center of the strut end faces, the line is generally parallel to the bottom face or edge of the strut. When defining a strut direction using a line extending along the center of mass of the strut, the line can be nonparallel to the bottom face or edge of the strut. The octahedron nodes of the MRDD can be scaled to increase or decrease volumetric density by changing the origin point and size of the struts. The distal ends of the struts, however, are locked at the fixed volume corners formed about each node so that their angle relative to each node face changes as the volumetric density changes. Even as the volumetric density of an MRDD unit cell changes, the dimensions of the fixed volume formed about each node does not change. In FIG. 1, dashed lines are drawn between the corners of the MRDD unit cell 10 to show the cube 11 that defines its bounds. In the MRDD unit cell in FIG. 1, the height 12, width 13 and depth 14 of the unit cell are substantially the same, making the area defined by the cube 11.

In some embodiments, the strut direction of a strut 31 can intersect the center of the node and the corner of the cuboid volume nearest to the node face where the strut 31 is fixed. In some embodiments, the strut direction of a strut 31 can intersect just the corner of the cuboid volume nearest to the node face where the strut is fixed. In some embodiments, a reference plane defined by a cuboid or hexahedron face is used to describe the strut direction of a strut. When the strut direction of a strut is defined based on a reference plane, it can be between 0 degrees and 90 degrees from the reference plane. When the strut direction of a strut is defined based on a reference plane, it is preferably eight degrees to 30 degrees from the reference plane.

By indexing the strut orientation to a variable node face on one end and a fixed point on its distal end, the resulting MRDD unit cell can allow rhombus shaped faces with a smaller acute angle and larger obtuse angle than a generic RDD. The rhombus shaped faces of the MRDD can have two substantially similar opposing acute angles and two substantially similar opposing obtuse angles. In some embodiments, the acute angles are less than 70.5 degrees and the obtuse angles are greater than 109.5 degrees. In some embodiments, the acute angles are between 0 degrees and 55 degrees and the obtuse angles are between 125 degrees and 180 degrees. In some embodiments, the acute angles are between 8 degrees and 60 degrees and the obtuse angles are between 120 degrees and 172 degrees. The reduction in the acute angles increases fatigue resistance for loads oriented across the obtuse angle corner to far obtuse angle corner. The reduction in the acute angles and increase in obtuse angles also orients the struts to increase the MRDD's strength in shear and increases the fatigue resistance. By changing the rhombus corner angles from a generic RDD, shear loads pass substantially in the axial direction of some struts, increasing the shear strength. Changing the rhombus corner angles from a generic RDD also reduces overall deflection caused by compressive loads, increasing the fatigue strength by resisting deflection under load.

Figure 3:
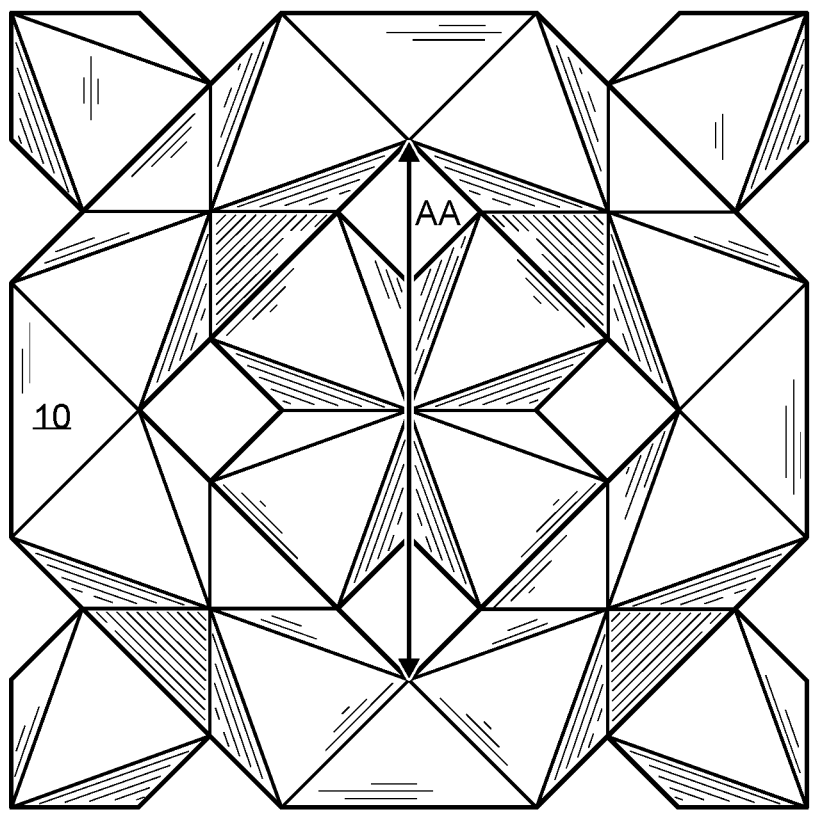
FIG. 3 is a side view of a single modified rhombic dodecahedron unit cell where the central void is being measured using the longest dimension method.
Figure 4:
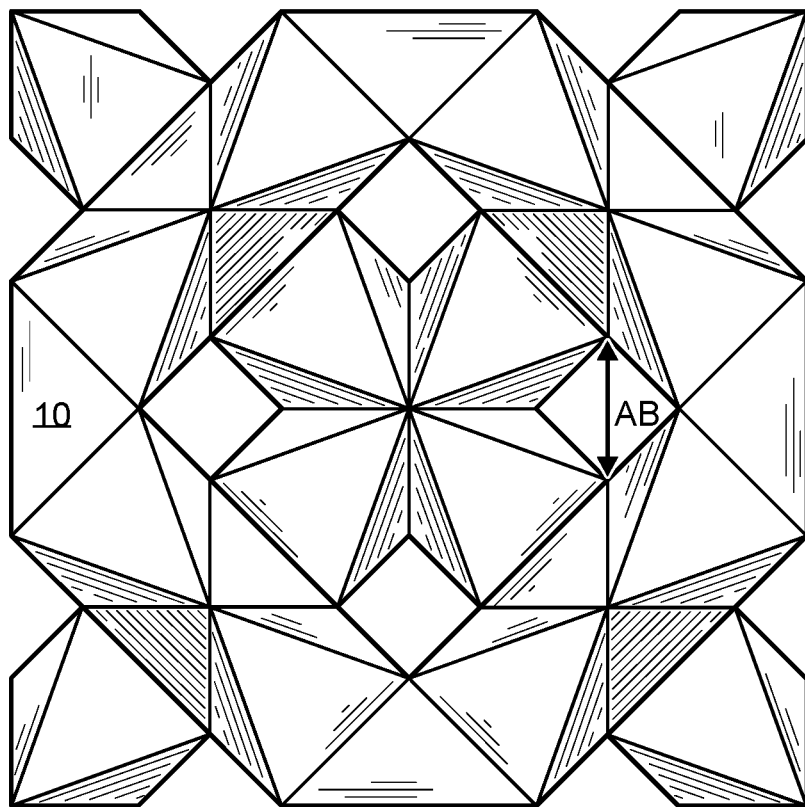
FIG. 4 is a side view of a single modified rhombic dodecahedron unit cell where an interconnection is being measured using the longest dimension method.

When placed towards the center of a lattice structure, the twelve interconnections of a unit cell 30 connect to twelve different adjacent unit cells, providing continuous paths through the lattice. The size of the central void and interconnections in the MRDD may be defined using the longest dimension method as described herein. Using the longest dimension method, the central void can be defined by taking a measurement of the longest dimension as demonstrated in FIG. 3. In FIG. 3, the longest dimension is labeled as distance AA. The distance AA can be taken in the vertical or horizontal directions (where the directions reference the directions on the page) and would be substantially the same in this example. The interconnections may be defined by their longest measurement when viewed from a side, top or bottom of a unit cell. In FIG. 4, the longest dimension is labeled as distance AB. The distance AB can be taken in the vertical or horizontal directions (where the directions reference the directions on the page). The view in FIG. 4 is a lateral view, however, in this example the unit cell will appear substantially the same when viewed from the top or bottom.

Figure 5:
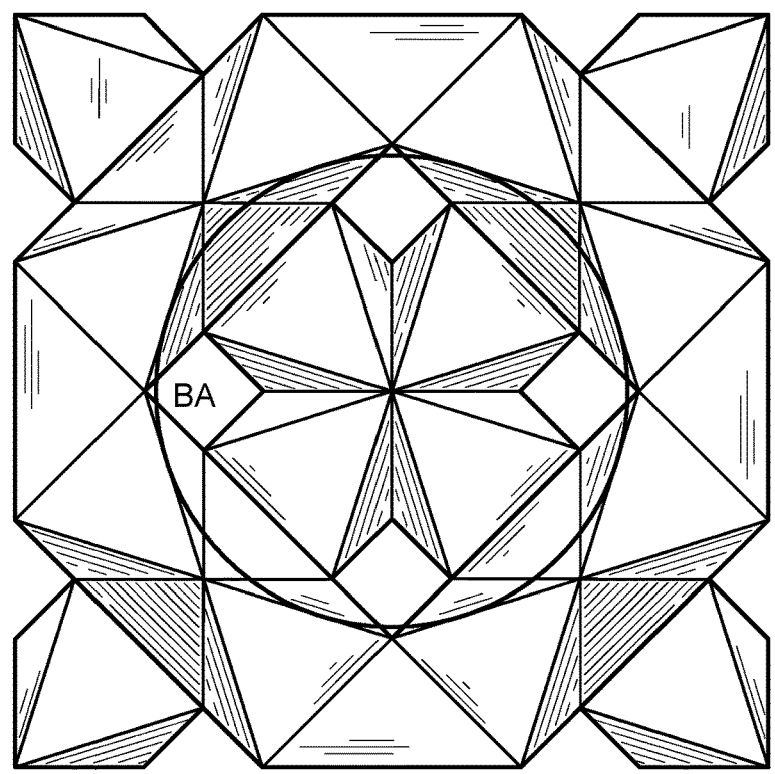
FIG. 5 is a side view of the central void of a modified rhombic dodecahedron unit cell being measured with the largest sphere method.
Figure 6:
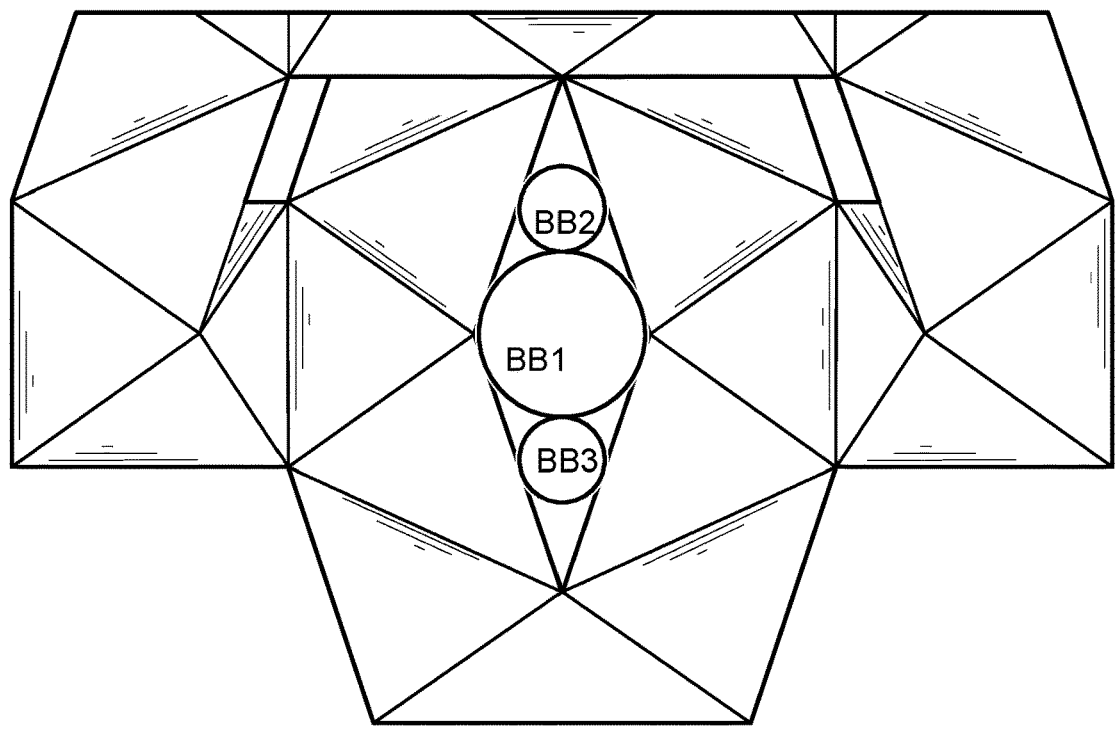
FIG. 6 is a view from a direction normal to the planar direction of an interconnection being measured with the largest sphere method.

The size of the central void and interconnections can alternatively be defined by the largest sphere method as described herein. Using the largest sphere method, the central void can be defined by the diameter of the largest sphere that can fit within the central void without intersecting the struts. FIG. 5 depicts an example of the largest sphere method being used to define the size of a central void with a sphere with a diameter of BA. FIG. 6 is a view from a direction normal to the planar direction of an interconnection being measured with the largest sphere method. The interconnections are generally rhombus shaped and their size can alternatively be defined by the size of the length and width of three circles drawn within the opening. As shown in FIG. 6, within the plane defining a side, a first circle BB1 is drawn at the center of the opening so that it is the largest diameter circle that can fit without intersecting the struts. A second circle BB2 and third circle BB3 is then drawn so that they are tangential to the first circle BB1 and the largest diameter circles that can fit without intersecting the struts. The diameter of the first circle BB1 is the width of the interconnection and the sum of the diameters of all three circles BB1, BB2 & BB3 represents the length of the interconnection. Using this method of measurement removes the acute corners of the rhombus shaped opening from the size determination. In some instances, it is beneficial to remove the acute corners of the rhombus shaped opening from the calculated size of the interconnections because of the limitations of additive manufacturing processes. For example, if an SLS machine has a resolution of 12 μm where the accuracy is within 5 μm, it is possible that the acute corner could be rounded by the SLS machine, making it unavailable for bone ingrowth. When designing lattices for manufacture on less precise additive process equipment, it can be helpful to use this measuring system to better approximate the size of the interconnections.

Using the alternative measuring method, in some examples, the width of the interconnections is approximately 600 μm and the length of the interconnections is approximately 300 μm. The use of a 600 μm length and 300 μm width provides an opening within the known pore sizes for bone growth and provides a surface area of roughly 1.8 square millimeters, allowing high strength bone growth to form. Alternative embodiments may contain interconnections with a cross sectional area of 1.0 to 15.0 times the cross-sectional area of a pore with a diameter of 300 μm. Other embodiments may contain interconnections with a cross sectional area of 1.0 to 15.0 times the cross-sectional area of a pore with a diameter of 900 μm.

The MRDD unit cell also has the advantage of providing at least two sets of substantially homogenous pore or opening sizes in a lattice structure. In some embodiments, a first set of pores have a width of about 200 μm to 900 μm and a second set of pores have a width of about 1 to 15 times the width of the first set of pores. In some embodiments, a first set of pores can be configured to promote the growth of osteoblasts and a second set of pores can be configured to promote the growth of osteons. Pores sized to promote osteoblast growth can have a width of between and including about 100 μm to 900 μm. In some embodiments, pores sized to promote osteoblast growth can have a width that exceeds 900 μm. Pores sized to promote the growth of osteons can have a width of between and including about 100 μm to 13.5 mm. In some embodiments, pores sized to promote osteon growth can have a width that exceeds 13.5 mm.

In some embodiments, it is beneficial to include a number of substantially homogenous larger pores and a number of substantially homogenous smaller pores, where the number of larger pores is selected based on a ratio relative to the number of smaller pores. For example, some embodiments have one large pore for every one to twenty five small pores in the lattice structure. Some embodiments preferably have one large pore for every eight to twelve smaller pores. In some embodiments, the number of larger and smaller pores can be selected based on a percentage of the total number of pores in a lattice structure. For example, some embodiments can include larger pores for 4% to 50% of the total number of pores and smaller pores for 50% to 96% of the total number of pores. More preferably, some embodiments can include larger pores for about 8% to 13% of the total number of pores and smaller pores for about 87% to 92% of the total number of pores. It is believed that a lattice constructed with sets of substantially homogenous pores of the disclosed two sizes provides a lattice structure that simultaneously promotes osteoblast and osteon growth.

The MRDD unit cell may also be defined by the size of the interconnections when viewed from a side, top or bottom of a unit cell. The MRDD unit cell has the same appearance when viewed from a side, top or bottom, making the measurement in a side view representative of the others. When viewed from the side, as in FIG. 4, an MRDD unit cell displays four distinct diamond shaped interconnections with substantially right angles. The area of each interconnection is smaller when viewed in the lateral direction than from a direction normal to the planar direction of each interconnection, but the area when viewed in the lateral direction can represent the area available for bone to grow in that direction. In some embodiments, it may be desirable to index the properties of the unit cell and lattice based on the area of the interconnections when viewed from the top, bottom or lateral directions.

In some embodiments of the lattice structures disclosed herein, the central void is larger than the length or width of the interconnections. Because the size of each interconnection can be substantially the same in a repeating MRDD structure, the resulting lattice can be comprised of openings of at least two discrete sizes. In some embodiments, it is preferable for the diameter of the central void to be approximately two times the length of the interconnections. In some embodiments, it is preferable for the diameter of the central void to be approximately four times the width of the interconnections.

In some embodiments, the ratio between the diameter of the central void and the length or width of the interconnections can be changed to create a structural lattice of a particular strength. In these embodiments, there is a correlation where the ratio between the central void diameter and the length or width of the interconnections increases as the strength of the structural lattice increases.

Figure 7:
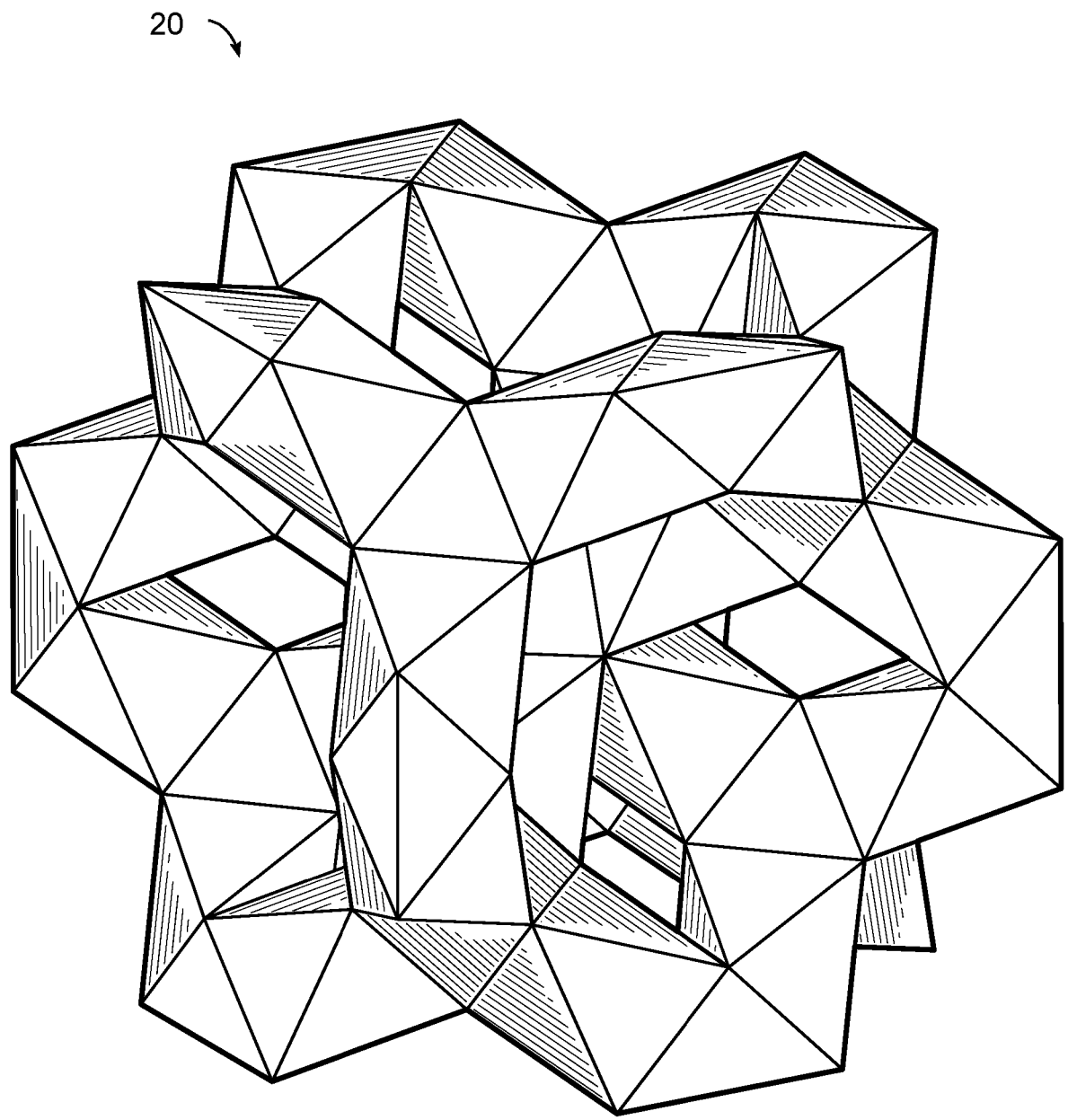
FIG. 7 is an isometric view of a single radial dodeca-rhombus unit cell.
Figure 8:
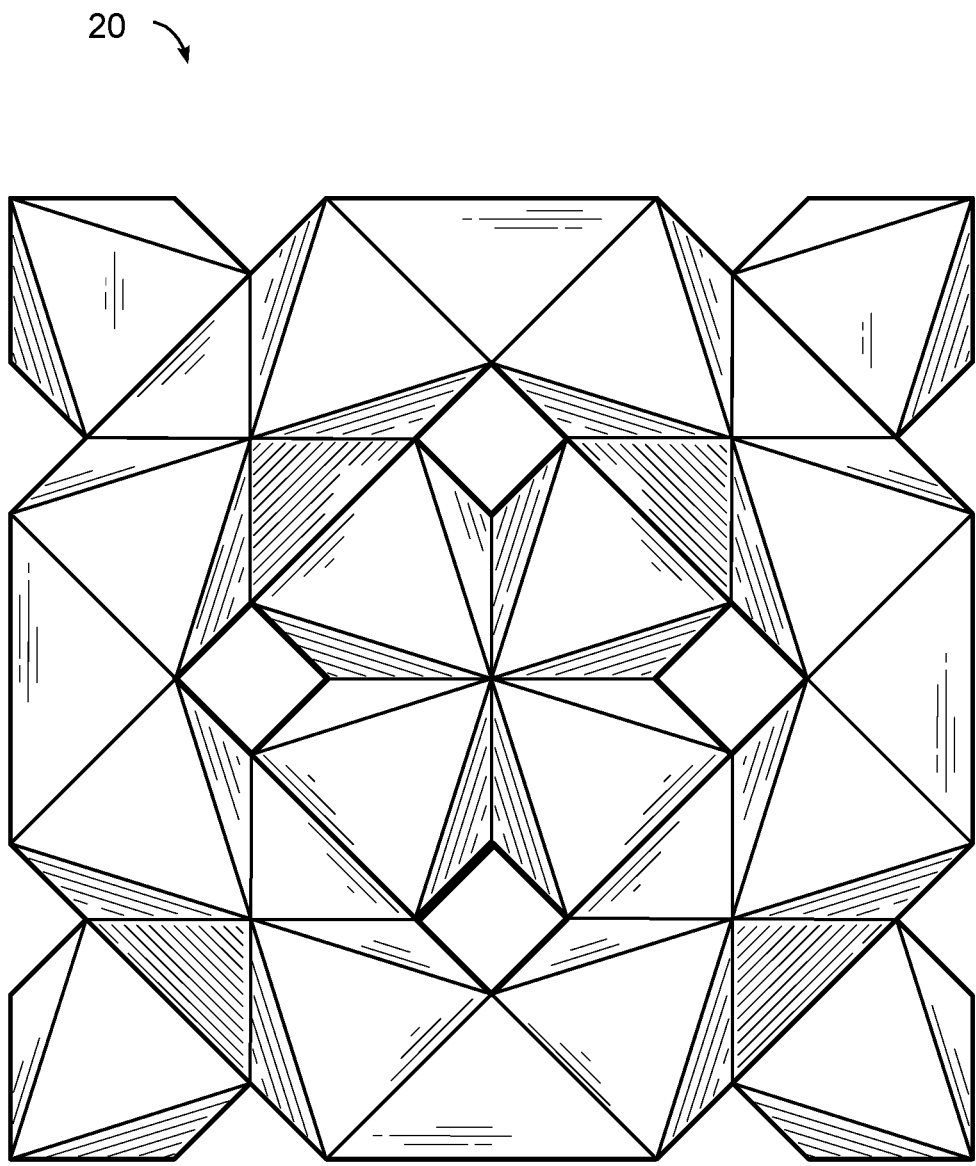
FIG. 8 is a side view of a single radial dodeca-rhombus unit cell.

It is also believed that a lattice using a repeating radial dodeca-rhombus (hereinafter "RDDR") unit cell can present a preferable combination of stiffness, strength, fatigue resistance, and conditions for bone ingrowth. In some embodiments, the repeating RDDR lattice is comprised of titanium or a titanium alloy. FIG. 7 is an isometric view of a single RDDR unit cell 20 containing a full RDDR structure. FIG. 8 is a side view of a single RDDR unit cell 20 showing the configuration of interconnections when viewed from a lateral direction. A top or bottom view of the RDDR unit cell 20 would be substantially the same as the side view depicted in FIG. 8.

As used herein, an RDDR unit cell 20 is a three-dimensional shape comprised of a central node with radial struts and mirrored struts thereof forming twelve rhombus shaped structures. The node is preferably an octahedron, more specifically a square bipyramid (i.e. a pyramid and inverted pyramid joined on a horizontal plane). Each face of the node is preferably triangular and fixed to each face is a strut comprised of six triangular facets and two end faces. The central axis of each strut can be orthogonal or non-orthogonal relative to the planar surface of each node face. The central axis may follow the centroid of the strut. The RDDR is also characterized by a central node with one strut attached to each face, resulting in a square bipyramid node with eight struts attached.

Figure 9:
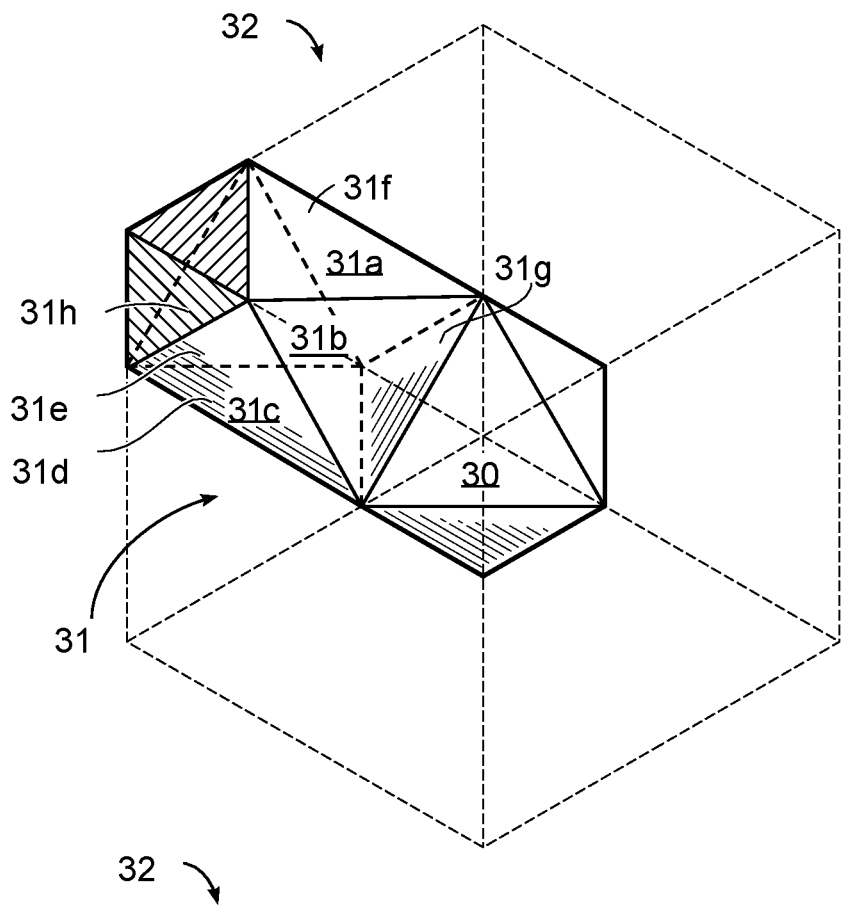
FIG. 9 is an isometric view of an example of a single node and single strut combination that could be used in a radial dodeca-rhombus unit cell.

Examples of node and strut combinations are shown in FIGS. 9-13. FIG. 9 depicts an isometric view of a single node 30 with a single strut 31 attached. The node 30 is a square bipyramid oriented so that two peaks face the top and bottom of a volume 32 defining the bounds of the node 30 and any attached strut(s) 31. The node 30 is oriented so that the horizontal corners are positioned at their closest point to the lateral sides of the volume 32. The strut 31 extends from a node 30 face to the corner of the volume 32 defining the bounds of the node and attached struts. In FIG. 9, the central axis of the strut 31 is 45 degrees above the horizontal plane where the node's planar face is 45 degrees above a horizontal plane.

FIG. 9 also details an octahedron strut 31, where dashed lines show hidden edges of the strut. The strut 31 is an octahedron with an elongate portion of six substantially similar elongate faces and two end faces. The elongate faces 31a, 31b, 31c, 31d, 31e, and 31f of the strut 31 define the outer surface of the strut's elongate and somewhat cylindrical surface. Each of the elongate faces 31a, 31b, 31c, 31d, 31e, and 31f is an isosceles triangle with a first internal angle, angle A, and a second internal angle, angle B, where angle B is greater than angle A. The strut 31 also has two end faces 31f, 31g which are isosceles triangles that are substantially similar to one another, having a first internal angle, angle C, and a second internal angle, angle D, and where angle D is greater than angle C. When comparing the internal angles of the elongate faces 31a, 31b, 31c, 31d, 31e, and 31f to the end faces 31f and 31g, angle C is greater than angle A.

Figure 10:
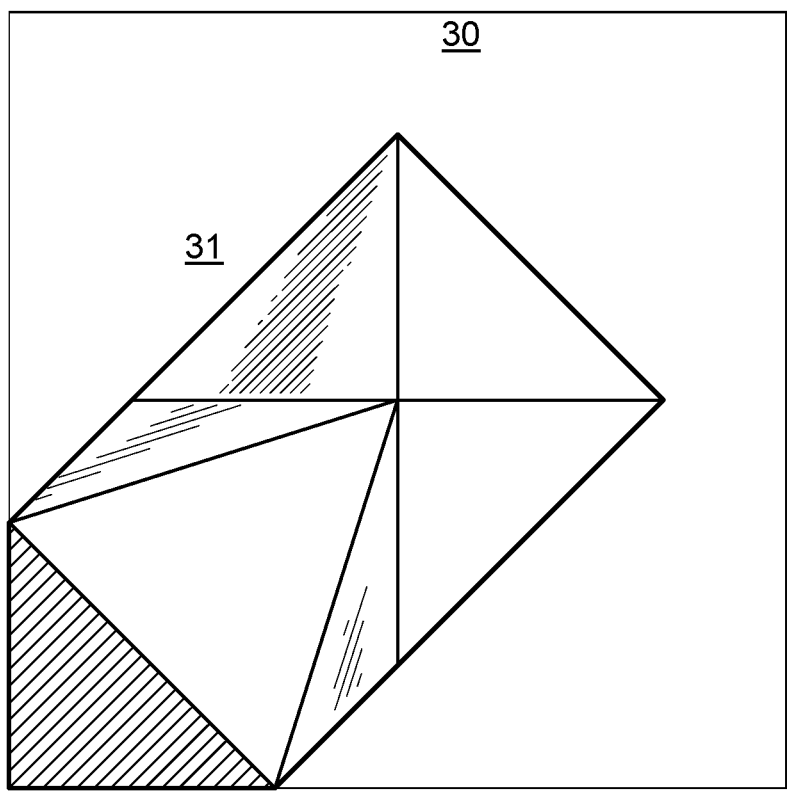
FIG. 10 is a side view of an example of a single node and single strut combination that could be used in a radial dodeca-rhombus unit cell.
Figure 11:
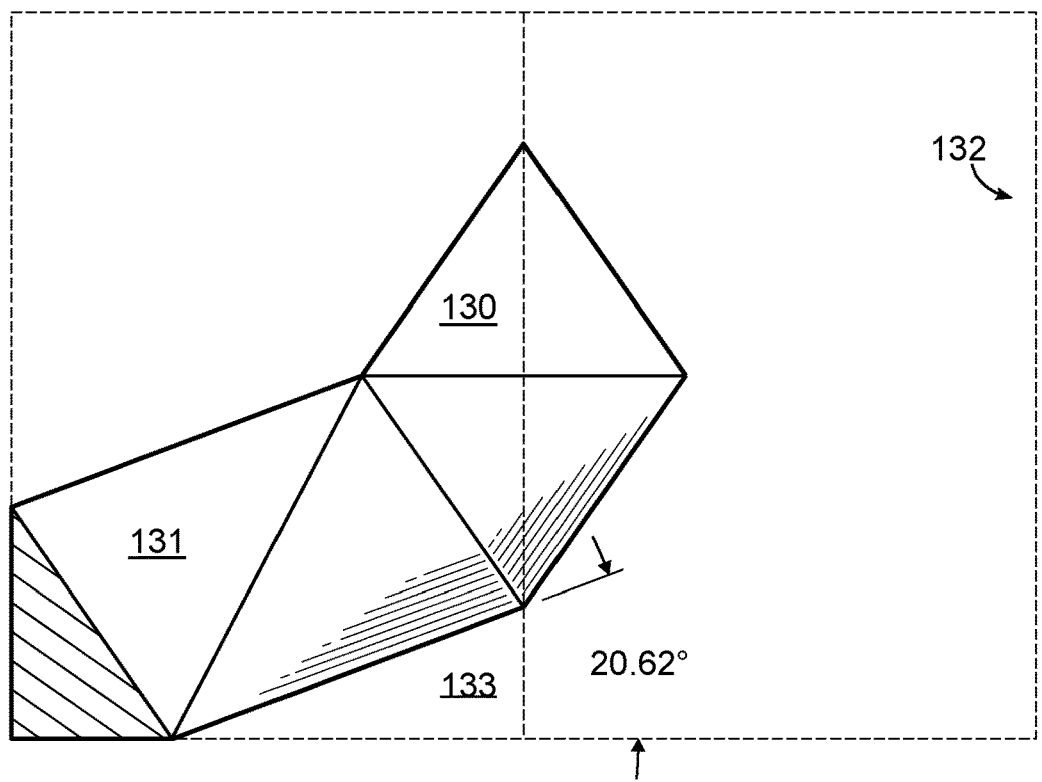
FIG. 11 is a side view of a single node and single strut combination configured for use in a lattice with an elastic modulus of approximately 3 GPa, viewed from the corner of the volume defining the bounds of the combination.
Figure 12:
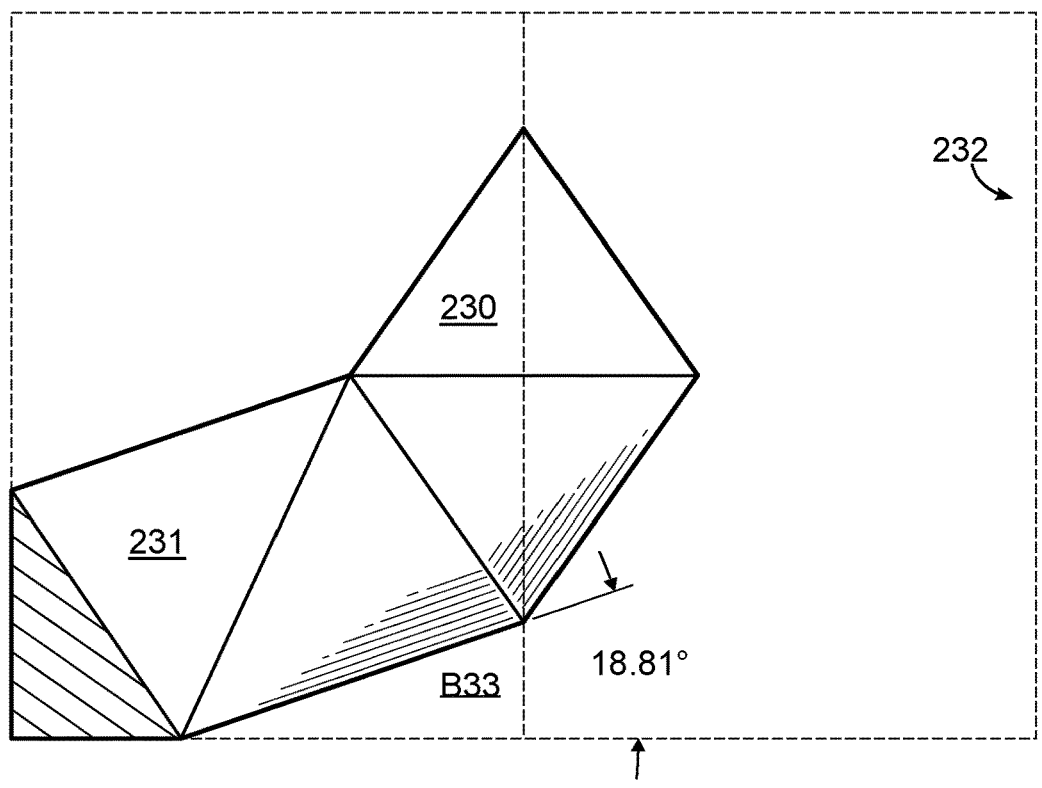
FIG. 12 is a side view of a single node and single strut combination configured for use in a lattice with an elastic modulus of approximately 4 GPa, viewed from the corner of the volume defining the bounds of the combination.
Figure 13:
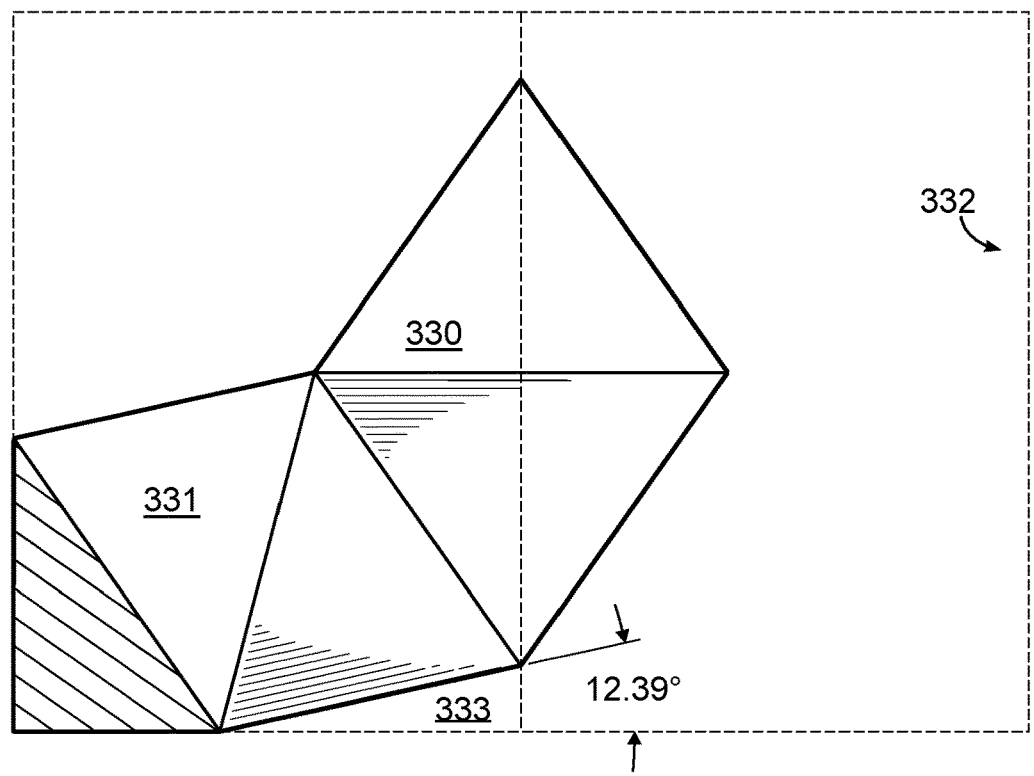
FIG. 13 is a side view of a single node and single strut combination configured for use in a lattice with an elastic modulus of approximately 10 GPa, viewed from the corner of the volume defining the bounds of the combination.

In FIG. 10 is a side view of the node 30 and strut 31 combination bounded by volume 32. In the side view, the height of the node 30 compared to the height of the cube 32 can be compared easily. FIGS. 11-13 depict side views of node and strut combinations viewed from a corner of the volume rather than a wall or face, and where the combinations have been modified from FIGS. 9-10 to change the volumetric density of the resulting unit cell. FIG. 11, the height of the node 130 has increased relative to the height of the volume 132. Since the distal end of the strut 131 is fixed by the location of a corner of the volume 132, the strut 131 must change its angle relative to its attached node face so that it becomes non-orthogonal. The node 130 and strut 131 combination, where the angle of the strut 131 from a horizontal plane is about 20.6 degrees, would be appropriate for a lattice structure with an elastic modulus of approximately 3 GPa.

In FIG. 12, the height of the node 230 relative to the height of the cube 232 has been increased over the ratio of FIG. 11 to create a node 230 and strut 231 combination that would be appropriate for a lattice structure with an elastic modulus of approximately 4 GPa. As the height of the node 230 increases, the angle between the strut 231 and a horizontal plane decreases to about 18.8 degrees. As the height of the node 230 increases, the size of the node faces also increase so that the size of the strut 231 increases. While the distal end of the strut 231 is fixed to the corner of the volume 232, the size of the distal end increases to match the increased size of the node face to maintain a substantially even strut diameter along its length. As the node and strut increase in size, the volumetric density increases, as does the elastic modulus. In FIG. 13, the height of the node 330 relative to the height of the volume 332 has been increased over the ratio of FIG. 13 to create a node 330 and strut 331 combination that would be appropriate for a lattice structure with an elastic modulus of approximately 10 GPa. In this configuration, the angle 333 between the strut 331 and a horizontal plane decreases to about 12.4 degrees and the volumetric density increases over the previous examples. The single node and strut examples can be copied and/or mirrored to create unit cells of appropriate sizes and characteristics. For instance, the angle between the strut and a horizontal plane could be increased to 25.8 degrees to render a lattice with a 12.3% volumetric density and an elastic modulus of about 300 MPa. While a single node and single strut were shown in the examples for clarity, multiple struts may be attached to each node to create an appropriate unit cell.

Adjacent struts extending from adjacent node faces on either the upper half or lower half of the node have an angle from the horizontal plane and a lateral separation angle defined by an angle between the strut directions of adjacent struts. In the MRDD and RDDR structures, adjacent struts have an external edge or face of the elongate portion extending closest to the relevant adjacent strut. The lateral separation angle, as used herein, generally refers to the angle between an external edge or face of the elongate portion of a strut extending closest to the relevant adjacent strut. In some embodiments, a lateral separation angle defined by a line extending between the center of the strut end faces or a line defined by the center of mass of the struts can be used in reference to a similar calculation for an adjacent strut.

Figure 14:
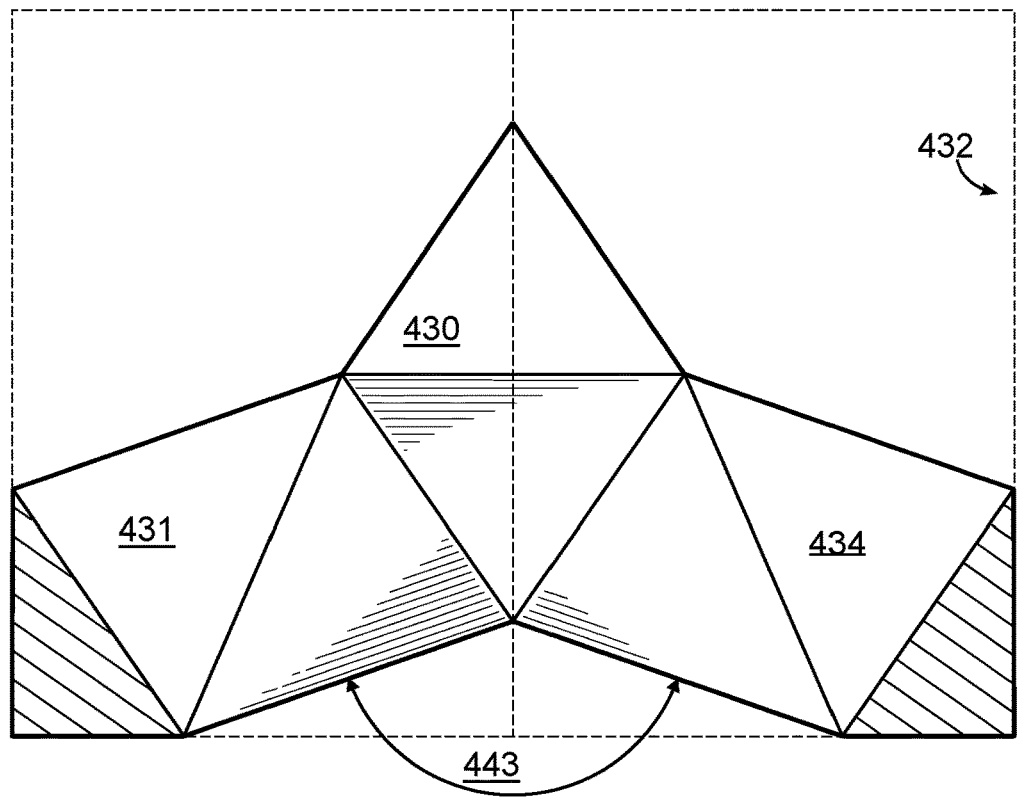
FIG. 14 is a side view of a single node and two adjacent struts viewed from the corner of the volume defining the bounds of the combination and the lateral separation angle.

The lateral separation angle is the angle between the nearest face or edge of a strut to an adjacent strut. The lateral separation angle can be measured as the smallest angle between the nearest edge of a strut to the nearest edge of an adjacent strut, in a plane containing both strut edges. The lateral separation angle can also be measured as the angle between the nearest face of a strut to the nearest face of an adjacent strut in a plane normal to the two strut faces. In embodiments without defined strut edges or strut faces, the lateral separation angle can be measured as an angle between the nearest portion of one strut to the nearest portion of an adjacent strut. For a unit cell in a cubic volume, as the strut angle from the horizontal plane decreases, the lateral separation angle approaches 90 degrees. For a unit cell in a cubic volume, as the strut angle from the horizontal plane increases, the lateral separation angle approaches 180 degrees. In some embodiments, it is preferable to have a lateral separation angle greater than 109.5 degrees. In some embodiments, it is preferable to have a lateral separation angle of less than 109.5 degrees. In some embodiments, it is preferable to have a lateral separation angle of between and including about 108 degrees to about 156 degrees. In some embodiments, it is more preferable to have a lateral separation angle of between and including 111 degrees to 156 degrees. In some embodiments, it is more preferable to have a lateral separation angle of between and including 108 degrees to 120 degrees. In some embodiments, it is most preferable to have a lateral separation angle of between and including about 111 degrees to 120 degrees. In some embodiments, it is more preferable to have a lateral separation angle of between and including 128 degrees to 156 degrees. FIG. 14 depicts a side view, viewed from a corner of the cube 432, of a single node 430 with two adjacent struts 431, 434 attached, and where the lateral separation angle 443 is identified. When measured from the nearest edge of a strut to the nearest edge of an adjacent strut, the lateral separation angle 443 is about 116 degrees.

Figure 16:
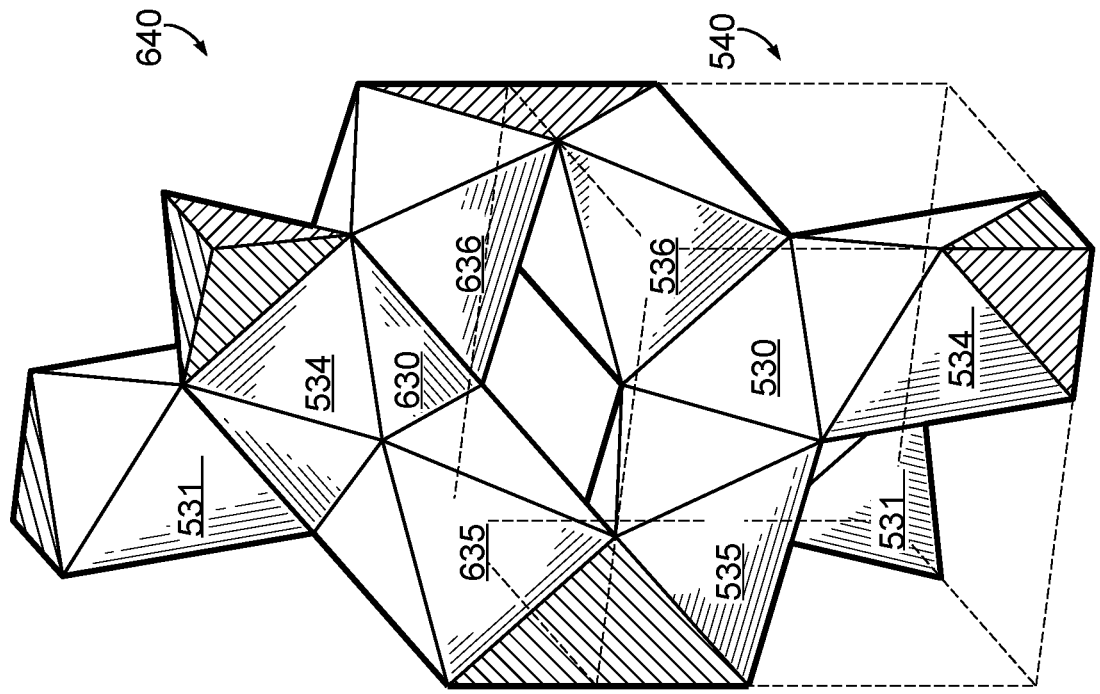
FIG. 16 is an isometric view of two sub-unit cells in a stacked formation where the upper sub-unit cell is inverted and fixed to the top of the lower sub-unit cell.
Figure 15:
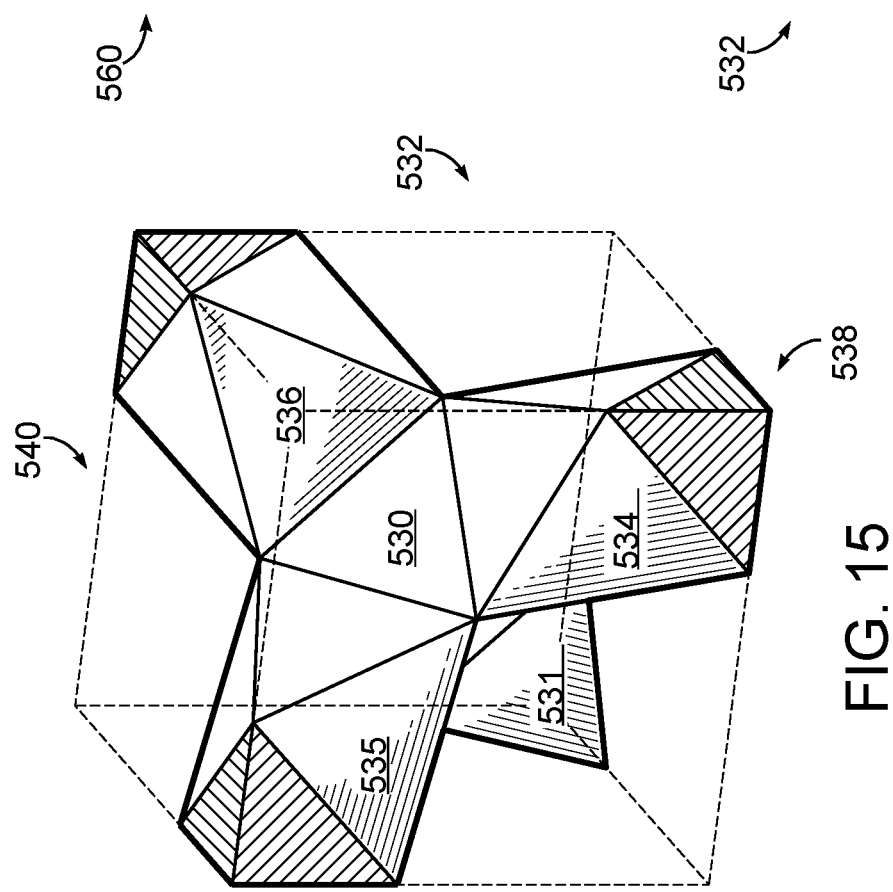
FIG. 15 is an isometric view of a sub-unit cell comprised of a single node and four struts.
Figure 17:
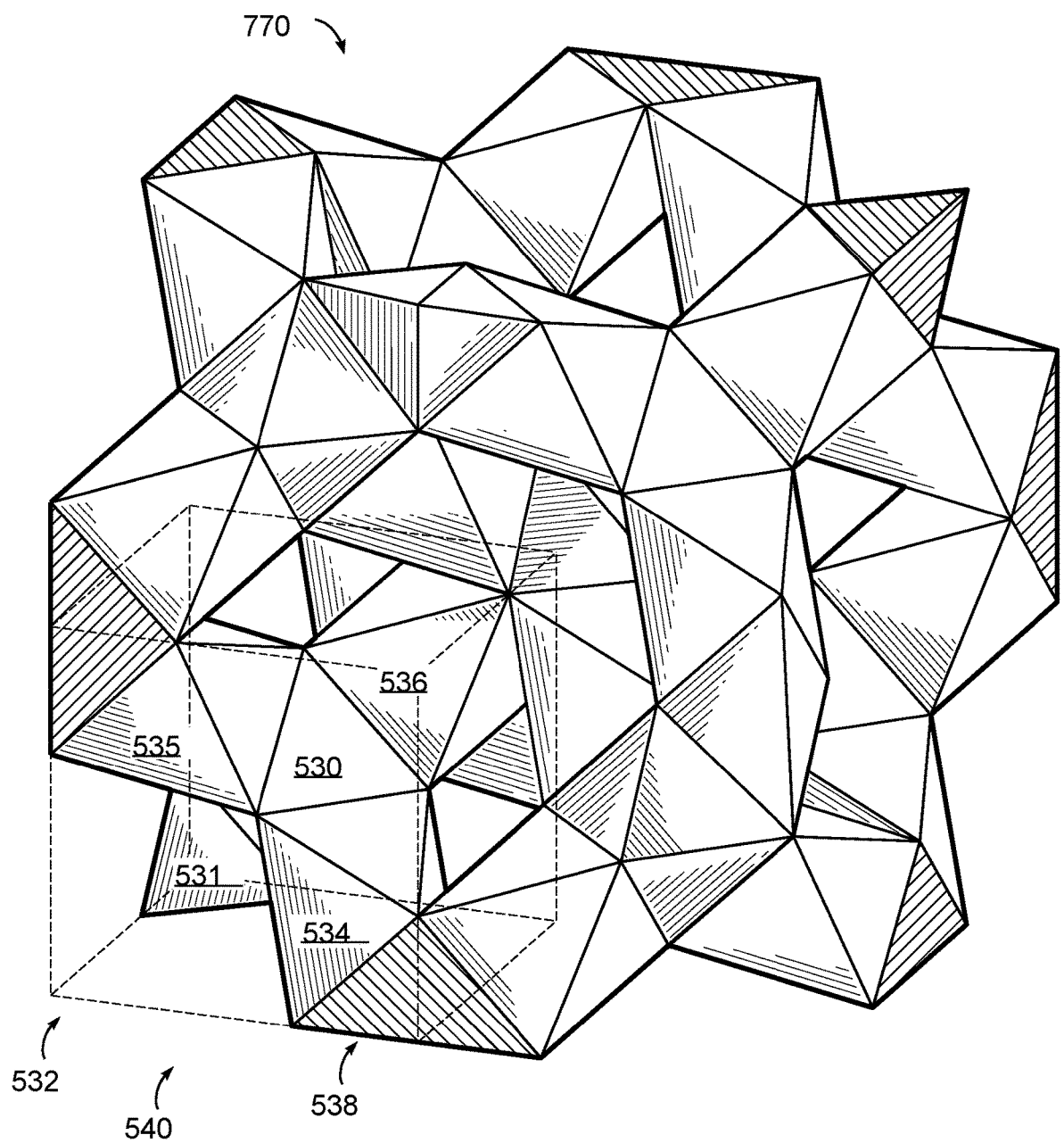
FIG. 17 is an isometric view of eight sub-unit cells stacked together to form a single unit cell.

In some embodiments, a unit cell is built up from multiple sub-unit cells fixed together. FIG. 15 depicts an isometric view of an exemplary sub-unit cell comprising a single node and four struts. FIG. 16 depicts an isometric view of two sub-unit cells in a stacked formation where the upper sub-unit cell is inverted and fixed to the top of the lower sub-unit cell. FIG. 17 depicts an isometric view of eight sub-unit cells stacked together to form a single RDDR unit cell.

In FIG. 15, the node 530 is a square bipyramid, oriented so that the two peaks face the top and bottom of a cubic volume 532. In some embodiments, the volume 532 can be a cuboid volume, a hexahedron volume, an amorphous volume or of a volume with one or more non-orthogonal sides. The peaks refer to the point where four upper faces meet and the point where four lower faces meet. The node 530 is oriented so that the horizontal vertices face the lateral sides of the cubic volume 532. The strut 531 is fixed to a lower face of the node 530 face on its proximate end and extends to the nearest corner of the cubic volume 532 at its distal end. The distal end of the strut 531 can remain fixed to the cubic volume 532 even if the node 530 changes in size to adjust the sub-unit cell properties.

On the lower face of the node 530 opposite the face which strut 531 is fixed, the proximate end of strut 534 is fixed to the node 530. The strut 534 extends to the nearest corner of cubic volume 532 at its distal end. The strut 535 is fixed on its proximate end to an upper node 530 face directed about 90 degrees laterally from the node B530 face fixed to strut 531. The strut 535 extends to the nearest corner of the cubic volume 532 at its distal end. On the upper face of the node 530 opposite the face which strut 535 is fixed, the proximate end of strut B536 is fixed to the node 530. The strut 536 extends to the nearest corner of the cubic volume 532 at its distal end.

In some embodiments, the struts 531, 534-536 are octahedrons with triangular faces. The strut face fixed to a node 530 face can be substantially the same size and orientation of the node 530 face. The strut face fixed to the nearest corner of the cube 532 can be substantially the same size as the strut face fixed to the node 530 and oriented on a substantially parallel plane. The remaining six faces can be six substantially similar isosceles triangles with a first internal angle and a second internal angle larger than said first internal angle. The six substantially similar isosceles triangles can be fixed along their long edges to an adjacent and inverted substantially similar isosceles triangle to form a generally cylindrical shape with triangular ends.

When forming a sub-unit cell 540, it can be beneficial to add an eighth node 538 to each corner of the cube 532 fixed to a strut 531, 534-536. When replicating the sub-unit cell 540, the eighth node 538 attached to each strut end is combined with eighth nodes from adjacent sub-unit cells to form nodes located between the struts of adjacent sub-unit cells.

FIG. 16 is a first sub-unit cell 540 fixed to a second sub-unit cell 640 to form a quarter unit cell 560 used in some embodiments. The second sub-unit cell 640 comprises a square bipyramid node 630 is a square bipyramid, oriented so that the two peaks face the top and bottom of a cubic volume. The node 630 is oriented so that the horizontal vertices face the lateral sides of the cubic volume. The strut 635 is fixed to a lower face of the node 630 face on its proximate end and extends to the nearest corner of the cubic volume at its distal end. On the lower face of the node 630 opposite the face which strut 635 is fixed, the proximate end of strut 636 is fixed to the node 630. The strut 636 extends to the nearest corner of cubic volume at its distal end. The strut 634 is fixed on its proximate end to an upper node 630 face directed about 90 degrees laterally from the node 630 face fixed to strut 635. The strut 634 extends to the nearest corner of the cubic volume at its distal end. On the upper face of the node 630 opposite the face which strut 634 is fixed, the proximate end of strut 631 is fixed to the node 630. The strut 631 extends to the nearest corner of the cubic volume at its distal end.

The first sub-unit 540 is used as the datum point in the embodiment of FIG. 16, however, it is appreciated that the second sub-unit cell 640 or another point could also be used as the datum point. Once the first sub-unit cell 540 is fixed in position, it is replicated so that the second sub-unit cell 640 is substantially similar to the first. The second sub-unit cell 640 is rotated about its central axis prior to being fixed on the top of the first unit-cell 540. In FIG. 16, the second sub-unit cell 640 is inverted to achieve the proper rotation, however, other rotations about the central axis can achieve the same result. The first sub-unit cell 540 fixed to the second sub-unit cell 640 forms a quarter unit cell 560 that can be replicated and attached laterally to other quarter unit cells to form a full unit cell.

Alternatively, a full unit cell can be built up by fixing a first group of four substantially similar sub-unit cells together laterally to form a square, rectangle or quadrilateral when viewed from above. A second group of four substantially similar sub-unit cells rotated about their central axis can be fixed together laterally to also form a square, rectangle or quadrilateral when viewed from above. The second group of sub-unit cells can be rotated about their central axis prior to being fixed together laterally or inverted after being fixed together to achieve the same result. The second group is then fixed to the top of the first group to form a full unit cell.

FIG. 17 is an example of a full unit cell 770 formed by replicating the sub-unit cell 540 of FIG. 15. The cube 532 defining the bounds of the sub-unit cell 540 is identified as well as the node 530 and struts 531, 534-536 for clarity. The full unit cell 770 of FIG. 17 can be formed using the methods described above or using variations within the inventive concept.

Each strut extending from the node, for a given unit cell, can be substantially the same length and angle from the horizontal plane, extending radially from the node. At the end of each strut, the strut is mirrored so that struts extending from adjacent node faces form a rhombus shaped opening. Because the struts can be non-orthogonal to the node faces, rhombuses of two shapes emerge. In this configuration, a first group of four rhombuses extend radially from the node oriented in vertical planes. The acute angles of the first group of rhombuses equal twice the strut angle from the horizontal plane and the obtuse angles equal 180 less the acute angles. Also in this configuration is a second group of eight rhombuses extending radially so that a portion of the second group of eight rhombuses fall within the lateral separation angle between adjacent struts defining the first group of four rhombuses. The acute angles of the second group of rhombuses can be about the same as the lateral separation angle between adjacent struts that define the first group of four rhombuses and the obtuse angles equal 180 less the acute angles. The characteristics of a scaffold may also be described by its surface area per volume. For a 1.0 mm×1.0 mm×1.0 mm solid cube, its surface area is 6.0 square mm. When a 1.0 cubic mm structure is comprised of a lattice structure rather than a 100% volumetric density material, the surface area per volume can increase significantly. In low volumetric density scaffolds, the surface area per volume increases as the volumetric density increases. In some embodiments, a scaffold with a volumetric density of 30.1% would have a surface area of 27.4 square mm per cubic mm. In some embodiments, if the volumetric density was decreased to 27.0%, the lattice would have a surface area of 26.0 square mm per cubic mm and if the volumetric density were decreased to 24.0%, the lattice would have a surface area of 24.6 square mm per cubic mm.

The MRDD and RDDR structures disclosed herein also have the advantage of an especially high modulus of elasticity for a given volumetric density. When used as a lattice or scaffold, an implant with an adequate modulus of elasticity and a low volumetric density can be achieved. A low volumetric density increases the volume of the implant available for bone ingrowth.

In Table 1, below, are a number of example lattice configurations of various lattice design elastic moduli. An approximate actual elastic modulus was given for each example, representing a calculated elastic modulus for that lattice after going through the manufacturing process. The lattice structures and implants disclosed herein can be designed to a design elastic modulus in some embodiments and to an approximate actual elastic modulus in other embodiments. One advantage of the presently disclosed lattice structures is that the approximate actual elastic modulus is much closer to the design elastic modulus than has been previously achieved. During testing, one embodiment of a lattice was designed for a 4.0 GPa design elastic modulus. Under testing, the lattice had an actual elastic modulus of 3.1 GPa, achieving an actual elastic modulus within 77% of the design elastic modulus.

For each lattice design elastic modulus, a volumetric density, ratio of design elastic modulus to volumetric density, surface area in mm$^2$, ratio of surface area to volumetric density and ratio of surface area to lattice design elastic modulus is given.

TABLE 1

Table of example lattice structures based on lattice design elastic modulus in GPa

| Lattice Design Elastic Modulus (GPa) | Approx. Actual Elastic Modulus (GPa) | Volumetric Density (percent) | Ratio of Design Elastic Modulus to Volumetric Density | Surface Area (mm$^2$) | Ratio of Surface Area to Volumetric Density | Ratio of Surface Area to Lattice Design Elastic Modulus |
|---|---|---|---|---|---|---|
| 0.3 | 0.233 | 18.5 | 1.6 | 22.5 | 121.5 | 74.9 |
| 3 | 2.33 | 29.9 | 10.0 | 27.5 | 92.2 | 9.2 |
| 4 | 3.10 | 33.4 | 12.0 | 28.8 | 86.4 | 7.2 |
| 5 | 3.88 | 36.4 | 13.8 | 29.9 | 82.2 | 6.0 |
| 6 | 4.65 | 38.8 | 15.5 | 30.7 | 79.1 | 5.1 |
| 7 | 5.43 | 40.8 | 17.2 | 31.3 | 76.9 | 4.5 |
| 8 | 6.20 | 42.1 | 19.0 | 31.8 | 75.4 | 4.0 |
| 9 | 6.98 | 43.2 | 20.8 | 32.1 | 74.3 | 4.0 |

In some of the embodiments disclosed herein, the required strut thickness can be calculated from the desired modulus of elasticity. Using the following equation, the strut thickness required to achieve a particular elastic modulus can be calculated for some MRDD and RDDR structures:

$$\text{Strut Thickness} = (-0.0035 \ast (E^2)) + (0.0696 \ast E) + 0.4603$$

In the above equation, "E" is the modulus of elasticity. The modulus of elasticity can be selected to determine the required strut thickness required to achieve that value or it can be calculated using a preselected strut thickness. The strut thickness is expressed in mm and represents the diameter of the strut. The strut thickness may be calculated using a preselected modulus of elasticity or selected to determine the modulus of elasticity for a preselected strut thickness.

In some embodiments, the unit cell can be elongated in one or more directions to provide a lattice with anisotropic properties. When a unit cell is elongated, it generally reduces the elastic modulus in a direction normal to the direction of the elongation. The elastic modulus in the direction of the elongation is increased. It is desirable to elongate cells in the direction normal to the direction of new bone growth contained within the interconnections, openings and central voids (if any). By elongating the cells in a direction normal to the desired direction of reduced elastic modulus, the shear strength in the direction of the elongation may be increased, providing a desirable set of qualities when designing a structural scaffold. Covarying the overall stiffness of the scaffold may augment or diminish this effect, allowing variation in one or more directions.

In some embodiments, the sub-unit cells may be designing by controlling the height of the node relative to the height of the volume that defines the sub-unit cell. Controlling the height of the node can impact the final characteristics and appearance of the lattice structure. In general, increasing the height of the node increases the strut thickness, increases the volumetric density, increases the strength and increases the elastic modulus of the resulting lattice. When increasing the height of the node, the width of the node can be held constant in some embodiments or varied in other embodiments.

In some embodiments, the sub-unit cells may be designing by controlling the volume of the node relative to the volume that defines the sub-unit cell. Controlling the volume of the node can impact the final characteristics and appearance of the lattice structure. In general, increasing the volume of the node increases the strut thickness, increases the volumetric density, increases the strength and increases the elastic modulus of the resulting lattice. When increasing the volume of the node, the width or height of the node could be held constant in some embodiments.

In Table 2, below, are a number of example lattice configurations of various lattice design elastic moduli. An approximate actual elastic modulus was given for each example, representing a calculated elastic modulus for that lattice after going through the manufacturing process. The lattice structures and implants disclosed herein can be designed to a design elastic modulus in some embodiments and to an approximate actual elastic modulus in some embodiments. For each lattice design elastic modulus, a lattice approximate elastic modulus, a node height, a volumetric density, a node volume, a ratio of node height to volumetric density, a ratio of node height to lattice design elastic modulus and a ratio of volumetric density to node volume is given.

TABLE 2

Table of example lattice structures based on lattice design elastic modulus in GPa

| Lattice Design Elastic Modulus (GPa) | Lattice Approx. Actual Elastic Modulus (GPa) | Node Height (mm) | Volumetric Density (percent) | Node Volume (mm3) | Ratio of Node Height to Vol. Density | Ratio of Node Height to Lattice Design Elastic Modulus | Ratio of Vol. Density to Node Volume |
|---|---|---|---|---|---|---|---|
| 0.30 | 0.23 | 0.481 | 18.5 | 0.0185 | 2.60 | 1.60 | 9.98 |
| 3.00 | 2.33 | 0.638 | 29.9 | 0.0432 | 2.14 | 0.21 | 6.91 |
| 4.00 | 3.10 | 0.683 | 33.4 | 0.0530 | 2.05 | 0.17 | 6.29 |
| 5.00 | 3.88 | 0.721 | 36.4 | 0.0624 | 1.98 | 0.14 | 5.82 |
| 6.00 | 4.65 | 0.752 | 38.8 | 0.0709 | 1.94 | 0.13 | 5.48 |
| 7.00 | 5.43 | 0.776 | 40.8 | 0.0779 | 1.90 | 0.11 | 5.23 |
| 8.00 | 6.20 | 0.793 | 42.1 | 0.0831 | 1.88 | 0.10 | 5.07 |
| 9.00 | 6.98 | 0.807 | 43.2 | 0.0877 | 1.87 | 0.09 | 4.93 |

Some embodiments of the disclosed lattice structures are particularly useful when provided within an elastic modulus range between an including 0.375 GPa to 4 GPa. Some embodiments, more preferably, include a lattice structure with an elastic modulus between and including 2.5 GPa to 4 GPa. Some embodiments include a lattice structure with a volumetric density between and including 5% to 40%. Some embodiments, more preferably, include a lattice structure with a volumetric density between and including 30% to 38%.

The lattice structures disclosed herein have particularly robust loading and fatigue characteristics for low volumetric density ranges and low elastic moduli ranges. Some embodiments of the lattice structures have a shear yield load and a compressive yield load between and including 300 to 15000N in static and dynamic loading up to 5,000,000 cycles at 5 Hz. Some embodiments have a compressive shear strength and an axial load between and including 300 to 15000N in static and dynamic loading up to 5,000,000 cycles at 5 Hz. Some embodiments have a shear strength and an axial load between and including 300 to 15000N in static and dynamic loading up to 5,000,000 cycles at 5 Hz. Some embodiments have a torsional yield load up to 15 Nm.

In one example, the inventive lattice structure has a volumetric density of between and including 32% to 38%, an elastic modulus between and including 2.5 GPa to 4 GPa and a shear strength and an axial load between and including 300 to 15000N in static and dynamic loading up to 5,000,000 cycles at 5 Hz. Some examples include a first set of substantially homogeneous openings with a width of about 200 μm to 900 μm and a second set of substantially homogenous openings with a width of about 1 to 15 times the width of the first set of openings, where the number of openings in the second set are provided at a ratio of about 1:8 to 1:12 relative to the number of openings in the first set.

The disclosed structures can also have benefits when used in applications where osteointegration is not sought or undesirable. By including a growth inhibiting coating or skin on a structure, the lattice disclosed herein can be used to provide structural support without providing a scaffold for bone growth. This may be desirable when used in temporary implants or medical devices that are intended to be removed after a period of time.

In some embodiments presented herein relate to a biocompatible lattice with increased lucency, a method of designing a lattice with increased lucency, variable markers for use in medical implants with at least a degree of radiolucency, a method of designing variable markers for use in medical implants with at least a degree of radiolucency and a method of using variable markers in medical implants with a degree of radiolucency. Variable markers, as used herein, refers to any area of an implant that has a different lucency, radiolucency, radiopacity or radiodensity in at least two different viewing directions. Variable markers can have one or more aligned directions, meaning a direction where the variable markers are designed to produce a specific lucency, radiolucency, radiopacity or radiodensity. Variable markers can have one or more misaligned directions, meaning directions where the variable markers are designed to produce a different lucency, radiolucency, radiopacity or radiodensity in comparison to an aligned direction. The variable markers can be configured to provide either increased lucency or decreased lucency when viewed in an aligned direction in comparison to when viewed in a misaligned direction. In some embodiments, the lattice structures with increased lucency include variable markers. Only exemplary embodiments are shown herein and it is understood that the use of other unit cell structures, other lattice structures and other porous structures would be within the inventive concept expressed herein. The directions described herein are in relation to the three-dimensional Cartesian Coordinate System where the x axis and y axes are horizontal and the z axis is vertical (also described herein as the x, y and z "direction"). These specific directional references are exemplary and used to the example orientations described herein.

Biocompatible lattices can be comprised of a material that has radiopaque properties when a certain bulk thickness is reached. In this case, bulk thickness means the actual thickness of the primary material in a lattice in a certain direction when the voids are removed. For instance, a lattice with a 50% volumetric density and a thickness of two inches would have a bulk thickness of one inch in that direction and a lattice with a 25% volumetric density and a thickness of two inches would have a bulk thickness of a half inch in that direction.

As used herein, radiodensity refers to the opacity or lucency of a material when viewed in in an x-ray or similar process. The radiodensity of a material may range from radiopaque to radiolucent. Radiopaque means that the material completely blocks the transmission of x-rays. A radiopaque material would show up as white in most x-rays. Radiolucent means that the material does not block the transmission of x-rays or blocks less than all of the x-rays. A fully radiolucent material would show up as black on most x-rays. A partially radiolucent material would show up as gray in most x-rays. As a material becomes more radiolucent, it shows up progressively darker in an x-ray.

Figure 18:
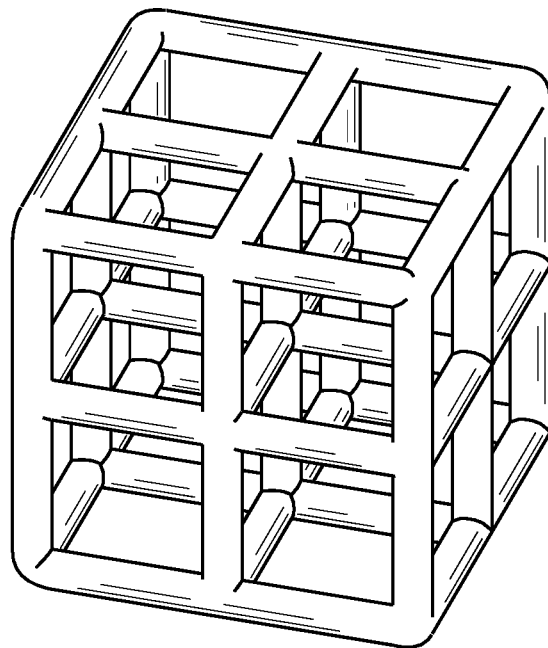
FIG. 18 is a perspective view of an example of the invention using a cubic unit cell and rotated 23 degrees about the z axis and 33.67 degrees about the x axis from a normal face.

FIG. 18 depicts an exemplary embodiment of the inventive lattice that uses a repeating cubic unit cell structure. The example in FIG. 18 has been rotated 23 degrees about the z axis and 33.67 degrees about the x axis from a normal face to provide increased dispersion. The angles of rotation about the x, y and z axes are relative to an origin orientation for a single unit cell or a structure comprised of a plurality of unit cells. In the cubic cell example, the origin orientation is where one cell face is within the plane defined by the x and z axes, another cell face is within the plane defined by the y and z axes and another cell face is within the plane defined by the x and y axes. When a cubic cell is positioned in this particular origin orientation, the rotation of the cubic cell may also be described as an angle of rotation from a normal face. Because the origin orientation is used as a reference point for the rotations taught herein, the exemplary rotations disclosed would change accordingly if a different origin orientation were used as a reference.

When using a repeating geometric unit cell in a lattice, depending on the orientation of the unit cells, the degree of lucency and the type of lucency (e.g. dispersion or disparity) through the material can be modified. While many types of lucency may be targeted using the methods described herein, only the maximum relative disparity and maximum relative dispersion angles will be discussed in detail. The maximum relative disparity angles are the rotations in degrees about the x, y and z axes for a certain repeating geometric unit cell that provides the maximum difference in lucency across the bulk volume. The maximum disparity angles result in an open cell structure with the highest possible difference between the maximum bulk thickness and minimum bulk thickness in the desired direction, in other words, a minimum uniformity of bulk thickness. The maximum relative dispersion angles are the rotations in degrees about the x, y and z axes for a certain repeating geometric unit cell that provides the minimum difference in lucency across the bulk volume. The maximum dispersion angles result in an open cell structure with the lowest possible difference between the maximum bulk thickness and minimum bulk thickness in the desired direction, in other words, a maximum uniformity of bulk thickness.

The average bulk thickness is an average taken of the bulk thickness across the bulk volume in the desired direction. For increased lucency, it is desirable to have a lower average bulk thickness in the desired direction. When orienting a structure for the maximum dispersion angle, it can be beneficial to optimize the rotation angles to create a structure with a minimum average bulk thickness and maximum uniformity of the bulk thickness in the desired direction. While a minimum average bulk thickness is desirable for lucency, the average bulk thickness in a desired direction is largely a function of the strut and unit cell characteristics. However, there can be a measurable reduction in average bulk thickness when certain types of unit cell structures with struts of certain dimensions are rotated. The reduction in average bulk thickness resulting from a rotation is more pronounced in simpler unit cell structures, such as a triangular unit cell.

The desired direction, when used to describe the embodiments, is the direction from which a lucency property is desired. Most of the time, the desired direction for a lucency property will be the direction from which an x-ray image will be taken. For example, in a spinal interbody implant, x-ray imaging is usually taken from the lateral or anterior-posterior directions. In this case, the desired direction would be from the lateral or anterior-posterior direction as the implant sits in vivo. In the drawings disclosed herein, the desired direction can be a direction normal to the sheet or screen upon which the drawings are depicted.

The repeating geometric pattern in FIG. 18 has been rotated to increase dispersion in the desired direction. For a repeating cubic unit cell, maximum relative dispersion is best achieved through the use of at least two rotations, in this case about the z and x axes. When oriented in accordance with FIG. 18, there is a minimal amount of overlap between the struts and the nodes in the sample do not overlap at all. This is an example of the maximization of uniformity of bulk thickness achievable in dispersion. Partial dispersion can be achieved with either rotation individually, but would result in either horizontal or vertical lines of disparity.

As the overall thickness of the open cell scaffold increases, more cells may be added and nodes and struts will begin to overlap, increasing the bulk thickness of the structure. The optimal angles for maximum dispersion and minimal bulk thickness will vary with the overall number of cells in the structure.

Additionally, the actual maximum dispersion depends on the ratio between the diameter of the struts compared to the size of the unit cell. As strut diameter approaches the overall size of the unit cell, effectively closing off the cells, there is no rotation that would substantially minimize bulk thickness. However, as the aspect ratio decreases, a rotation can again achieve the offsetting of struts to minimize bulk thickness. The aspect ratio is the ratio between the strut thickness and strut length. The aspect ratio can be decreased by, for example, increasing the strut length in the case of thick struts.

As an example, in a 2.0 mm cubic unit cell (where the dimensions in the x, y and z axes are 2.0 mm) with struts of 0.5 mm diameter, the central void is approximately 1.0 mm in width and height. By rotating this unit cell and aligning each strut with a central void, the bulk thickness can be approximately halved. As the struts in this example are increased in diameter, the impact of the rotation is reduced.

Figure 19:
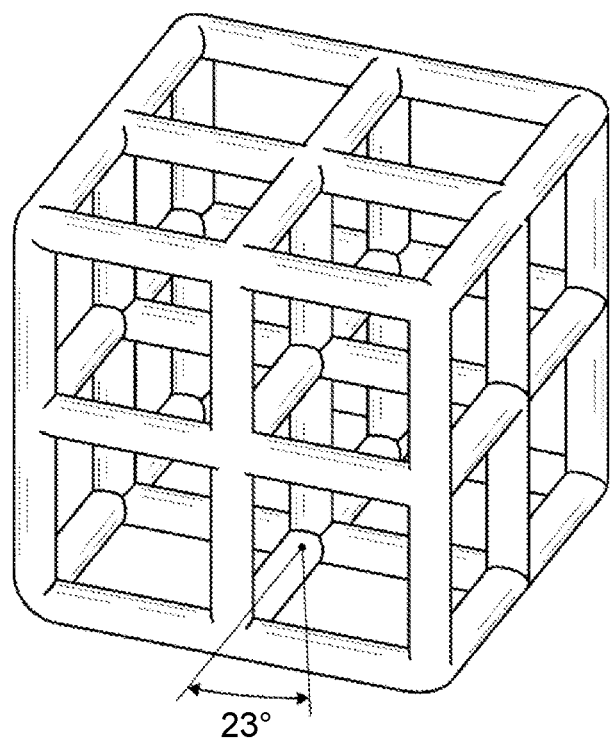
FIG. 19 is a perspective view of an example of the invention using a cubic unit cell and rotated 22 degrees about the z axis and 30 degrees about the x axis from a normal face.

FIG. 19 depicts an exemplary embodiment of the inventive lattice using a cubic unit cell and rotated to a different orientation. In FIG. 19, the lattice has been rotated 22 degrees about the z axis and 30 degrees about the x axis from an origin orientation normal to a cubic unit cell face. Even with less of a rotation about the x and z axis than in FIG. 18, the embodiment of FIG. 19 still maintains a similar dispersion effect with minimal overlap of nodes and struts.

Figure 20:
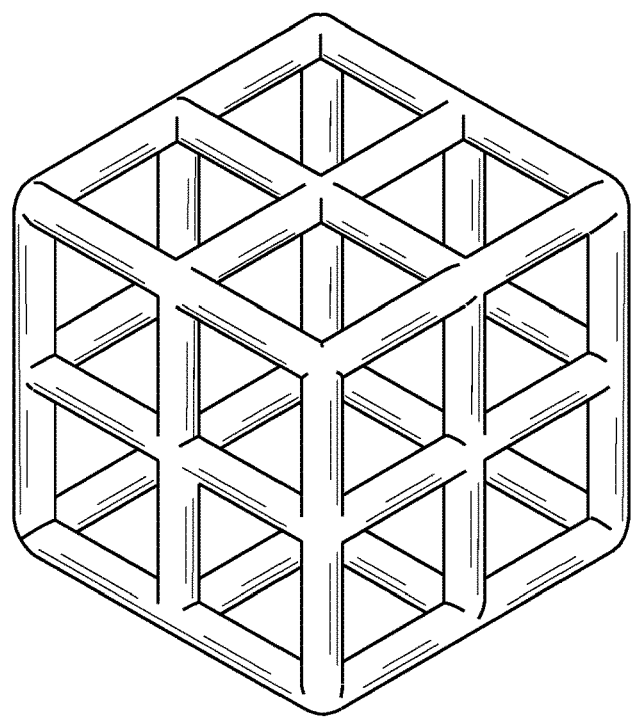
FIG. 20 is a perspective view of an example of the invention using a cubic unit cell and rotated 45 degrees about the z and x axes from a normal face.
Figure 21:
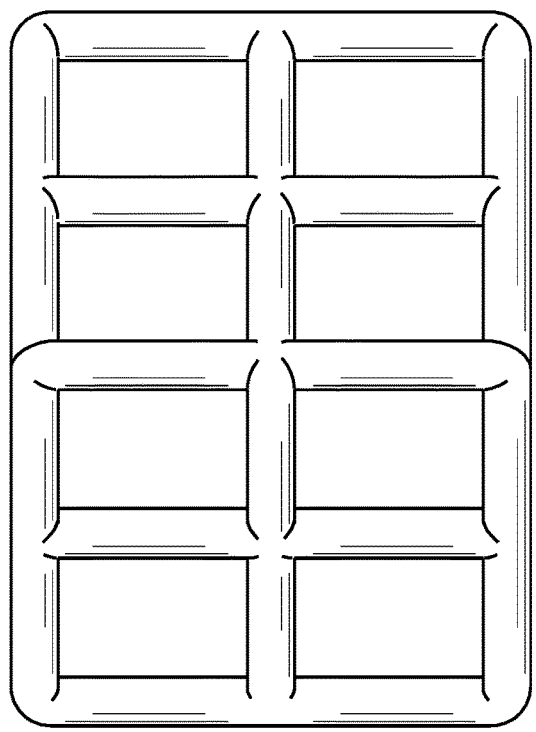
FIG. 21 is a perspective view of an example of the invention using a cubic unit cell and rotated 45 degrees along x axis from a normal face.
Figure 22:
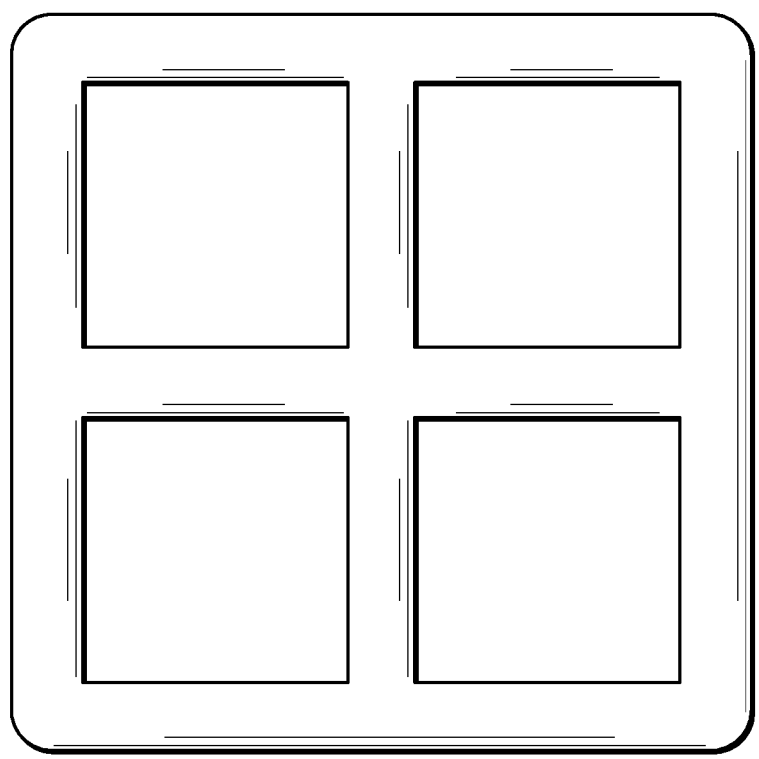
FIG. 22 is a perspective view of an example of the invention using a cubic unit cell with no rotation from a normal face.
Figure 25:
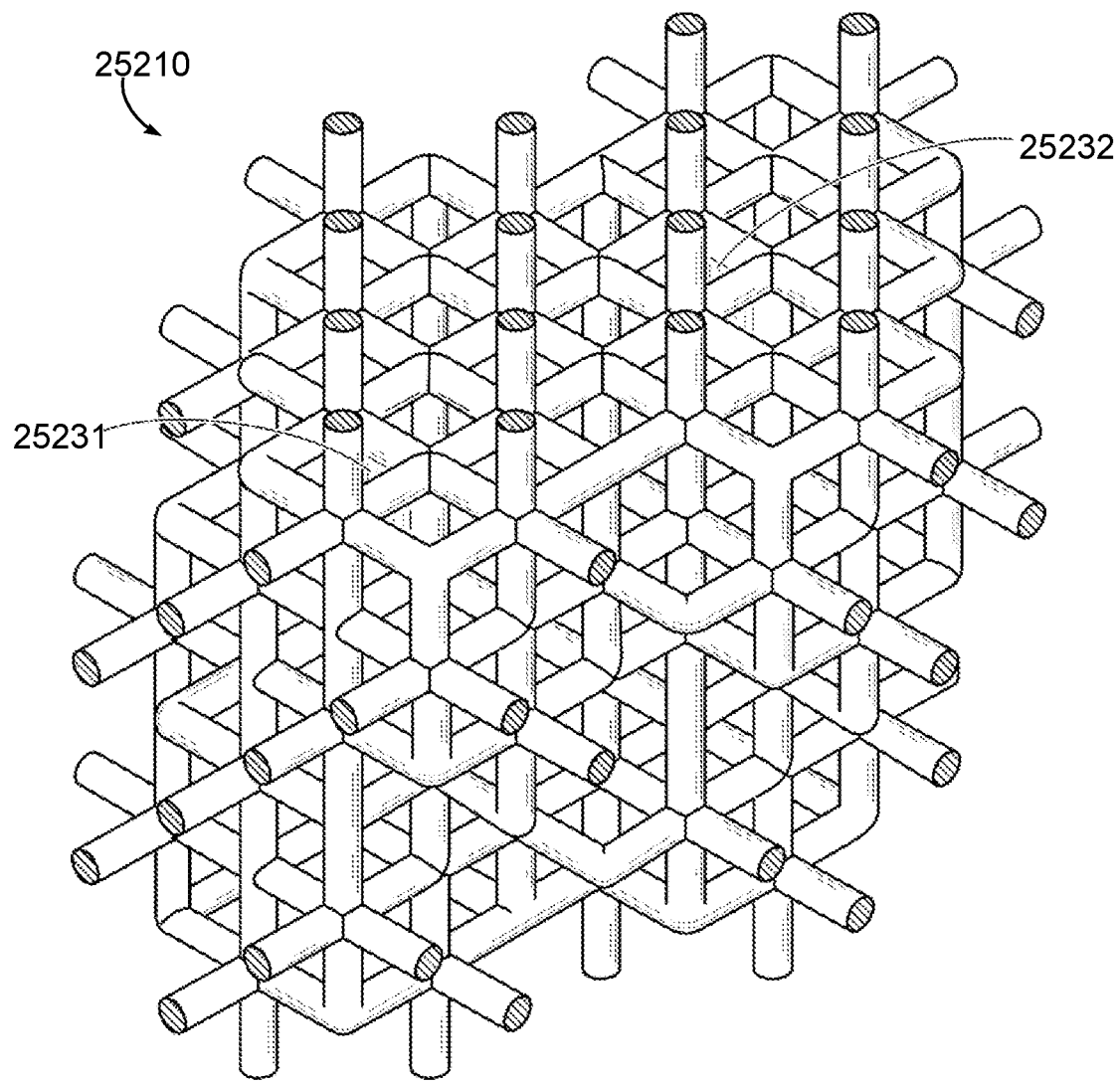
FIG. 25 is an isometric view of a second exemplary embodiment of the variable markers comprised of partially filled unit cells and shown in a misaligned direction.

High disparity embodiments can be achieved through a variety of rotation combinations. FIG. 20 depicts an exemplary embodiment of a lattice of cubic unit cells where the lattice has been rotated 45 degrees about the z axis and 45 degrees about the x axis from an origin orientation normal to a cubic unit cell face. FIG. 21 depicts an exemplary embodiment of a lattice of cubic unit cells where the lattice has been rotated 45 degrees about the x axis from an origin orientation normal to a cubic unit cell face. FIG. 25 depicts an exemplary embodiment of a lattice of cubic unit cells where the lattice has not been rotated from an origin orientation normal to a cubic unit cell face. All of the high relative disparity embodiments are characterized by significant overlap between the nodes and struts of the unit cells. The significant overlap increases the bulk thickness of the structure at certain points in the desired direction, increasing radiopacity in those areas. The high relative disparity embodiments also have areas where no struts or nodes obscure visibility through the structure, increasing the radiolucency in those areas.

A diamond cubic cell has two interpenetrating face centered Bravais lattices within a cubic cell, wherein the Bravais lattices are shifted along a diagonal of the cubic cell by one quarter of the diagonal length. For a single diamond cubic unit cell in an origin orientation where three cubic faces are aligned with the x, y and z axes, respectively, the maximum relative disparity in the desired direction can be achieved when the unit cell is rotated approximately 45 degrees about the z axis from the origin orientation. In some embodiments of a single diamond cubic unit cell in an origin orientation where three cubic faces are aligned with the x, y and z axes, respectively, the maximum relative disparity in the desired direction can be achieved when the unit cell is rotated approximately 45 degrees about the x axis or y axis from the origin orientation. For the same single diamond cubic unit cell, relative maximum dispersion can be achieved at approximately 0 and 90° rotations from the origin orientation. The origin orientation can also be measured relative to a planar face of the cubic cell.

For a single lattice unit cell comprising a repeating generic RDD, MRDD or RDDR structure in an origin orientation where three cubic faces are aligned with the x, y and z axes, respectively, the maximum relative dispersion in the desired direction can occur when the structure is rotated approximately 45 degrees about the z axis from the origin orientation. In some embodiments of a single lattice unit cell comprising a repeating generic RDD, MRDD or RDDR structure in an origin orientation where three cubic faces are aligned with the x, y and z axes, respectively, the maximum relative dispersion in the desired direction can occur when the structure is rotated approximately 45 degrees about the x axis or y axis from the origin orientation. The maximum relative disparity in the desired direction can occur when the single unit cell structure is not rotated at all (0°). While only some types of unit cell structures have been disclosed, there are many types of repeating unit cell structures that can be used to achieve similar results. Possible scaffold geometries that are appropriate include, but are not limited to, rhombic dodecahedron, diamond, dodecahedron, square, pentagonal, hexagonal, octagonal, sctet struts, trunic octa, diagonal struts, other known geometric structures, and rounded or reinforced versions of each geometry. The rotation along the x, y or z axes may be different for different unit cell shapes and materials and can be determined based on the disclosure herein. The amount of rotation about the x, y or z axes will also depend on the aspect ratio of the unit cells and the number of unit cells comprising the structure. As the number of unit cells increases, the nodes and struts will overlap, but through rotating the structure, the overlap of the nodes and struts may be optimized. The use of rounded or reinforced nodes would increase the amount of material present near the nodes, increasing the bulk thickness over areas where the nodes are present. The origin orientation can also be measured relative to a planar face of the cubic cell.

Rotations of structures may be represented relative to a base reference frame or as Euler angles in a reference frame, preferably in a right-hand reference frame about the x, y, and z axes and composed in a rotation matrix. Additional translation of the lattice structure may be achieved in the same step by expanding the matrix. While a Cartesian coordinate system is used as an example reference frame or coordinate system, other reference frames could be appropriate and could be more efficient, depending on the structure being analyzed.

These angles are determined based on the aspect ratios and geometries of the particular lattice structure. Specifically, the strut diameter, cell height, cell width, cell depth, and overall thickness, length, and height of the device are key parameters for solving rotation angles in x, y, and z axes, according to the following:

$$R(x,y,z,\alpha,\beta,\gamma)=F(h,w,d,T,H,L)$$

Where:
d=Strut diameter
h=Cell height
w=Cell width
d=Cell depth
T=Device Thickness
H=Device Height
L=Device Length In some embodiments, the rotation of a structure can be referred to based on a rotation in degrees about an axis. The high x-ray lucency structures disclosed herein, in some embodiments, are achieved by rotating the structure from an origin orientation between and including zero degrees to 180 degrees in either direction about an axis. In some embodiments, the high x-ray lucency structures are achieved by rotating the structure from an origin orientation between and including zero degrees to 360 degrees about an axis. In some embodiments, the high x-ray lucency structures are achieved by rotating the structure from an origin orientation between and including 35 degrees to 55 degrees in either direction about an axis.

Some examples of lattices comprising repeating geometric unit cells that have been optimized for lucency were disclosed above, but the method used to design the exemplary embodiments can be applied to unit cells of other specifications using a manual or computer aided method disclosed herein. The method of optimizing a structure for lucency is described herein as a method of design and manufacture. The method of optimizing a structure for lucency disclosed herein can be applied to many types of structures, including but not limited to, lattice structures with repeating geometric patterns and porous structures with either repeating structures or random structures. While the methods disclosed generally design the orientation of the lattice first and then produce the lattice in a method of manufacture, the steps could just as easily be reversed. A lattice may be first manufactured and then oriented using the method of design. For instance, a lattice may be first manufactured and then, by using the characteristics of the manufactured structure, a user may use the method of design to orient the structure for a lucency quality. The lattice could then be rotated to that orientation and cut, machined or formed into its final shape.

The method of design can be performed through a manual process either by manufacturing a structure and performing evaluations on a physical model or performed in a software that generates the structure within a specified volume of the implant at a user-defined unit cell orientation and then displays the result for visualization. In a first exemplary method of design, the user iterates the process, changing the orientation parameters for the unit cell, regenerating the structure, assessing the achieved bulk thickness of the device, and the uniformity of that thickness across the implant. Once the user is satisfied with the minimally achieved bulk thickness and its uniformity, the parameters and final structure is accepted. Computer aided design (hereinafter "CAD") or other three-dimensional (hereinafter "3D") models of the unit cell structure can also be used as a starting point to identify optimal rotations or starting points.

The method of design can also be performed using a process aided with algorithms and visualizations tools. In a second exemplary method of design, a user would:

1. Generate or import a bulk volume repeating structure in a form capable of analysis by an analysis tool. An analysis tool, as used herein, refers to any application or process used to analyze data. An analysis tool could be an application or program capable of analyzing multiple variables, such as MATLAB®, FreeMat, Octave, Mathematica®, or any comparable or custom software. The analysis tool may comprise a different program, comprise a user generated program or comprise any other program, device, person or persons capable of analyzing multiple variables. The analysis tool can also be one or more people visually analyzing a repeating structure. The form capable of analysis is different for each type of analysis tool available. For example, in an application or program, the repeating structure would likely need to be imported or a facsimile created within the capabilities of the application or program. If the analysis tool is a person, one form capable of analysis would be a manufactured repeating unit cell structure.

2. Propagate the bulk volume at some orientation throughout the specific device volume or perform on a raw structure independent of specific device constraints. The bulk volume can alternatively be sectioned to the appropriate dimensions of a selected implant type.

3. Determine the uniformity of the bulk thickness from a desired direction. The uniformity of bulk thickness can be determined through multiple methods, including by measuring the bulk thicknesses across the bulk volume in the desired direction(s) for viewing and then calculating the uniformity of bulk thickness. In some methods, the bulk thicknesses may be visualized as a 2D heat map of the structure in the desired direction(s). In some methods, the coefficient of determination ($R^2$) would be a good indicator of the uniformity of bulk thickness.

4. Iterate across rotations of the bulk volume to identify the desired uniformity.

5. The parameters are captured, and a final structure is generated.

This method of design does not need to be performed in the precise order described above and may also be automated. A first possibility is simply by performing all possible combinations of angle rotations in a Monte Carlo simulation. A second, by applying artificial intelligence and machine learning algorithms (k-means, regression, Support Vector Machines, neural networks, or other such techniques) to achieve the optimal angle of rotation for a specific structure.

The methods of increasing lucency of implants can also include the step of selecting a focal length to determine a region of interest on an implant. The focal length, as used herein, refers to the expected distance between an imaging device and the implant during imaging during or after implantation. Many x-rays are taken from a focal length of about 2-2.5 feet, but this distance could be adjusted to accommodate a particular x-ray machine that deviates from the usual distance. In many x-ray machines, a distance of about 5 feet is used between an x-ray emitter and receiver, with a patient located about an equal distance from the emitter and receiver. The x-ray emitter is commonly moved relative to a patient to chance the field of view or amount of detail in the x-ray image. The focal length helps identify a specific area of interest in the implant for imaging. When imaging is taken with an emitter about 2-2.5 feet away from a patient, the area of interest can be more lucent than the remainder of the implant due to the viewing angle of the x-ray machine.

In some methods, an infinite focal length can be used to determine the optimal lucency property angle for an entire side of an implant. In some methods, where a focal length of some value is used, the implant can have a rotation gradient to provide an even lucency effect, even with a focal length of less than infinite. A rotation gradient could be provided with a lattice that rotated the unit cells relative to the unit cell orientation around a focal point. The rotation gradient could compensate for x-ray machines with a particularly short focal length or to maximize the imaging area. A maximized imaging area could be useful to provide a broader image of the implant during and after implantation. A maximized imaging area could also be useful to display internal serialization, numerals, letters, or identification patterns (e.g., a barcode or a matrix barcode) over a broad area of an implant.

These algorithms can be expanded further to include variations of the unit cell size and strut thickness within specified constraints to further optimize the structure. Such constraints may include bounded ranges on each parameter, overall device volumetric density, construct stiffness, or other relational conditions between or external to these parameters.

In a third exemplary method of design, a user would:

1. Choose a repeating geometric structure and material that meets the structural requirements.

2. Pick an origin orientation for a bulk volume comprising the selected repeating geometric structure and material.

3. Run a multivariable analysis for uniformity of bulk volume from the desired direction(s) where the structure is rotated from its origin orientation by at least 90 degrees along the x, y and z axes. In cases of asymmetry, it may be necessary to rotate in the positive and negative directions about each axis (e.g. a rotation of 90 degrees and −90 degrees about an axis). In unit cells where a reduction in average bulk thickness can be achieved through a rotation, it can be beneficial to run a multivariable analysis for average bulk thickness as well.

4. Use the multivariable analysis to determine the rotation from the origin orientation that produces desirable lucency characteristics in the desired direction(s) (i.e. dispersion).

This method of design represents a series of steps that may be taken to optimize a preselected repeating geometric lattice structure for lucency in a desired direction. These steps do not need to be taken in order and additional variables may be considered before, after or during the method of design to optimize a repeating geometric lattice for a particular application. For example, the method of design could include the cell size or strut thickness as variables rather than an input value in the first step, or account for structures with variable cell size or strut thickness. Other variables or constraints may also be considered within this method of design.

In some embodiments, voids may be included within the implant to reduce the bulk thickness in the desired direction. Generally, a lower bulk thickness is better for lucency and the inclusion of voids in the desired direction can reduce the bulk thickness in that direction.

The use of the above disclosed lattice and method of design can also be used to design variable markers in some embodiments. Variable markers in implants can be useful during implantation to assist the surgeon in positioning. The structures of the present invention may be rotated locally to increase the bulk density in certain locations to provide one or more areas of radiopacity, increased radiodensity, radiolucency, increased radiolucency, lucency or increased lucency. As used herein, in reference to markers, increased radiodensity indicates that an area has a higher radiodensity than the immediately surrounding area. The exemplary embodiments disclosed herein may also include radiopaque or increased radiodensity variable markers constructed using various techniques, including but not limited to, filling in certain cells, providing thicker struts on certain cells, or providing thicker or reinforced nodes where certain struts meet. In some embodiments, the variable markers are a configured as a particular shape, such as a circle, rectangle, cross or "X" mark to assist in the location or alignment of the implant. In some embodiments, variable markers in the shape of one or more characters (letters, numerals, etc.), a name or a logo may be included in the implant. When a variable marker includes characters, a name or a logo oriented to face in the desired direction, they can be visible on an x-ray as a lighter region. In the alternative, a void, area of lower density, or area of lower bulk thickness may be provided to create a darker area on an x-ray representing a character, a name or a logo. When including a variable marker in the shape of one or more characters, they can be added through the addition of a block of material or a void of material in the open cell structure in the shape of the desired character(s). In some embodiments, the variable markers may represent a barcode, QR (matrix) barcode, or other data encoding method such as filling of specific cells within the lattice as a method of device serialization.

The variable markers disclosed herein can be used with the aforementioned lattice structures with high x-ray lucency to improve the visibility of the variable markers in metallic materials. The variable markers can also be used in a lattice structure with a rotation gradient angled towards an x-ray focal point to provide a larger area on an implant with high x-ray lucency.

In some embodiments, the variable markers may be configured so that the variable markers become more lucent during misalignment and more opaque when properly aligned (or vice versa). It would be useful to provide variable markers that increase or decrease in lucency when rotated to provide a surgeon a clear indication of when an implant is aligned or misaligned. In some embodiments, the variable markers may comprise a biocompatible lattice where the variable markers comprise orientation features relative to other variable markers.

Figure 23:
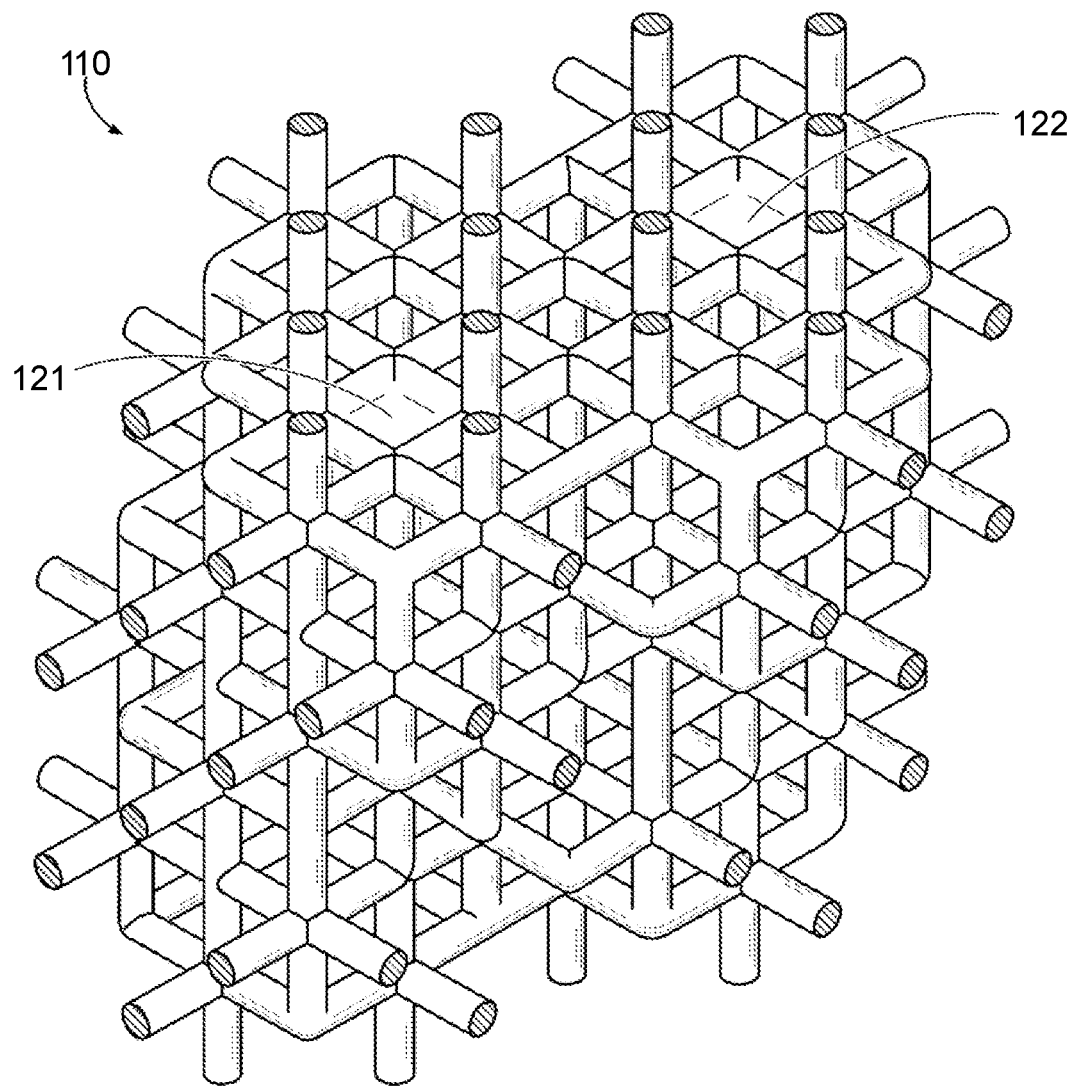
FIG. 23 is an isometric view of a first exemplary embodiment of the variable lucent markers (hereinafter "variable markers") comprised of filled unit cells and shown in a misaligned direction.
Figure 24:
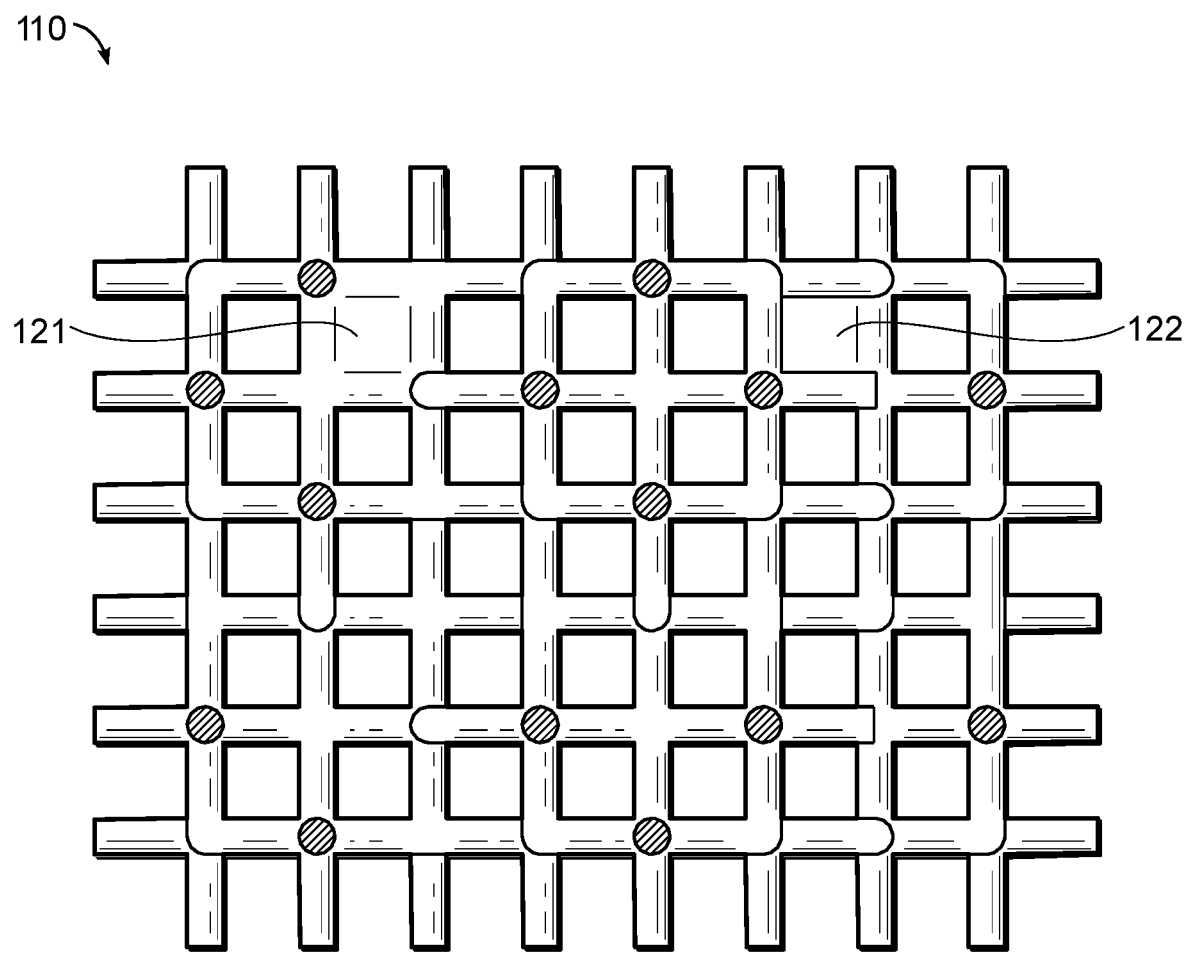
FIG. 24 is a side view of a first exemplary embodiment of the variable markers comprised of filled unit cells and shown in a misaligned direction.

FIGS. 23-24 illustrate a first exemplary embodiment of the variable markers that uses selectively filled unit cells. Variable radiodensity as used in reference to the variable markers means that the markers have at least a first radiodensity when viewed from a first direction and a second radiodensity when viewed from a second direction. The variable markers may optionally have additional radiodensities when viewed from additional directions.

FIG. 23 illustrates an isometric view of the first exemplary embodiment of the variable markers shown in a lattice 110. The lattice 110 uses a repeating square unit cell, however other types of unit cells, as noted earlier, can be substituted. Within the lattice 110, two solid unit cells 121 & 122 have been added. The solid unit cells 121 & 122 can be solidly filled so that there are no voids within the planes that define the cell walls, having a volumetric density of about 100%. They may optionally contain a central void, be filled with a material with a volumetric density of less than 100%, only partially filled or filled with a material with a volumetric density of between and including 0% to 30%. In the isometric view of FIG. 23, the solid unit cells 121 & 122 are at a misalignment viewing direction, meaning that the solid unit cells 121 & 122 will show up as more radiolucent than in an aligned viewing direction.

FIG. 24 depicts a side view of the first exemplary embodiment of the variable markers. The side view of the lattice 110 is shown from a second misalignment direction where the location of the solid unit cells 121 & 122 do not overlay one another in this view. As a misalignment viewing direction, the solid unit cells 121 & 122 will show up as more radiolucent than in an aligned viewing direction. In the first exemplary embodiment, the aligned direction is 90 degrees in either direction about a vertical axis from the side view in FIG. 24. If the lattice 110 is rotated by 90 degrees in either direction about a vertical axis from the side view in FIG. 24, the solid unit cells 121 & 122 will overlay one another. With the volume of solid unit cells 121 & 122 overlapping, the area of the overlapped area will appear much more radiopaque than in a misalignment direction. Overlay, as used herein, refers to when a marker is at least partially in the same location relative to a viewing direction. For instance, in an aligned direction, a marker closer to the viewer in a viewing direction could overlay a marker further from the viewer, creating a localized area with higher or lower lucency. If the markers have a higher volumetric density that the surrounding structure, any marker overlay over another will create a localized are of lower lucency. If the markers have a lower volumetric density that the surrounding structure, any marker overlay over another will create a localized area of higher lucency. An aligned direction can be characterized by one marker only partially overlaying another marker. A misaligned direction could be characterized by one marker partially overlaying another marker, but not completely overlaying the other marker.

Figure 26:
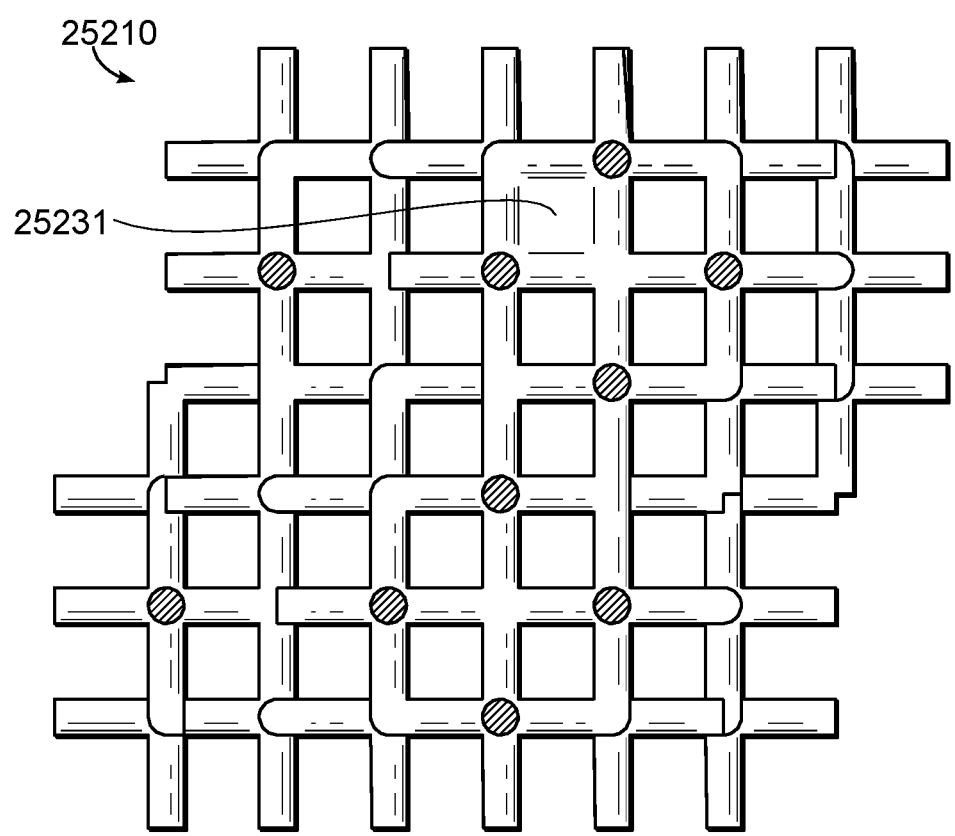
FIG. 26 is a side view of a second exemplary embodiment of the variable markers comprised of partially filled unit cells and shown in an aligned direction.
Figure 27:
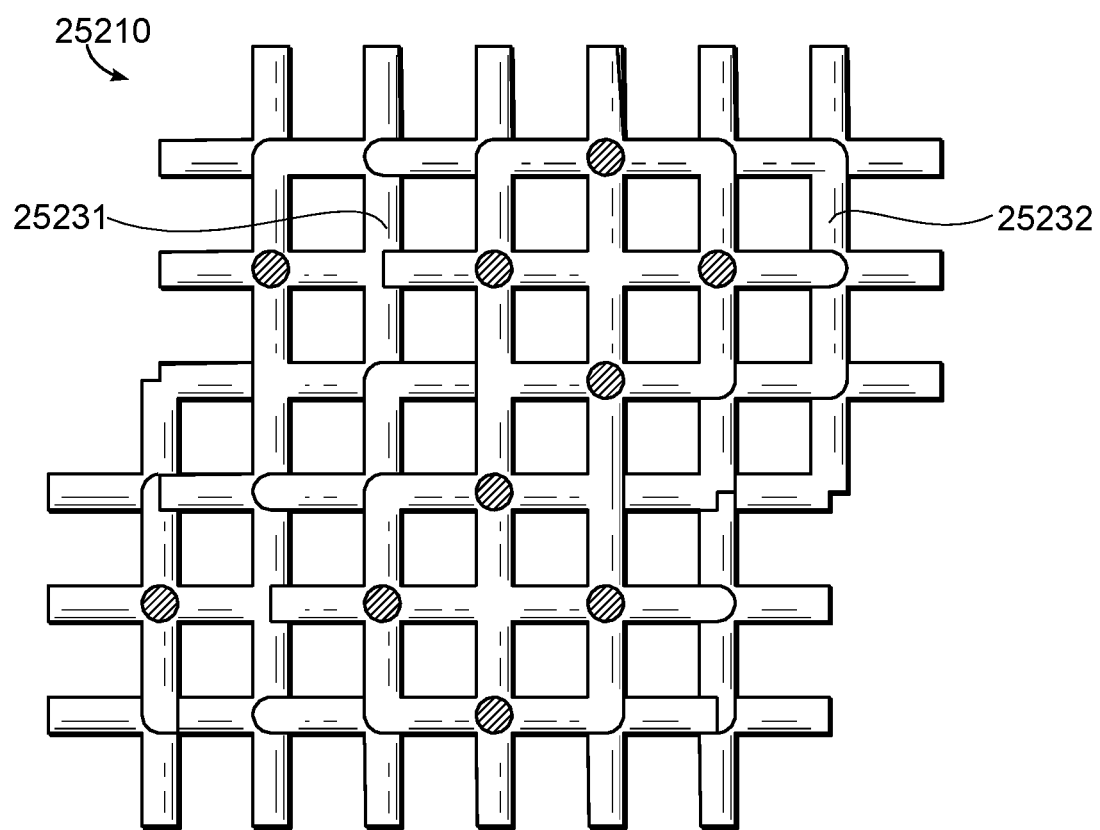
FIG. 27 is an alternative side view of a second exemplary embodiment of the variable markers comprised of partially filled unit cells and shown in a second aligned direction.

FIGS. 25-27 illustrates a second exemplary embodiment of the variable markers that employs partially filled unit cells. FIG. 25 illustrates an isometric view of the second exemplary embodiment of the variable markers shown in a lattice 25210. The lattice 25210 used is a repeating square unit cell, however other types of unit cells, as noted earlier, can be substituted. Within the lattice 25210, two partially filled unit cells 25231 & 25232 have been added. The partially filled unit cells 25231 & 25232 can be solidly filled so that there is are no voids within the filled area. The filled area may optionally contain one or more voids, be filled with a material with a volumetric density of less than 100% or only partially filled. In the isometric view of FIG. 25, the partially filled unit cells 25231 & 25232 are at a misalignment viewing direction, meaning that the partially filled unit cells 25231 & 25232 will show up as more radiolucent than in an aligned viewing direction.

FIG. 26 is a side view of the second exemplary embodiment of the variable markers. The side view of the lattice 25210 is shown from an aligned direction where the location of partially filled unit cells 25231 & 25232 overlap in this view. The partially filled unit cell 25232 is located behind partially filled unit cell 25231 in this view so that when viewing the variable markers in the aligned direction, the x-ray would need to travel through both partially filled unit cells 25231 & 25231, decreasing their radiolucency.

FIG. 27 illustrates an alternative side view of the second exemplary embodiment of the variable markers. The alternative side view of the lattice 25210 is shown from a second alignment direction that can be used to highlight or identify a second direction to a user. The partially filled unit cells 25231 & 25232, in this example, are comprised of a filled unit cell wall, with substantially square faces in the aligned direction and narrow edges in the second alignment direction. The filled unit cell walls have a greater radiodensity from the narrow edge (their planar direction) than from the substantially square faces because of the increased amount of bulk thickness in the planar direction. The filled unit cell walls also have an elongated shape when viewed in the planar direction rather than a substantially square shape when viewed in a direction normal to the planar direction. Therefore, when viewing a single filled wall from a narrow edge or planar direction, it will be elongated and be less radiolucent than the same filled wall viewed from the direction of the square faces. The difference in radiodensity and appearance when viewed in the aligned direction or second aligned direction can be amplified by adding additional overlapping filled unit cell walls to increase the bulk thickness of the material in the aligned or second aligned directions.

Figure 28:
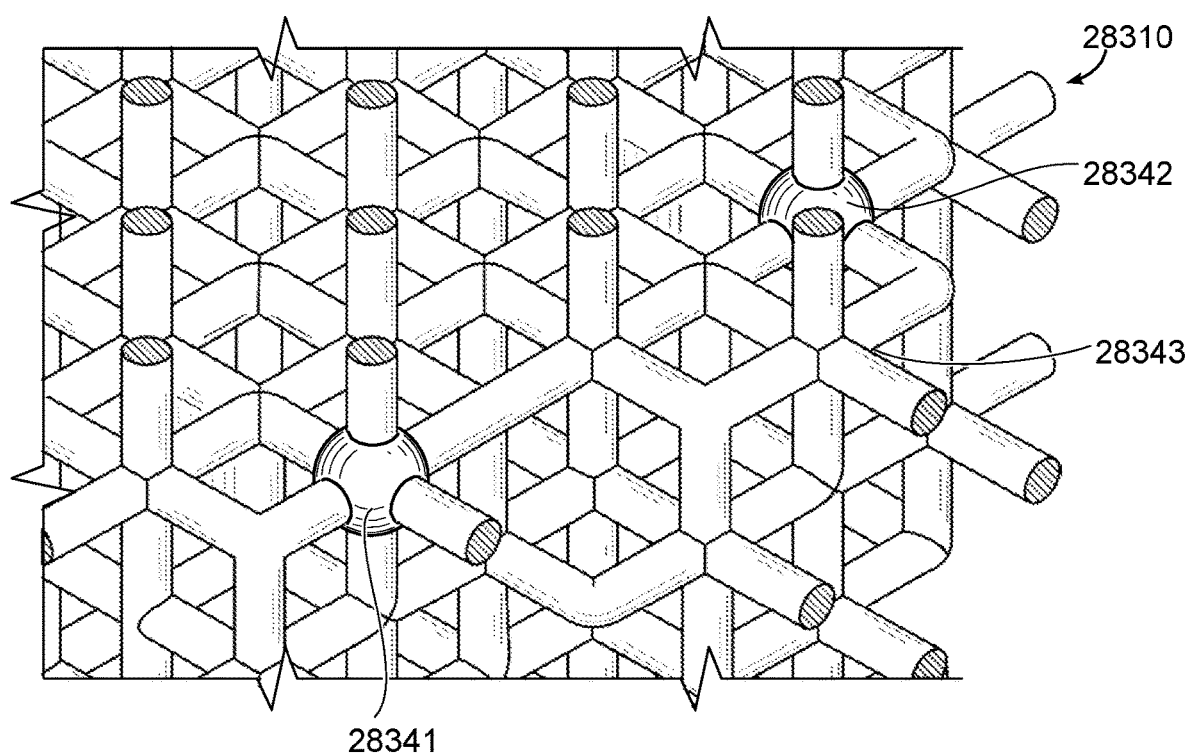
FIG. 28 is an isometric view of a third exemplary embodiment of the variable markers comprised of enlarged nodes and shown in a misaligned direction.

FIGS. 28-31 illustrate a third exemplary embodiment of the variable markers that uses selectively enlarged nodes. FIG. 28 illustrates an isometric view of the third exemplary embodiment of the variable markers shown in a lattice 28310. The lattice 28310 comprises a repeating square unit cell, however other types of unit cells, as noted earlier, can be substituted. Within the lattice 28310, three enlarged nodes 28341-28343 have been added. The enlarged nodes 28341-28343 can be solidly filled so that there is are no voids within the filled area and a volumetric density of about 100%. The filled area may optionally contain one or more voids, be filled with a material with a volumetric density of less than 100%, only partially filled, or filled with a material with a volumetric density of between and including 0% to 30%. In the isometric view of FIG. 28, the enlarged nodes 28341-28343 are at a misalignment viewing direction, meaning that the enlarged nodes 28341-28343 will show up as more radiolucent than in an aligned viewing direction.

Figure 29:
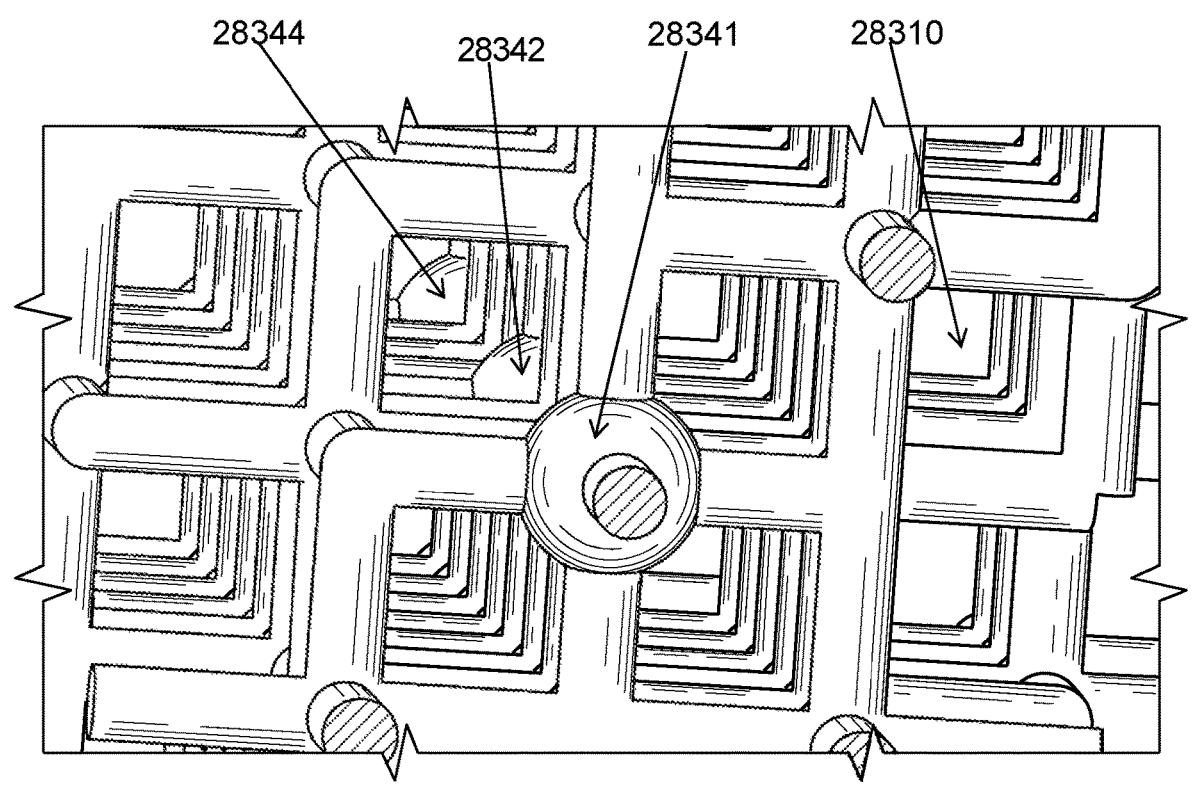
FIG. 29 is an offset side view of a third exemplary embodiment of the variable markers comprised of enlarged nodes and shown in a misaligned direction that is approaching an aligned direction.

FIG. 29 depicts an offset side view of a third exemplary embodiment of the variable markers. In FIG. 29, the offset side view is a misalignment direction that is approaching a side aligned direction. In the third exemplary embodiment, the aligned direction occurs when the lattice 28310 is rotated so that one or more enlarged nodes 28341-28344 are overlapping. In FIG. 29, the enlarged nodes, 28341, 28342 & 28344 partially overlay one another, but do not fully overlay one another.

Figure 30:
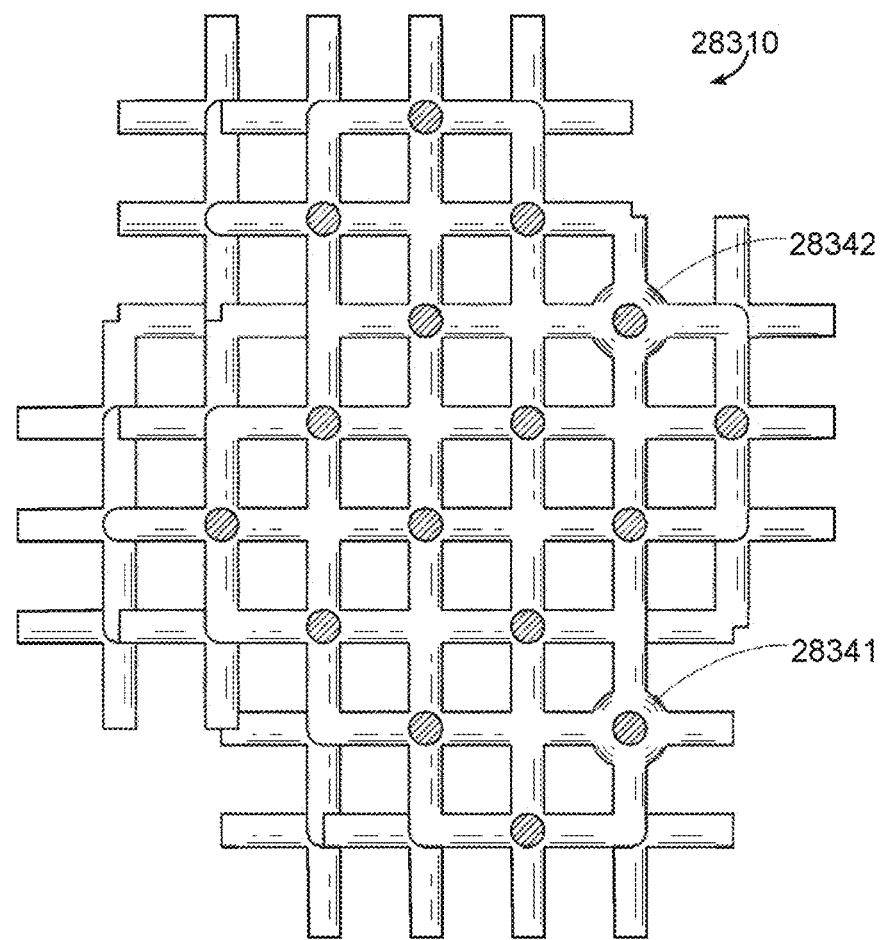
FIG. 30 is a top view of a third exemplary embodiment of the variable markers comprised of enlarged nodes and shown in an aligned direction.

FIG. 30 depicts a top view of the third exemplary embodiment of the variable markers. The top view can be an alternative aligned direction if further enlarged nodes are located directly below enlarged nodes 28341 & 28342. If no additional enlarged nodes are located below enlarged nodes 28341 & 28342, the top view would be an additional misalignment view.

Figure 31:
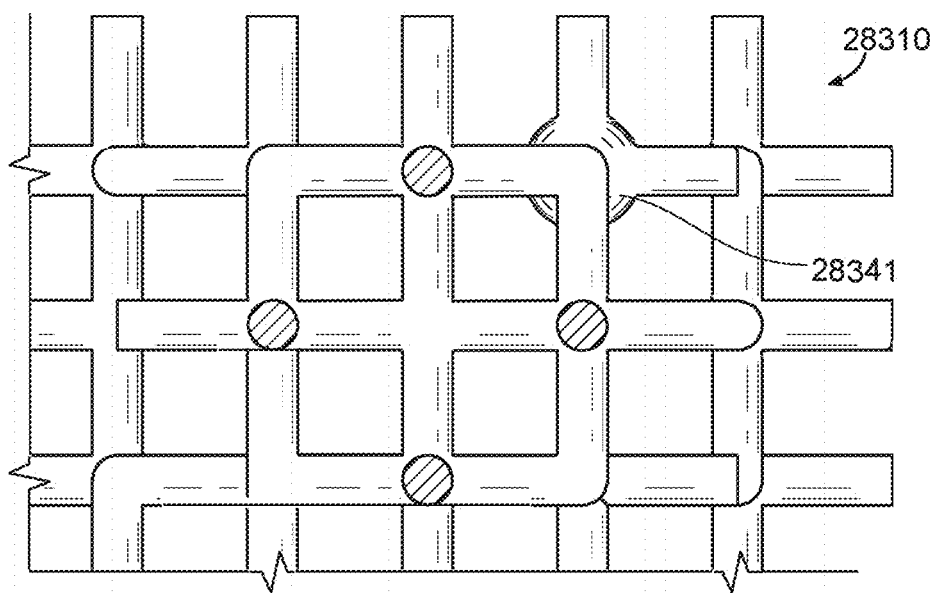
FIG. 31 is a side view of a third exemplary embodiment of the variable markers comprised of enlarged nodes and shown in an aligned direction.

FIG. 31 depicts a side view of the third exemplary embodiment of the variable markers. The side view of the lattice 28310 is shown from an aligned direction where the location of enlarged nodes 28341 & 28342 overlap in this view. Enlarged node 28342 is located behind enlarged node 28341 in this view so that when viewing the variable markers in the aligned direction, the x-ray would need to travel through both enlarged nodes 28341 & 28342, decreasing their radiolucency.

Figure 32:
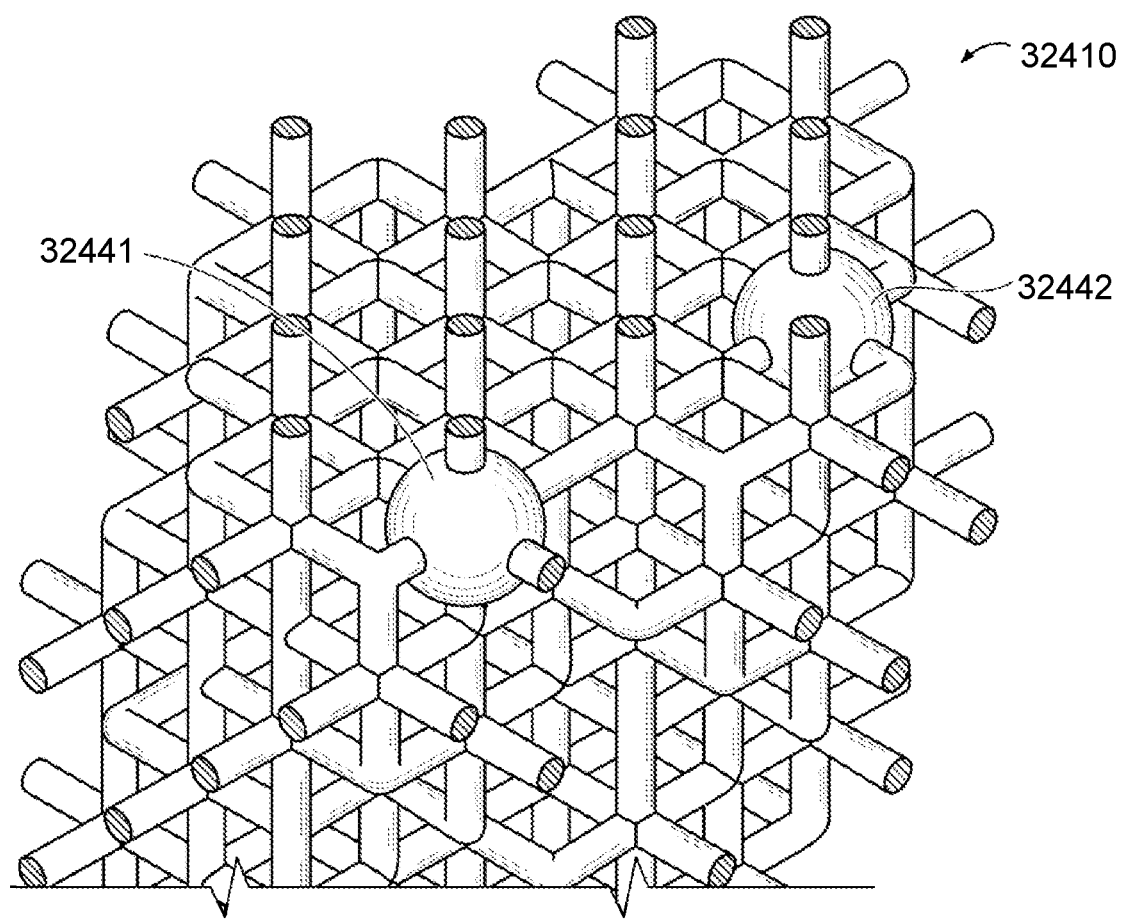
FIG. 32 is an isometric view of a fourth exemplary embodiment of the variable markers also comprised of enlarged nodes and shown in a misaligned direction.

FIG. 32 depicts a fourth exemplary embodiment of the variable markers that uses selectively enlarged nodes. FIG. 32 depicts an isometric view of the fourth exemplary embodiment of the variable markers shown in a lattice 32410. The lattice 32410 used is comprised of a repeating square unit cell, however other types of unit cells, as noted earlier, can be substituted. Within the lattice 32410, two enlarged nodes 32441 & 32442 have been added. The enlarged nodes 32441 & 32442 can be solidly filled so that there is are no voids within the filled area, having a volumetric density of about 100%. The filled area may optionally contain one or more voids, be filled with a material with a volumetric density of less than 100%, only partially filled or filled with a material with a volumetric density of between and including 0% to 30%. In the isometric view of FIG. 32, the enlarged nodes 32441 & 32442 are at a misalignment viewing direction, meaning that the enlarged nodes 32441 & 32442 will show up as more radiolucent than in an aligned viewing direction.

For the fourth exemplary embodiment, the aligned directions would fall in a lateral direction. One aligned direction could be viewed by rotating the lattice 410 from the orientation in FIG. 32 by about 45 degrees about the x axis and about 45 degrees about the z axis. A second aligned direction could be viewed by rotating the lattice 32410 from the orientation in FIG. 32 by about 45 degrees about the x axis and about 135 degrees about the z axis.

Figure 33:
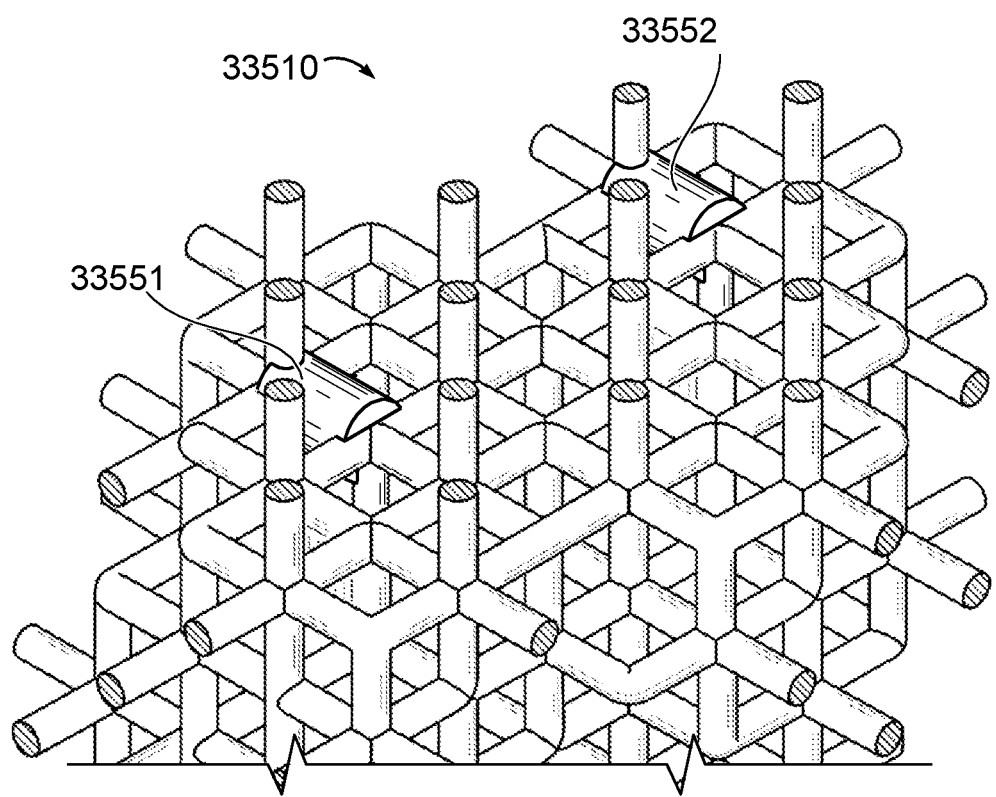
FIG. 33 is an isometric view of a fifth exemplary embodiment of the variable markers comprised of enlarged struts and shown in a misaligned direction.
Figure 34:
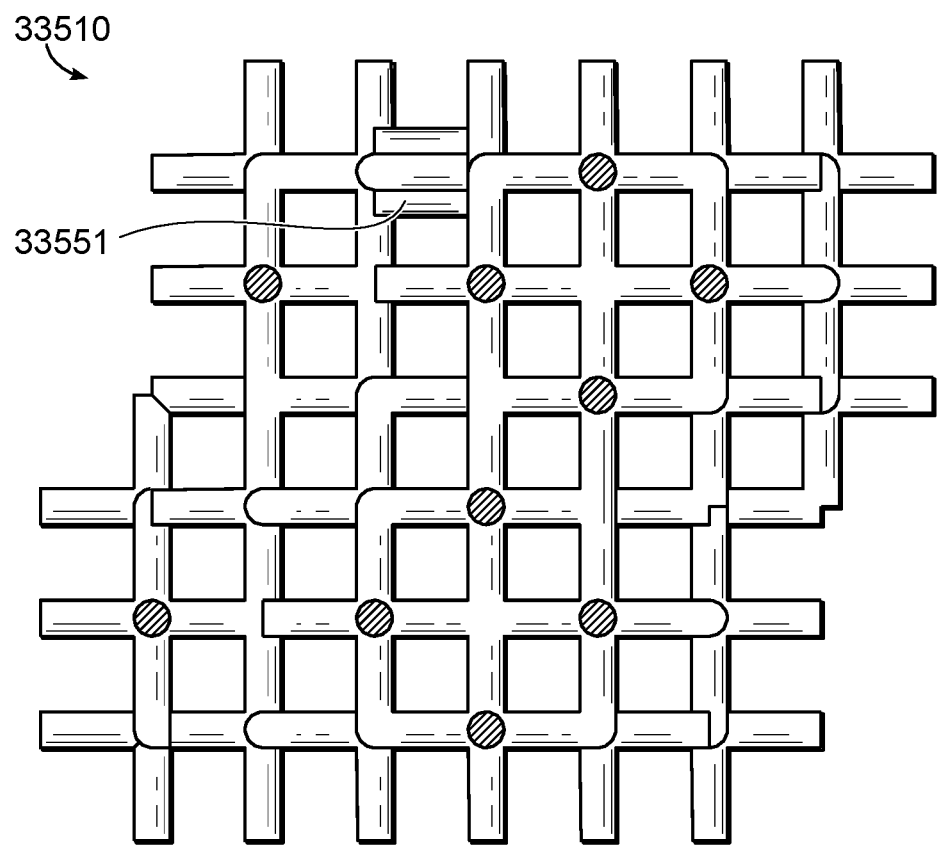
FIG. 34 is a side view of a fifth exemplary embodiment of the variable markers comprised of enlarged struts and shown in an aligned direction.

FIGS. 33-34 illustrate a fifth exemplary embodiment of the variable markers that uses selectively enlarged struts. FIG. 33 illustrates an isometric view of the fifth exemplary embodiment of the variable markers shown in a lattice 33510. The lattice 33510 used is comprised of a repeating square unit cell, however other types of unit cells, as noted earlier, can be substituted. Within the lattice 33510, two enlarged struts 33551 & 33552 have been added. The enlarged struts 33551 & 33552 can be solidly filled so that there is are no voids within the filled area, having a volumetric density of about 100%. The enlarged struts may also be employed using other characteristics, including but not limited to, partially enlarged struts, enlarged struts between adjacent nodes, enlarged struts on an area centered over a node, struts smoothly integrated into the surrounding structure and/or struts sharply integrated into the surrounding structure. The filled area may optionally contain one or more voids, be filled with a material with a volumetric density of less than 100%, only partially filled or filled with a material with a volumetric density of between and including 0% to 30%. In the isometric view of FIG. 33, the enlarged struts 33551 & 33552 are at a misalignment viewing direction, meaning that the enlarged struts 33551 & 33552 will show up as more radiolucent than in an aligned viewing direction.

FIG. 34 is a side view of the fifth exemplary embodiment, showing the lattice 33510 in an aligned direction. In the aligned direction, the enlarged strut 33551 fully overlays the enlarged strut 33552 so that only enlarged strut 33551 is visible. The opposite side would also be an aligned direction in this embodiment.

The variable markers disclosed herein can be implemented in various types of implants, including the high x-ray lucency lattice structures disclosed herein, other porous structures and substantially solid structures. The variable markers could be used in some solid metallic structures and in some solid polymer structures, particularly PEEK structures.

The variable markers can be designed relative to the lucency of the bulk volume they are connected to, fixed to or contained within. The relative lucency of the bulk volume is best determined as an average baseline lucency representing the average lucency of the bulk volume in a given direction without the inclusion or any variable markers. The average baseline lucency can be taken across the entire side of a bulk volume if using an infinite focal length, or across a focal area when using a finite focal length. Once the variable markers are included with the bulk volume, a second average lucency may be taken of the bulk volume and the variable marker. It is preferable for the inclusion of a variable marker to change the average lucency of the bulk volume by 35% or less than the average baseline lucency when viewed in a misaligned direction. It is more preferable for the inclusion of a variable marker to change the average lucency of the bulk volume by 15% or less than the average baseline lucency when viewed in a misaligned direction. In some embodiments, it is preferable for the inclusion of a variable marker to change the average lucency of the bulk volume by an amount between and including 4% and 12% compared to the average baseline lucency when viewed in a misaligned direction.

The variable markers can cause a change from the average baseline lucency that can be quantified in an aligned direction. When the variable markers are in an aligned direction, they can cause a localized change in lucency compared to the average baseline lucency. It is preferably for the variable markers to cause a localized change in lucency of at least 1% compared to the average baseline lucency. In some embodiments, it is preferable for the variable markers to cause a localized change in lucency of at least 4% compared to the average baseline lucency. In some embodiments, it is preferable for the variable markers to cause a localized change in lucency of at least 15% compared to the average baseline lucency. The localized change in lucency refers to a measure of lucency taken at an area local to the variable marker and used in comparison with the average baseline lucency. The area local to the variable marker can be measured as the visible area of a variable marker when viewed in an aligned direction. In some embodiments, the area local to the variable marker can be measured as an area including a variable marker when viewed in an aligned direction and including an area near the variable marker of about one to ten times the visible area of the variable marker when viewed in an aligned direction.

The variable markers disclosed herein can comprise a marker with various volumetric density properties. In some embodiments, the variable markers have a volumetric density of about 100%. In some embodiments, the variable markers have a volumetric density of less than 100%. In some embodiments, the variable markers have a volumetric density of between and including 0% to 30%. In some embodiments, the variable markers have a volumetric density of between and including 0% to 25%.

Figure 35:
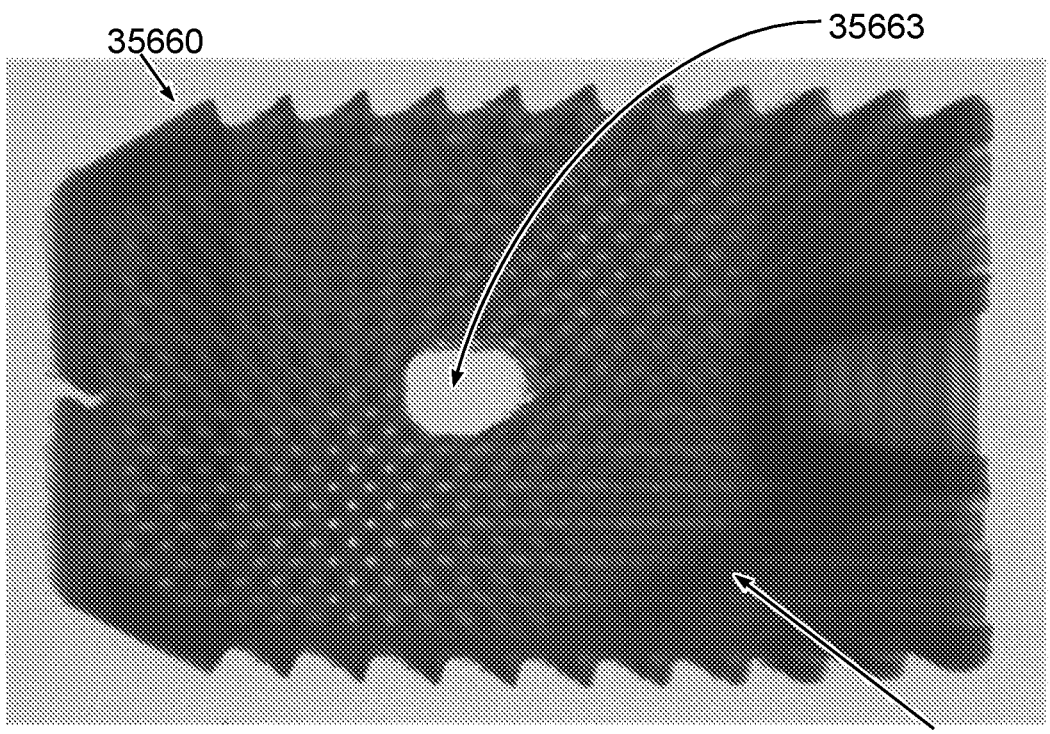
FIG. 35 is a side view of an exemplary interbody fusion implant incorporating variable markers shown in an aligned direction.
Figure 36:
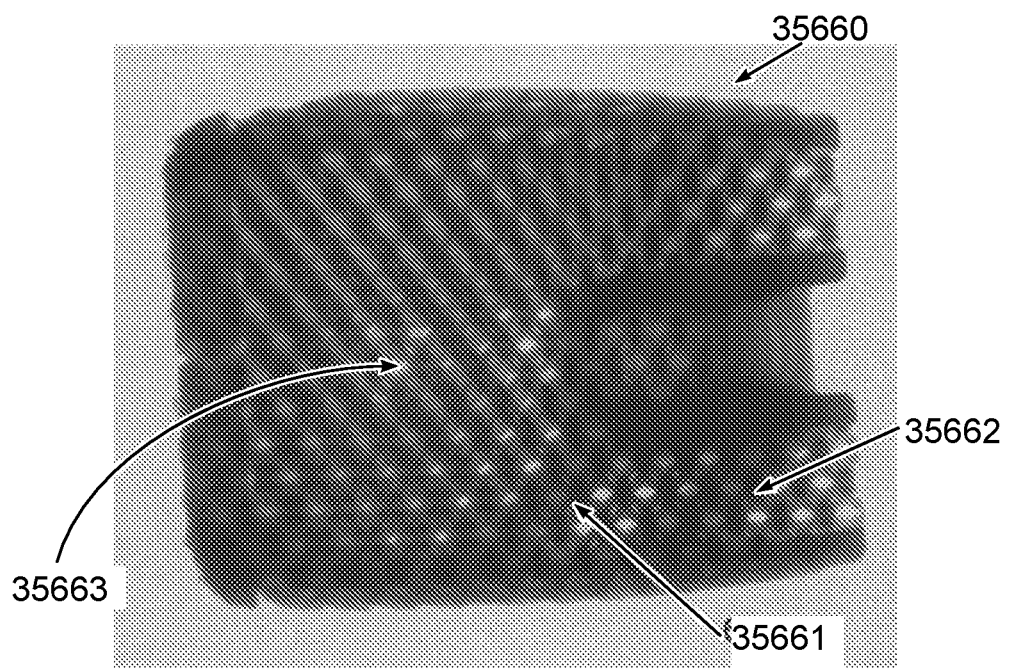
FIG. 36 is a perspective view of an exemplary interbody fusion implant incorporating variable markers shown in a misaligned direction.

FIGS. 35-36 illustrates an example of an implant 35660 that includes diagonal variable markers 35661 & 35662. FIG. 35 is a side view of the implant 35660 in an aligned direction. In the aligned direction, the diagonal variable marker 35661 fully overlays the diagonal variable marker 35662 so that the area is less radiolucent than the surrounding body of the implant. The diagonal variable markers 35661 & 35662 in the exemplary embodiment comprise struts with a diameter of approximately one mm and configured to overlap at the aligned direction. In the side view of FIG. 35, the aligned direction, the diagonal variable marker 35661 is largely radiopaque due to a significant overlap with the diagonal variable marker 35662. When the diagonal variable markers 35661 & 35662 are viewed in the aligned direction, the closer marker to the viewer partially or fully overlays the more distant marker from the viewer. FIG. 36, where the implant 35660 is rotated approximately 45 degrees about the z axis from its position in FIG. 35 to a misaligned direction, the diagonal variable markers 35661 & 35662 become more radiolucent than when viewed from the FIG. 35 orientation as the amount of overlap between the struts decreases.

The implant 35660 also includes another variable marker 35663 configured for providing a measure of alignment. In the aligned view of FIG. 35, the variable marker 35663 is fully radiolucent. The variable marker 35663 is provided as an elongate lateral opening in the implant, however, other structures are possible. In some embodiments, the variable marker 35663 can be multiple discrete openings or voids that appear in a line away from the viewer in the aligned view and appear individually in a misaligned view. In some embodiments, the variable marker 663 can be multiple omitted struts, omitted nodes, smaller struts than the surrounding structure or smaller nodes than the surrounding structure that appear in a line away from the viewer in the aligned view and appear individually in a misaligned view. In the misaligned view of FIG. 36, the variable implant marker 35663 is hidden by the more radiodense surrounding structure.

Figure 38:
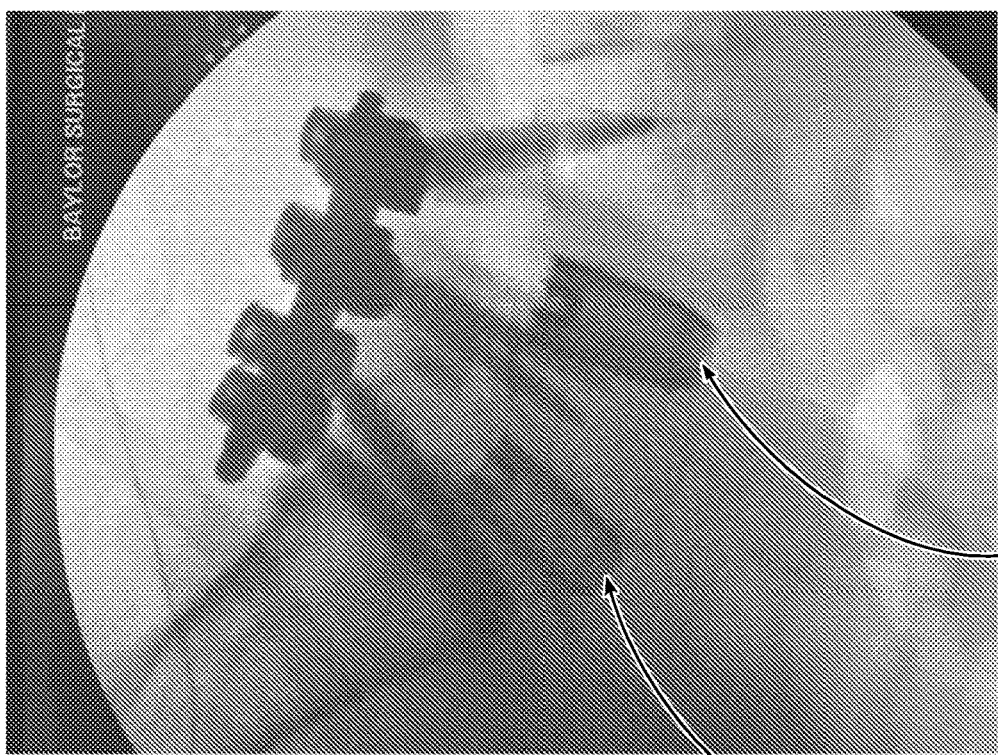
FIG. 38 is an example of an interbody fusion implant, designed using the high x-ray lucency lattice and methods of designing a high x-ray lucency lattice disclosed herein, and imaged on an x-ray machine in a lateral direction.
Figure 37:
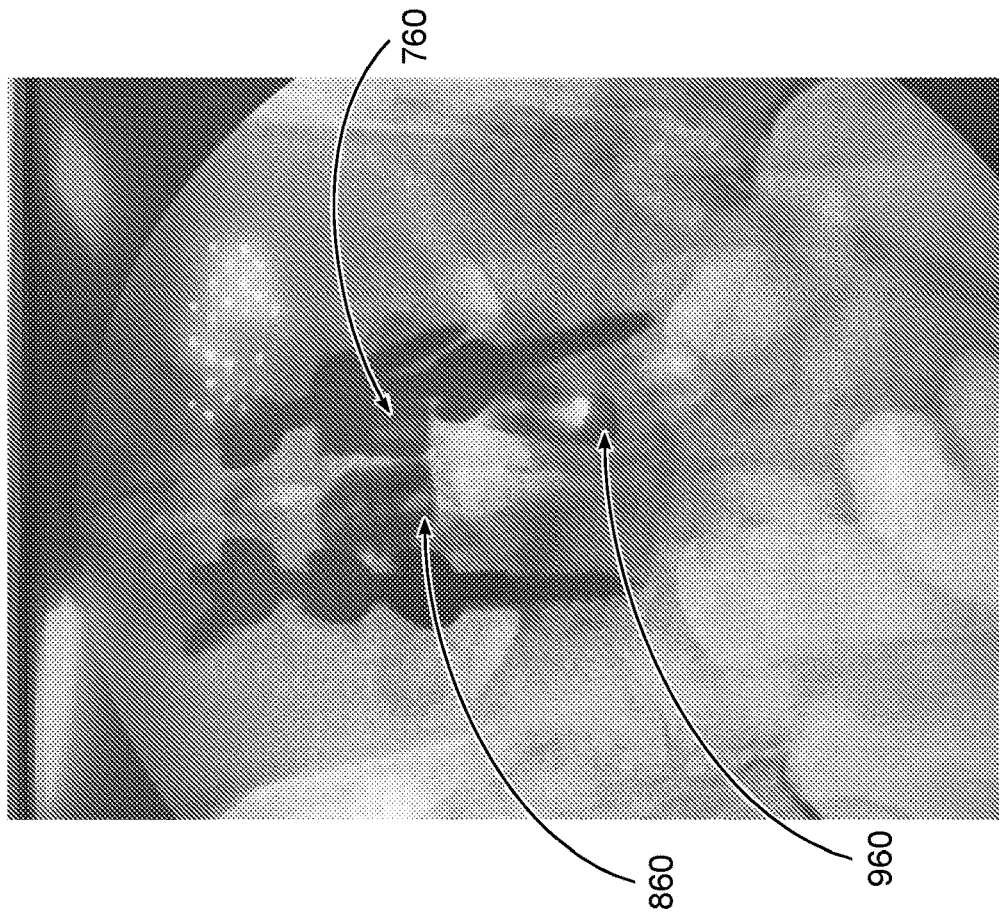
FIG. 37 is an example of an interbody fusion implant, designed using the high x-ray lucency lattice and methods of designing a high x-ray lucency lattice disclosed herein, and imaged on an x-ray machine in the anterior to posterior direction.

FIGS. 37-38 depict an example of an interbody fusion implant, designed using the high x-ray lucency lattice and methods of designing a high x-ray lucency lattice disclosed herein, and imaged on an x-ray machine. The image in FIG. 37 was taken from the anterior to posterior direction and the image in FIG. 38 was taken in a lateral direction. These x-ray images of a first implant 760, a second implant 860 and a third implant 960 were taken from predetermined desired directions, which are the anterior to posterior and lateral directions in this case. The exemplary implants 760, 860 & 960 include endplates with a higher volumetric density than the lattice body, making the endplates appear darker in the x-ray image than the lattice body. The fixation rods and screws on either side of the implants 760, 860 & 960 were not constructed or designed according to the disclosure herein and are largely radiopaque. In comparison, the lattice body portion of the implants 760, 860 & 960 constructed and designed according to the disclosure herein are significantly more radiolucent than the fixation rods and screws.

What has been described is a biocompatible lattice with high x-ray lucency, a method of designing a lattice with high x-ray lucency, variable markers for use in medical implants with at least a degree of radiolucency, a method of designing variable markers for use in medical implants with at least a degree of radiolucency and a method of using variable markers in medical implants with a degree of radiolucency. In this disclosure, there are shown and described only exemplary embodiments of the invention, but, as aforementioned, it is to be understood that the invention is capable of use in various other combinations and environments and is capable of changes or modifications within the scope of the inventive concept as expressed herein.

The invention claimed is:

1. A method for designing a porous structure having an increased lucency property, the method comprising:
   generating a bulk volume comprising a plurality of repeating structures in a form capable of analysis by an analysis tool, wherein the analysis tool is configured to analyze at least one of a strut diameter, a cell height, a cell width, a cell depth, a device thickness, a device height, and a device length in order to determine at least one rotation angle of the bulk volume;

propagating the bulk volume at an orientation determined at least in part by the at least one rotation angle of the bulk volume;

calculating a uniformity of bulk thickness across the structure along a desired direction for viewing, wherein the desired direction corresponds to a direction along which the increased lucency property is desired;

iterating across rotations of the bulk volume to identify a desired maximum uniformity of bulk thickness;

capturing the at least one rotation angle of the bulk volume at which the desired maximum uniformity of bulk thickness occurs;

generating a final structure for the porous structure based on the captured at least one rotation angle; and displaying at least a portion of the final structure for visualization via a visualization tool.

2. The method of claim 1, wherein the visualization tool comprises a 2D heat map of the structure in the desired direction.

3. The method of claim 1, further comprising calculating the uniformity of the bulk thickness using a coefficient of determination.

4. The method of claim 1, wherein the plurality of repeating structures comprise a lattice structure.

5. The method of claim 4, wherein the lattice structure comprises at least one of a radial dodeca-rhombus geometry, a rhombic dodecahedron geometry, a modified rhombic dodecahedron geometry, a diamond geometry, a dodecahedron geometry, a square geometry, a pentagonal geometry, a hexagonal geometry, an octagonal geometry, a sctet struts geometry, a trunic octa geometry, a diagonal struts and rounded geometry, a reinforced geometry, and a weakened geometry.

6. The method of claim 4, further comprising selecting a focal length for the porous structure.

7. The method of claim 1, further comprising sectioning the bulk volume to one or more segments corresponding to approximate dimensions of a selected implant type.

8. The method of claim 1, further comprising determining the desired maximum uniformity of bulk thickness based on at least one of relative dispersion and relative disparity of the porous structure.

9. The method of claim 1, further comprising translating the porous structure from its original orientation to a second orientation.

10. A method for designing a porous structure having an increased lucency property, the method comprising:

generating a bulk volume comprising a plurality of repeating structures in a form capable of analysis by an analysis tool, wherein the bulk volume is sectioned into one or more portions corresponding to approximate dimensions of an implant type, wherein the analysis tool is configured to analyze at least one of a strut diameter, a cell height, a cell width, a cell depth, a device thickness, a device height, and a device length in order to determine at least one rotation angle of the bulk volume;

propagating the bulk volume at an orientation determined at least in part by the at least one rotation angle of the bulk volume;

calculating a first uniformity of bulk thickness across the structure along a first desired direction for viewing, wherein the desired direction corresponds to a direction along which the increased lucency property is desired;

calculating a second uniformity of bulk thickness across the structure along a second desired direction for viewing, wherein the second desired direction for viewing corresponds to a direction along which a second lucency property is desired;

iterating across rotations of the bulk volume to identify a desired first uniformity of bulk thickness along the first desired direction for viewing and a desired second uniformity of bulk thickness along the second desired direction for viewing; and capturing at least one rotation angle of the bulk volume at which the desired first uniformity of bulk thickness occurs along the first direction and at which the desired second uniformity of bulk thickness occurs along the second direction;

generating a final structure for the porous structure based on the captured at least one rotation angle; and displaying at least a portion of the final structure for visualization via a visualization tool.

11. The method of claim 10, further comprising determining the desired uniformity of bulk medium along at least one of the first and second directions based on at least one of relative dispersion and relative disparity of the porous structure.

* * * * *